United States Patent [19]

Kanno et al.

[11] Patent Number: 5,723,412
[45] Date of Patent: Mar. 3, 1998

[54] 2-BENZYLOXY-4-PHENOXYPYRIMIDINE DERIVATIVE, PROCESSES FOR PRODUCING THE DERIVATIVE AND HERBICIDAL COMPOSITION CONTAINING THE DERIVATIVE

[75] Inventors: Hisashi Kanno; Yoshikazu Kubota; Tsutomu Sato; Masato Arahira, all of Iwaki, Japan

[73] Assignee: Kureha Kagaku Kogyo Kabushiki Kaisha, Japan

[21] Appl. No.: 502,208

[22] Filed: Jul. 13, 1995

[30] Foreign Application Priority Data

Jul. 15, 1994 [JP] Japan .................. 6-186708

[51] Int. Cl.$^6$ ................ C07D 239/53; A01N 43/54
[52] U.S. Cl. ................ 504/243; 544/299; 544/302; 544/303; 544/313; 544/314; 544/309
[58] Field of Search .................. 544/299, 302, 544/303, 313, 314, 309; 504/243

[56] References Cited

U.S. PATENT DOCUMENTS 4,985,066  1/1991  Wada et al. ................ 544/225

FOREIGN PATENT DOCUMENTS 2113216  8/1983  United Kingdom.
2 285 045  5/1995  United Kingdom.

OTHER PUBLICATIONS

J. Chem. Soc. 1965, 5542–5551, "The Dimroth Rearrangement. Part IV" by Brown et al.
J. Chem. Soc. 1975, 1798–1802, "Unconventional Nucleotide Analogues. Part XIV" by Kaspersen et al.
J. Chem. Soc. 1959, 525–530, "Pyrimidines, Part X" by Hunt et al.
Agr. Biol. Chem. vol. 30, No. 9, pp.896–905, 1966, "Synthesis and Herbicidal Activities of Phenoxypyrimidines and Phenoxytriazines" by Jojima et al.

Primary Examiner—John M. Ford
Attorney, Agent, or Firm—Parkhurst & Wendel, L.L.P.

[57] ABSTRACT

A 2-benzyloxy-4-phenoxypyrimidine derivative represented by the formula (I):

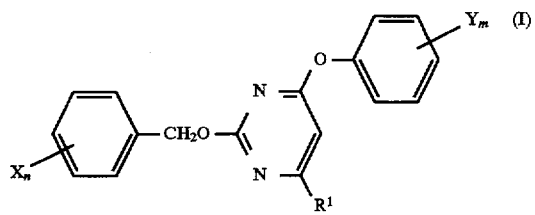

wherein $R^1$ represents hydrogen, a halogen, $C_1$–$C_4$ alkyl, $C_1$–$C_4$ haloalkyl, $C_1$–$C_4$ alkoxy, $C_1$–$C_4$ haloalkoxy, $C_3$–$C_5$ alkenyloxy, $C_1$–$C_4$ alkylthio, $C_1$–$C_4$ haloalkylthio, cyano, or phenyl;

each X, which may be identical or different if n is greater than 1, represents a halogen, $C_1$–$C_4$ alkyl, $C_1$–$C_4$ haloalkyl, or $C_1$–$C_4$ alkoxy;

each Y, which may be identical or different if m is greater than 1, represents a halogen, $C_1$–$C_4$ alkyl, $C_1$–$C_4$ haloalkyl, $C_1$–$C_4$ alkoxy, $C_1$–$C_4$ haloalkoxy, $C_1$–$C_4$ alkylthio, or $C_1$–$C_4$ haloalkylthio; and n and m each independently represent an integer of 0 to 5, which is useful as a herbicide.

10 Claims, No Drawings

2-BENZYLOXY-4-PHENOXYPYRIMIDINE DERIVATIVE, PROCESSES FOR PRODUCING THE DERIVATIVE AND HERBICIDAL COMPOSITION CONTAINING THE DERIVATIVE

BACKGROUND OF THE INVENTION

The present invention relates to a novel 2-benzyloxy-4-phenoxypyrimidine derivative, processes for producing the derivative and a herbicidal composition containing the derivative as an active ingredient.

Compounds which have the structural formulae partly common with those of the present invention are known as cited in the following.

Among 2-benzyloxypyrimidine derivatives, three compounds, namely, 2-benzyloxypyrimidine, 2-benzyloxy-4-ethoxypyrimidine, and 2-benzyloxy-4,6-dimethylpyrimidine are described respectively in the following publications: 2-benzyloxypyrimidine: J. Chem. Soc., 1965, 5542–5549; 2-benzyloxy-4-ethoxypyrimidine: J. Chem. Soc., Perkin Trans. 1, 1975, 1798–1802; and 2-benzyloxy-4,6-dimethylpyrimidine: J. Chem. Soc., 1959, 525–530.

However, these publications have suggested nothing about herbicidal activity thereof.

On the other hand, phenoxypyrimidine derivatives and herbicidal activity thereof have been described in Agri. Biol. Chem., 30, 896–905 (1966).

The present inventors have established a process for the preparation of a novel 2-benzyloxy-4-phenoxypyrimidine derivative and also have found that the compound has herbicidal properties, and thus attained the present invention.

SUMMARY OF THE INVENTION

In a first aspect of the present invention, there is provided a 2-benzyloxy-4-phenoxypyrimidine derivative represented by the formula (I):

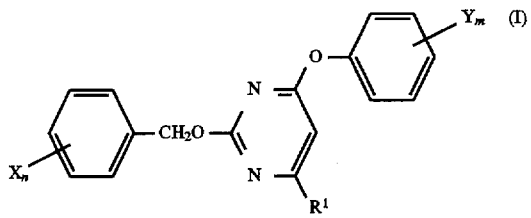

wherein $R^1$ represents hydrogen, a halogen, $C_1$–$C_4$ alkyl, $C_1$–$C_4$ haloalkyl, $C_1$–$C_4$ alkoxy, $C_1$–$C_4$ haloalkoxy, $C_3$–$C_5$ alkenyloxy, $C_1$–$C_4$ alkylthio, $C_1$–$C_4$ haloalkylthio, cyano, or phenyl;

each X, which may be identical or different if n is greater than 1, represents a halogen, $C_1$–$C_4$ alkyl, $C_1$–$C_4$ haloalkyl, or $C_1$–$C_4$ alkoxy;

each Y, which may be identical or different if m is greater than 1, represents a halogen, $C_1$–$C_4$ alkyl, $C_1$–$C_4$ haloalkyl, $C_1$–$C_4$ alkoxy, $C_1$–$C_4$ haloalkoxy, $C_1$–$C_4$ alkylthio, or $C_1$–$C_4$ haloalkylthio; and n and m each independently represent an integer of 0 to 5.

In a second aspect of the present invention, there is provided a process for producing a 2-benzyloxy-4-phenoxypyrimidine derivative of the formula (I):

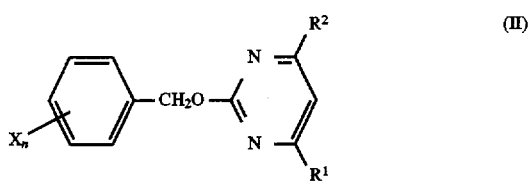

wherein $R^1$, X, Y, m, and n are as defined above, which comprises reacting a 2-benzyloxy-4 (or 6)-halogeno (or 4,6-dihalogeno) pyrimidine derivative of the formula (II):

wherein $R^1$, X, and n are as defined above and $R^2$ represents a halogen, with a phenol compound of the formula (III):

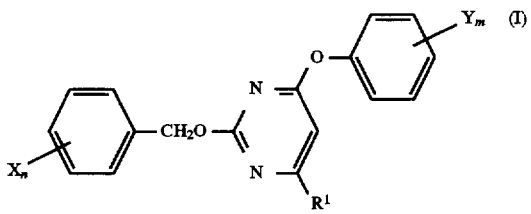

wherein Y and m are as defined above, in the presence of a basic compound.

In a third aspect of the present invention, there is provided a process for producing a 2-benzyloxy-4-phenoxypyrimidine derivative of the formula (I-a):

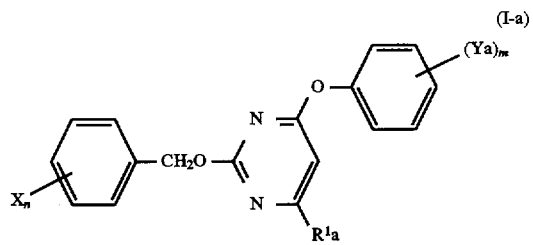

wherein $R^1a$ represents hydrogen, a halogen, $C_1$–$C_4$ alkyl, $C_1$–$C_4$ haloalkyl, $C_1$–$C_4$ alkoxy, $C_1$–$C_4$ haloalkoxy, $C_3$–$C_5$ alkenyloxy, cyano, or phenyl;

each X, which may be identical or different if n is greater than 1, represents a halogen, $C_1$–$C_4$ alkyl, $C_1$–$C_4$ haloalkyl, or $C_1$–$C_4$ alkoxy;

each Ya, which may be identical or different if m is greater than 1, represents a halogen, $C_1$–$C_4$ alkyl, $C_1$–$C_4$ haloalkyl, $C_1$–$C_4$ alkoxy, or $C_1$–$C_4$ haloalkoxy; and n and m each independently represent an integer of 0 to 5, which comprises reacting a 2-(substituted sulfonyl)-4-phenoxypyrimidine derivative of the formula (V):

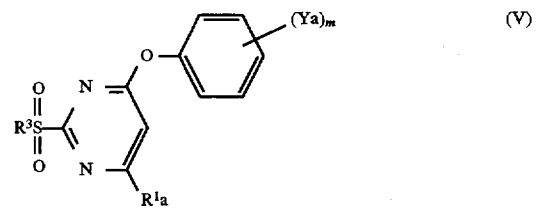

wherein $R^1a$, Ya and m are as defined above and $R^3$ represents $C_1$–$C_4$ alkyl, $C_7$–$C_9$ aralkyl, or aryl, with a benzyl alcohol compound of the formula (IV):

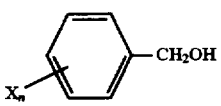

(IV)

wherein X and n are as defined above, in the presence of a basic compound.

In a fourth aspect of the present invention, there is provided a herbicidal composition comprising a 2-benzyloxy-4-phenoxypyrimidine derivative represented by the formula (I):

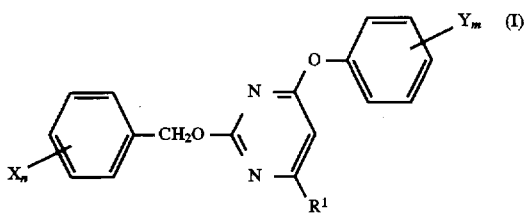

(I)

wherein $R^1$, X, Y, m, and n are as defined above, and an adjuvant.

DETAILED DESCRIPTION OF THE INVENTION

As used herein, the terms "haloalkyl", "haloalkoxy" and "haloalkylthio" respectively mean alkyl, alkoxy and alkylthio in which at least one hydrogen is substituted with a halogen.

Atomic symbols, abbreviations, and rational formulae given in parentheses are employed in the tables giving examples of the compounds of the present invention: Table 1 (1/34 to 34/34), Table 2 (1/5 to 5/5), Table 3, Table 4, and Table 5 (1/12 to 12/12).

$R^1$ and $R^1a$ each independently include the following atoms and substituents:

hydrogen (H);

a halogen such as chlorine (Cl), bromine (Br), and iodine (I);

$C_3$–$C_5$ alkenyloxy such as allyloxy ($OCH_2CH=CH_2$), (2-methyl-2-propenyl)oxy, crotyloxy, (3-methyl-2-butenyl)oxy ($OCH_2CH=CMe_2$), and (3-methyl-3-butenyl)oxy;

$C_1$–$C_4$ alkyl such as methyl (Me), ethyl (Et), 1-methylethyl, 1,1-dimethylethyl (t-Bu), propyl, and butyl;

$C_1$–$C_4$ alkoxy such as methoxy (OMe), ethoxy (OEt), (1-methylethyl)oxy (O-i-Pr), propoxy (OPr), (2-methylpropyl)oxy, (1-methylpropyl)oxy, and butoxy (OBu);

$C_1$–$C_4$ alkylthio such as methylthio (SMe) and ethylthio (SEt);

$C_1$–$C_4$ haloalkyl such as trifluoromethyl ($CF_3$), fluoromethyl, difluoromethyl, and 2,2,2-trifluoroethyl;

$C_1$–$C_4$ haloalkoxy such as difluoromethoxy, 1,1,2,2-tetrafluoroethoxy, 2,2,2-trifluoroethoxy ($OCH_2CF_3$), 2-fluoroethoxy, 2-bromo-1,1,2-trifluoroethoxy, 2,2,3,3,3-pentafluoropropoxy, 1,1,2,3,3,3-hexafluoropropoxy, and 2-chloro-1,1,2-trifluoroethoxy;

$C_1$–$C_4$ haloalkylthio such as (2,2,2-trifluoroethyl)thio ($SCH_2CF_3$);

cyano (CN); and phenyl (Ph).

Preferably, $R^1$ represents hydrogen, a halogen (more preferably chlorine), methyl, methoxy, methylthio, or cyano.

Preferably, $R^1a$ represents hydrogen, a halogen (more preferably chlorine), methyl, methoxy, or cyano.

$R^2$ represents a halogen, preferably chlorine or bromine.

X includes the following atoms and groups:

a halogen such as fluorine (F), chlorine (Cl), bromine (Br), and iodine (I);

$C_1$–$C_4$ alkyl such as methyl (Me), ethyl, 1-methylethyl, and butyl;

$C_1$–$C_4$ alkoxy such as methoxy (OMe), ethoxy, (1-methylethyl)oxy, and (1-methylpropyl)oxy; and $C_1$–$C_4$ haloalkyl such as trifluoromethyl ($CF_3$), fluoromethyl, difluoromethyl, and 2,2,2-trifluoroethyl.

Preferably, X represents a halogen (more preferably fluorine or chlorine), methyl, methoxy, or trifluoromethyl.

More preferably, X or each of two Xs is a halogen (still more preferably fluorine or chlorine) or methyl which is bonded to the position 3 or 4.

Y and Ya each independently include the following atoms and groups:

a halogen such as fluorine (F), chlorine (Cl), bromine (Br), and iodine (I);

$C_1$–$C_4$ alkyl such as methyl (Me), ethyl, 1-methylethyl, and butyl;

$C_1$–$C_4$ alkoxy such as methoxy (OMe), ethoxy, (1-methylethyl)oxy, and (1-methylpropyl)oxy;

$C_1$–$C_4$ alkylthio such as methylthio (SMe) and ethylthio;

$C_1$–$C_4$ haloalkyl such as trifluoromethyl ($CF_3$), fluoromethyl, difluoromethyl, and 2,2,2-trifluoroethyl;

$C_1$–$C_4$ haloalkoxy such as difluoromethoxy, trifluoromethoxy ($OCF_3$), 1,1,2,2-tetrafluoroethoxy, 2,2,2-trifluoroethoxy, 2-fluoroethoxy, 2-bromo-1,1,2-trifluoroethoxy, 2,2,3,3,3-pentafluoropropoxy, 1,1,2,3,3-hexafluoropropoxy, and 2-chloro-1,1,2-trifluoroethoxy; and $C_1$–$C_4$ haloalkylthio such as trifluoromethylthio ($SCF_3$) and (2,2,2-trifluoroethyl)thio ($SCH_2CF_3$).

Preferably, Y represents a halogen (more preferably fluorine or chlorine), methyl, trifluoromethyl, trifluoromethoxy, or trifluoromethylthio.

Preferably, Ya represents a halogen (more preferably fluorine or chlorine), methyl, trifluoromethyl, or trifluoromethoxy.

More preferably, Y represents a halogen (still more preferably fluorine or chlorine), methyl, trifluoromethyl, trifluoromethoxy, or trifluoromethylthio which is bonded to the position 3.

More preferably, Ya represents a halogen (still more preferably fluorine or chlorine), methyl, trifluoromethyl, or trifluoromethoxy which is bonded to the position 3.

m represents an integer of 0 to 5, preferably 0 to 3, more preferably 0 or 1.

n represents an integer of 0 to 5, preferably 0 to 3, more preferably 0, 1 or 2.

If n is greater than 1, each X may be identical or different. If m is greater than 1, each Y and each Ya may be identical or different.

In the tables showing examples of the compounds, the positions bonded by atoms and substituents in the benzene ring are represented by figures and the symbol "—". For example, a methyl group bonded to the position 3 of the benzene ring is represented by 3-Me and two chlorine atoms respectively bonded to the position 2 and 4 are represented by 2,4-$Cl_2$. When n or m represents 0, "H" is shown.

More preferably, each substituent in the derivative of the formula (I) represents the following:

X or Xs bond to the position 3 and/or 4, and represent a halogen (still more preferably fluorine or chlorine) or methyl.

Y bonds to the position 3, and represents a halogen (still more preferably fluorine or chlorine), methyl, trifluoromethyl, trifluoromethoxy, or trifluoromethylthio.

$R^1$ represents hydrogen, a halogen (still more preferably fluorine or chlorine), methyl, methoxy, methylthio, or cyano.

$R^3$ includes the following groups:

$C_1$–$C_4$ alkyl such as methyl (Me) or ethyl;

$C_7$–$C_9$ aralkyl such as benzyl; and aryl (usually $C_6$–$C_7$) such as phenyl or p-tolyl.

According to the present invention, a solvent is used generally for the production of the derivative represented by the formula (I). Examples of the solvent are set forth below:

water;

organic acids such as formic acid, acetic acid, and propionic acid;

aromatic hydrocarbons such as benzene, toluene, xylene, and methylnaphthalene;

aliphatic hydrocarbons such as petroleum ether, pentane, hexane, heptane, and methylcyclohexane;

halogenated hydrocarbons such as methylene chloride, chloroform, carbon tetrachloride, and chlorobenzene;

alcohols such as methanol, ethanol, i-propanol, and t-butanol;

amides such as dimethylformamide, dimethylacetamide, and N-methyl-2-pyrrolidinone;

ethers such as diethyl ether, dimethoxyethane, diisopropyl ether, tetrahydrofuran, diglyme, and dioxane;

ketones such as acetone and methyl ethyl ketone; as well as others including carbon disulfide, acetonitrile, ethyl acetate, pyridine, dimethyl sulfoxide, hexamethylphosphoric amide, and the like.

When the process of the present invention is carried out in the presence of a solvent, the above solvent may be used alone or in combination of two or more. When the combination of the solvents incapable of forming a homogeneous phase is used, the reaction may suitably be conducted in the presence of a phase transfer catalyst such as a conventional quaternary ammonium salt or a crown ether.

Examples of the basic compounds which is used in the process of the present invention are as follows:

alkaline metal carbonates such as sodium carbonate and potassium carbonate;

alkaline earth metal carbonates such as magnesium carbonate, calcium carbonate, and barium carbonate;

alkaline metal hydroxides such as sodium hydroxide and potassium hydroxide;

alkaline earth metal hydroxides such as magnesium hydroxide and calcium hydroxide;

alkaline earth metal oxides such as magnesium oxide and calcium oxide;

alkaline metals such as lithium, sodium and potassium as well as alkaline earth metals such as magnesium;

alkaline metal alkoxides such as sodium methoxide, sodium ethoxide, and potassium t-butoxide;

alkaline metal hydrides such as sodium hydride and potassium hydride;

alkaline earth metal hydrides such as calcium hydride;

organic alkaline metal compounds such as methyl lithium, ethyl lithium, n-butyl lithium and phenyl lithium;

Grignard reagents such as methylmagnesium iodide, ethylmagnesium bromide, and n-butylmagnesium bromide;

organic copper compounds prepared from organic alkaline metal compounds or Grignard reagents and copper (I) salts;

alkaline metal amides such as lithium diisopropylamide;

ammonium hydroxides having a nitrogen atom optionally substituted with an alkyl group or an aralkyl group, such as aqueous ammonia, benzyl trimethyl ammonium hydroxide and tetramethyl ammonium hydroxide; and organic amines such as methylamine, ethylamine, n-propylamine, benzylamine, ethanolamine, dimethylamine, benzylmethylamine, dibenzylamine, triethylamine, triethanolamine, and pyridine.

If necessary, in the process of the present invention, an acidic compound may be used for post-treatment, for example. Examples of the acidic compound are as follows: inorganic acids such as hydrochloric acid, hydrobromic acid, hydroiodic acid, perchloric acid, and sulfuric acid; organic acids such as formic acid, acetic acid, butyric acid, and p-toluenesulfonic acid; and Lewis acids such as boron trifluoride, aluminium chloride, and zinc chloride.

Examples of the phenol compound represented by the formula (III) are as follows: phenol, 2-methylphenol, 2-methoxyphenol, 2-(trifluoromethyl)phenol, 2-bromophenol, 2-chlorophenol, 2-fluorophenol, 3-methylphenol, 3-methoxyphenol, 3-(methylthio)phenol, 3-(trifluoromethyl)phenol, 3-(trifluoromethoxy)phenol, 3-(trifluoromethylthio)phenol, 3-bromophenol, 3-chlorophenol, 3-fluorophenol, 3-iodophenol, 4-methylphenol, 4-methoxyphenol, 4-(methylthio)phenol, 4-(trifluoromethyl)phenol, 4-(trifluoromethoxy)phenol, 4-(trifluoromethylthio)phenol, 4-(2,2,2-trifluoroethylthio) phenol, 4-bromophenol, 4-chlorophenol, 4-fluorophenol, and 4-iodophenol.

Examples of the benzyl alcohol compound represented by the formula (IV) are as follows: benzyl alcohol, 2-methylbenzyl alcohol, 2-methoxybenzyl alcohol, 2-bromobenzyl alcohol, 2-chlorobenzyl alcohol, 2-fluorobenzyl alcohol, 3-methylbenzyl alcohol, 3-methoxybenzyl alcohol, 3-(trifluoromethyl)benzyl alcohol, 3-bromobenzyl alcohol, 3-chlorobenzyl alcohol, 3-fluorobenzyl alcohol, 3-iodobenzyl alcohol, 4-methylbenzyl alcohol, 4-methoxybenzyl alcohol, 4-(trifluoromethyl)benzyl alcohol, 4-bromobenzyl alcohol, 4-chlorobenzyl alcohol, 4-fluorobenzyl alcohol, 2,4-dimethoxybenzyl alcohol, 2,4-dichlorobenzyl alcohol, 2,4-difluorobenzyl alcohol, 3,4-dimethylbenzyl alcohol, 3,4-dichlorobenzyl alcohol, and 3,4-difluorobenzyl alcohol.

Examples of 2-benzyloxy-4-phenoxypyrimidine derivatives represented by the formula (I) are shown in Table 1 (1/34 to 34/34).

TABLE 1

| No. | $X_n$ | $Y_m$ | $R^1$ |
| --- | --- | --- | --- |
| I-1 | H for | H for | H |
| I-2 | Compound | Compound | $OCH_2CH=CH_2$ |
| I-3 | No. I-1 | No. I-1 | $OCH_2CH=CMe_2$ |
| I-4 | through | through | Me |
| I-5 | Compound | Compound | Et |
| I-6 | No. I-.27 | No. I-27 | t-Bu |
| I-7 | | | OMe |
| I-11 | | | OEt |
| I-12 | | | OPr |

TABLE 1-continued

| No. | $X_n$ | $Y_m$ | $R^1$ |
|---|---|---|---|
| I-13 | | | O-i-Pr |
| I-14 | | | OBu |
| I-15 | | | SMe |
| I-16 | | | SEt |
| I-17 | | | Ph |
| I-21 | | | CN |
| I-22 | | | $CF_3$ |
| I-23 | | | $OCH_2CF_3$ |
| I-24 | | | $SCH_2CF_3$ |
| I-25 | | | Br |
| I-26 | | | Cl |
| I-27 | | | I |
| I-31 | H for | 2-Me for | H |
| I-32 | Compound | Compound | $OCH_2CH=CH_2$ |
| I-33 | No. I-31 | No. I-31 | $OCH_2CH=CMe_2$ |
| I-34 | through | through | Me |
| I-35 | Compound | Compound | Et |
| I-36 | No. I-57 | No. I-57 | t-Bu |
| I-37 | | | OMe |
| I-41 | | | OEt |
| I-42 | | | OPr |
| I-43 | | | O-i-Pr |
| I-44 | | | OBu |
| I-45 | | | SMe |
| I-46 | | | SEt |
| I-47 | | | Ph |
| I-51 | | | CN |
| I-52 | | | $CF_3$ |
| I-53 | | | $OCH_2CF_3$ |
| I-54 | | | $SCH_2CF_3$ |
| I-55 | | | Br |
| I-56 | | | Cl |
| I-57 | | | I |
| I-61 | H for | 2-OMe for | H |
| I-62 | Compound | Compound | $OCH_2CH=CH_2$ |
| I-63 | No. I-61 | No. I-61 | $OCH_2CH=CMe_2$ |
| I-64 | through | through | Me |
| I-65 | Compound | Compound | Et |
| I-66 | No. I-87 | No. I-87 | t-Bu |
| I-67 | | | OMe |
| I-71 | | | OEt |
| I-72 | | | OPr |
| I-73 | | | O-i-Pr |
| I-74 | | | OBu |
| I-75 | | | SMe |
| I-76 | | | SEt |
| I-77 | | | Ph |
| I-81 | | | CN |
| I-82 | | | $CF_3$ |
| I-83 | | | $OCH_2CF_3$ |
| I-84 | | | $SCH_2CF_3$ |
| I-85 | | | Br |
| I-86 | | | Cl |
| I-87 | | | I |
| I-91 | H for | 2-$CF_3$ for | H |
| I-92 | Compound | Compound | $OCH_2CH=CH_2$ |
| I-93 | No. I-91 | No. I-91 | $OCH_2CH=CMe_2$ |
| I-94 | through | through | Me |
| I-95 | Compound | Compound | Et |
| I-96 | No. I-117 | No. I-117 | t-Bu |
| I-97 | | | OMe |
| I-101 | | | OEt |
| I-102 | | | OPr |
| I-103 | | | O-i-Pr |
| I-104 | | | OBu |
| I-105 | | | SMe |
| I-106 | | | SEt |
| I-107 | | | Ph |
| I-111 | | | CN |
| I-112 | | | $CF_3$ |
| I-113 | | | $OCH_2CF_3$ |
| I-114 | | | $SCH_2CF_3$ |
| I-115 | | | Br |
| I-116 | | | Cl |
| I-117 | | | I |
| I-121 | H for | 2-Br for | H |
| I-122 | Compound | Compound | $OCH_2CH=CH_2$ |
| I-123 | No. I-121 | No. I-121 | $OCH_2CH=CMe_2$ |
| I-124 | through | through | Me |
| I-125 | Compound | Compound | Et |
| I-126 | No. I-147 | No. I-147 | t-Bu |
| I-127 | | | OMe |
| I-131 | | | OEt |
| I-132 | | | OPr |
| I-133 | | | O-i-Pr |
| I-134 | | | OBu |
| I-135 | | | SMe |
| I-136 | | | SEt |
| I-137 | | | Ph |
| I-141 | | | CN |
| I-142 | | | $CF_3$ |
| I-143 | | | $OCH_2CF_3$ |
| I-144 | | | $SCH_2CF_3$ |
| I-145 | | | Br |
| I-146 | | | Cl |
| I-147 | | | I |
| I-151 | H for | 2-Cl for | H |
| I-152 | Compound | Compound | $OCH_2CH=CH_2$ |
| I-153 | No. I-151 | No. I-151 | $OCH_2CH-CMe_2$ |
| I-154 | through | through | Me |
| I-155 | Compound | Compound | Et |
| I-156 | No. I-177 | No. I-177 | t-Bu |
| I-157 | | | OMe |
| I-161 | | | OEt |
| I-162 | | | OPr |
| I-163 | | | O-i-Pr |
| I-164 | | | OBu |
| I-165 | | | SMe |
| I-166 | | | SEt |
| I-167 | | | Ph |
| I-171 | | | CN |
| I-172 | | | $CF_3$ |
| I-173 | | | $OCH_2CF_3$ |
| I-174 | | | $SCH_2CF_3$ |
| I-175 | | | Br |
| I-176 | | | Cl |
| I-177 | | | I |
| I-181 | H for | 2-F for | H |
| I-182 | Compound | Compound | $OCH_2CH=CH_2$ |
| I-183 | No. I-181 | No. I-181 | $OCH_2CH=CMe_2$ |
| I-184 | through | through | Me |
| I-185 | Compound | Compound | Et |
| I-186 | No. I-207 | No. I-207 | t-Bu |
| I-187 | | | OMe |
| I-191 | | | OEt |
| I-192 | | | OPr |
| I-193 | | | O-i-Pr |
| I-194 | | | OBu |
| I-195 | | | SMe |
| I-196 | | | SEt |
| I-197 | | | Ph |
| I-201 | | | CN |
| I-202 | | | $CF_3$ |
| I-203 | | | $OCH_2CF_3$ |
| I-204 | | | $SCH_2CF_3$ |
| I-205 | | | Br |
| I-206 | | | Cl |
| I-207 | | | I |
| I-211 | H for | H for | H |
| I-212 | Compound | Compound | $OCH_2CH=CH_2$ |
| I-213 | No. I-211 | No. I-211 | $OCH_2CH=CMe_2$ |
| I-214 | through | through | Me |
| I-215 | Compound | Compound | Et |
| I-216 | No. I-237 | No. I-237 | t-Bu |
| I-217 | | | OMe |
| I-221 | | | OEt |
| I-222 | | | OPr |
| I-223 | | | O-i-Pr |
| I-224 | | | OBu |
| I-225 | | | SMe |
| I-226 | | | SEt |
| I-227 | | | Ph |
| I-231 | | | CN |
| I-232 | | | $CF_3$ |

TABLE 1-continued

| No. | $X_n$ | $Y_m$ | $R^1$ |
|---|---|---|---|
| I-233 | | | OCH$_2$CF$_3$ |
| I-234 | | | SCH$_2$CF$_3$ |
| I-235 | | | Br |
| I-236 | | | Cl |
| I-237 | | | I |
| I-241 | H for | 3-OMe for | H |
| I-242 | Compound | Compound | OCH$_2$CH=CH$_2$ |
| I-243 | No. I-241 | No. I-241 | OCH$_2$CH=CMe$_2$ |
| I-244 | through | through | Me |
| I-245 | Compound | Compound | Et |
| I-246 | No. I-267 | No. I-267 | t-Bu |
| I-247 | | | OMe |
| I-251 | | | OEt |
| I-252 | | | OPr |
| I-253 | | | O-i-Pr |
| I-254 | | | OBu |
| I-255 | | | SMe |
| I-256 | | | SEt |
| I-257 | | | Ph |
| I-261 | | | CN |
| I-262 | | | CF$_3$ |
| I-263 | | | OCH$_2$CF$_3$ |
| I-264 | | | SCH$_2$CF$_3$ |
| I-265 | | | Br |
| I-266 | | | Cl |
| I-267 | | | I |
| I-271 | H for | 3-SMe for | H |
| I-272 | Compound | Compound | OCH$_2$CH=CH$_2$ |
| I-273 | No. I-271 | No. I-271 | OCH$_2$CH=CMe$_2$ |
| I-274 | through | through | Me |
| I-275 | Compound | Compound | Et |
| I-276 | No. I-297 | No. I-297 | t-Bu |
| I-277 | | | OMe |
| I-281 | | | OEt |
| I-282 | | | OPr |
| I-283 | | | O-i-Pr |
| I-284 | | | OBu |
| I-285 | | | SMe |
| I-286 | | | SEt |
| I-287 | | | Ph |
| I-291 | | | CN |
| I-292 | | | CF$_3$ |
| I-293 | | | OCH$_2$CF$_3$ |
| I-294 | | | SCH$_2$CF$_3$ |
| I-295 | | | Br |
| I-296 | | | Cl |
| I-297 | | | I |
| I-301 | H for | 3-CF$_3$ for | H |
| I-302 | Compound | Compound | OCH$_2$CH=CH$_2$ |
| I-303 | No. I-301 | No. I-301 | OCH$_2$CH=CMe$_2$ |
| I-304 | through | through | Me |
| I-305 | Compound | Compound | Et |
| I-306 | No. I-327 | No. I-327 | t-Bu |
| I-307 | | | OMe |
| I-311 | | | OEt |
| I-312 | | | OPr |
| I-313 | | | O-i-Pr |
| I-314 | | | OBu |
| I-315 | | | SMe |
| I-316 | | | SEt |
| I-317 | | | Ph |
| I-321 | | | CN |
| I-322 | | | CF$_3$ |
| I-323 | | | OCH$_2$CF$_3$ |
| I-324 | | | SCH$_2$CF$_3$ |
| I-325 | | | Br |
| I-326 | | | Cl |
| I-327 | | | I |
| I-331 | H for | 3-OCF$_3$ for | H |
| I-332 | Compound | Compound | OCH$_2$CH=CH$_2$ |
| I-333 | No. I-331 | No. I-331 | OCH$_2$CH=CMe$_2$ |
| I-334 | through | through | Me |
| I-335 | Compound | Compound | Et |
| I-336 | No. I-357 | No. I-357 | t-Bu |
| I-337 | | | OMe |
| I-341 | | | OEt |
| I-342 | | | OPr |
| I-343 | | | O-i-Pr |
| I-344 | | | OBu |
| I-345 | | | SMe |
| I-346 | | | SEt |
| I-347 | | | Ph |
| I-351 | | | CN |
| I-352 | | | CF$_3$ |
| I-353 | | | OCH$_2$CF$_3$ |
| I-354 | | | SCH$_2$CF$_3$ |
| I-355 | | | Br |
| I-356 | | | Cl |
| I-357 | | | I |
| I-361 | H for | 3-S$_6$F$_3$ for | H |
| I-362 | Compound | Compound | OCH$_2$CH=CH$_2$ |
| I-363 | No. I-361 | No. I-361 | OCH$_2$CH=CMe$_2$ |
| I-364 | through | through | Me |
| I-365 | Compound | Compound | Et |
| I-366 | No. I-387 | No. I-387 | t-Bu |
| I-367 | | | OMe |
| I-371 | | | OEt |
| I-312 | | | OPr |
| I-373 | | | O-i-Pr |
| I-374 | | | OBu |
| I-375 | | | SMe |
| I-376 | | | SEt |
| I-377 | | | Ph |
| I-381 | | | CN |
| I-382 | | | CF$_3$ |
| I-383 | | | OCH$_2$CF$_3$ |
| I-384 | | | SCH$_2$CF$_3$ |
| I-385 | | | Br |
| I-386 | | | Cl |
| I-387 | | | I |
| I-391 | H for | 3-Br for | H |
| I-392 | Compound | Compound | OCH$_2$CH=CH$_2$ |
| I-393 | No. I-391 | No. I-391 | OCH$_2$CH=CMe$_2$ |
| I-394 | through | through | Me |
| I-395 | Compound | Compound | Et |
| I-396 | No. I-417 | No. I-417 | t-Bu |
| I-397 | | | OMe |
| I-401 | | | OEt |
| I-402 | | | OPr |
| I-403 | | | O-i-Pr |
| I-404 | | | OBu |
| I-405 | | | SMe |
| I-406 | | | SEt |
| I-407 | | | Ph |
| I-411 | | | CN |
| I-412 | | | CF$_3$ |
| I-413 | | | OCH$_2$CF$_3$ |
| I-414 | | | SCH$_2$CF$_3$ |
| I-415 | | | Br |
| I-416 | | | Cl |
| I-417 | | | I |
| I-421 | H for | 3-Cl for | H |
| I-422 | Compound | Compound | OCH$_2$CH=CH$_2$ |
| I-423 | No. I-421 | No. I-421 | OCH$_2$CH=CMe$_2$ |
| I-424 | through | through | Me |
| I-425 | Compound | Compound | Et |
| I-426 | No. I-447 | No. I-447 | t-Bu |
| I-427 | | | OMe |
| I-431 | | | OEt |
| I-432 | | | OPr |
| I-433 | | | O-i-Pr |
| I-434 | | | OBu |
| I-435 | | | SMe |
| I-436 | | | SEt |
| I-437 | | | Ph |
| I-441 | | | CN |
| I-442 | | | CF$_3$ |
| I-443 | | | OCH$_2$CF$_3$ |
| I-444 | | | SCH$_2$CF$_3$ |
| I-445 | | | Br |
| I-446 | | | Cl |
| I-447 | | | I |
| I-451 | H for | 3-F for | H |
| I-452 | Compound | Compound | OCH$_2$CH=CH$_2$ |

TABLE 1-continued

| No. | $X_n$ | $Y_m$ | $R^1$ |
|---|---|---|---|
| I-453 | No. I-451 | No. I-451 | $OCH_2CH=CMe_2$ |
| I-454 | through | through | Me |
| I-455 | Compound | Compound | Et |
| I-456 | No. I-477 | No. I-477 | t-Bu |
| I-457 | | | OMe |
| I-461 | | | OEt |
| I-462 | | | OPr |
| I-463 | | | O-i-Pr |
| I-464 | | | OBu |
| I-465 | | | SMe |
| I-466 | | | SEt |
| I-467 | | | Ph |
| I-471 | | | CN |
| I-472 | | | $CF_3$ |
| I-473 | | | $OCH_2CF_3$ |
| I-474 | | | $SCH_2CF_3$ |
| I-475 | | | Br |
| I-476 | | | Cl |
| I-477 | | | I |
| I-481 | H for | 3-I for | H |
| I-482 | Compound | Compound | $OCH_2CH=CH_2$ |
| I-483 | No. I-481 | No. I-481 | $OCH_2CH=CMe_2$ |
| I-484 | through | through | Me |
| I-485 | Compound | Compound | Et |
| I-486 | No. I-507 | No. I-507 | t-Bu |
| I-487 | | | OMe |
| I-491 | | | OEt |
| I-492 | | | OPr |
| I-493 | | | O-i-Pr |
| I-494 | | | OBu |
| I-495 | | | SMe |
| I-496 | | | SEt |
| I-497 | | | Ph |
| I-501 | | | CN |
| I-502 | | | $CF_3$ |
| I-503 | | | $OCH_2CF_3$ |
| I-504 | | | $SCH_2CF_3$ |
| I-505 | | | Br |
| I-506 | | | Cl |
| I-507 | | | I |
| I-511 | H for | 4-Me for | H |
| I-512 | Compound | Compound | $OCH_2CH=CH_2$ |
| I-513 | No. I-511 | No. I-511 | $OCH_2CH=CMe_2$ |
| I-514 | through | through | Me |
| I-515 | Compound | Compound | Et |
| I-516 | No. I-537 | No. I-537 | t-Bu |
| I-517 | | | OMe |
| I-521 | | | OEt |
| I-522 | | | OPr |
| I-523 | | | O-i-Pr |
| I-524 | | | OBu |
| I-525 | | | SMe |
| I-526 | | | SEt |
| I-527 | | | Ph |
| I-531 | | | CN |
| I-532 | | | $CF_3$ |
| I-533 | | | $OCH_2CF_3$ |
| I-534 | | | $SCH_2CF_3$ |
| I-535 | | | Br |
| I-536 | | | Cl |
| I-537 | | | I |
| I-541 | H for | 4-OMe for | H |
| I-542 | Compound | Compound | $OCH_2CH=CH_2$ |
| I-543 | No. I-541 | No. I-541 | $OCH_2CH=CMe_2$ |
| I-544 | through | through | Me |
| I-545 | Compound | Compound | Et |
| I-546 | No. I-567 | No. I-567 | t-Bu |
| I-547 | | | OMe |
| I-551 | | | OEt |
| I-552 | | | OPr |
| I-553 | | | O-i-Pr |
| I-554 | | | OBu |
| I-555 | | | SMe |
| I-556 | | | SEt |
| I-557 | | | Ph |
| I-561 | | | CN |
| I-562 | | | $CF_3$ |
| I-563 | | | $OCH_2CF_3$ |
| I-564 | | | $SCH_2CF_3$ |
| I-565 | | | Br |
| I-566 | | | Cl |
| I-567 | | | I |
| I-571 | H for | 4-$CF_3$ for | H |
| I-572 | Compound | Compound | $OCH_2CH=CH_2$ |
| I-573 | No. I-571 | No. I-571 | $OCH_2CH=CMe_2$ |
| I-574 | through | through | Me |
| I-575 | Compound | Compound | Et |
| I-576 | No. I-597 | No. I-597 | t-Bu |
| I-577 | | | OMe |
| I-581 | | | OEt |
| I-582 | | | OPr |
| I-583 | | | O-i-Pr |
| I-584 | | | OBu |
| I-585 | | | SMe |
| I-586 | | | SEt |
| I-587 | | | Ph |
| I-591 | | | CN |
| I-592 | | | $CF_3$ |
| I-593 | | | $OCH_2CF_3$ |
| I-594 | | | $SCH_2CF_3$ |
| I-595 | | | Br |
| I-596 | | | Cl |
| I-597 | | | I |
| I-601 | H for | 4-$OCF_3$ for | H |
| I-602 | Compound | Compound | $OCH_2CH=CH_2$ |
| I-603 | No. I-601 | No. I-601 | $OCH_2CH=CMe_2$ |
| I-604 | through | through | Me |
| I-605 | Compound | Compound | Et |
| I-606 | No. I-627 | No. I-627 | t-Bu |
| I-607 | | | OMe |
| I-611 | | | OEt |
| I-612 | | | OPr |
| I-613 | | | O-i-Pr |
| I-614 | | | OBu |
| I-615 | | | SMe |
| I-616 | | | SEt |
| I-617 | | | Ph |
| I-621 | | | CN |
| I-622 | | | $CF_3$ |
| I-623 | | | $OCH_2CF_3$ |
| I-624 | | | $SCH_2CF_3$ |
| I-625 | | | Br |
| I-626 | | | Cl |
| I-627 | | | I |
| I-631 | H for | 4-$SCF_3$ for | H |
| I-632 | Compound | Compound | $OCH_2CH=CH_2$ |
| I-633 | No. I-631 | No. I-631 | $OCH_2CH=CMe_2$ |
| I-634 | through | through | Me |
| I-635 | Compound | Compound | Et |
| I-636 | No. I-657 | No. I-657 | t-Bu |
| I-637 | | | OMe |
| I-641 | | | OEt |
| I-642 | | | OPr |
| I-643 | | | O-i-Pr |
| I-644 | | | OBu |
| I-645 | | | SMe |
| I-646 | | | SEt |
| I-647 | | | Ph |
| I-651 | | | CN |
| I-652 | | | $CF_3$ |
| I-653 | | | $OCH_2CF_3$ |
| I-654 | | | $SCH_2CF_3$ |
| I-655 | | | Br |
| I-656 | | | Cl |
| I-657 | | | I |
| I-661 | H for | 4-$SCH_2CF_3$ | H |
| I-662 | Compound | for | $OCH_2CH=CH_2$ |
| I-663 | No. I-661 | Compound | $OCH_2CH=CMe_2$ |
| I-664 | through | No. I-661 | Me |
| I-665 | Compound | through | Et |
| I-666 | No. I-687 | Compound | t-Bu |
| I-667 | | No. I-687 | OMe |
| I-671 | | | OEt |
| I-672 | | | OPr |

TABLE 1-continued

| No. | $X_n$ | $Y_m$ | $R^1$ |
|---|---|---|---|
| I-673 | | | O-i-Pr |
| I-674 | | | OBu |
| I-675 | | | SMe |
| I-676 | | | SEt |
| I-677 | | | Ph |
| I-681 | | | CN |
| I-682 | | | $CF_3$ |
| I-683 | | | $OCH_2CF_3$ |
| I-684 | | | $SCH_2CF_3$ |
| I-685 | | | Br |
| I-686 | | | Cl |
| I-687 | | | I |
| I-691 | H for | 4-Br for | H |
| I-692 | Compound | Compound | $OCH_2CH=CH_2$ |
| I-693 | No. I-691 | No. I-691 | $OCH_2CH=CMe_2$ |
| I-694 | through | through | Me |
| I-695 | Compound | Compound | Et |
| I-696 | No. I-717 | No. I-717 | t-Bu |
| I-697 | | | OMe |
| I-701 | | | OEt |
| I-702 | | | OPr |
| I-703 | | | O-i-Pr |
| I-704 | | | OBu |
| I-705 | | | SMe |
| I-706 | | | SEt |
| I-707 | | | Ph |
| I-711 | | | CN |
| I-712 | | | $CF_3$ |
| I-713 | | | $OCH_2CF_3$ |
| I-714 | | | $SCH_2CF_3$ |
| I-715 | | | Br |
| I-716 | | | Cl |
| I-717 | | | I |
| I-721 | H for | 4-Cl for | H |
| I-722 | Compound | Compound | $OCH_2CH=CH_2$ |
| I-723 | No. I-721 | No. I-721 | $OCH_2CH=CMe_2$ |
| I-724 | through | through | Me |
| I-725 | Compound | Compound | Et |
| I-726 | No. I-747 | No. I-747 | t-Bu |
| I-727 | | | OMe |
| I-731 | | | OEt |
| I-732 | | | OPr |
| I-733 | | | O-i-Pr |
| I-734 | | | OBu |
| I-735 | | | SMe |
| I-736 | | | SEt |
| I-737 | | | Ph |
| I-741 | | | CN |
| I-742 | | | $CF_3$ |
| I-743 | | | $OCH_2CF_3$ |
| I-744 | | | $SCH_2CF_3$ |
| I-745 | | | Br |
| I-746 | | | Cl |
| I-747 | | | I |
| I-751 | H for | 4-F for | H |
| I-752 | Compound | Compound | $OCH_2CH=CH_2$ |
| I-753 | No. I-751 | No. I-751 | $OCH_2CH=CMe_2$ |
| I-754 | through | through | Me |
| I-755 | Compound | Compound | Et |
| I-756 | No. I-777 | No. I-777 | t-Bu |
| I-757 | | | OMe |
| I-761 | | | OEt |
| I-762 | | | OPr |
| I-763 | | | O-i-Pr |
| I-764 | | | OBu |
| I-765 | | | SMe |
| I-766 | | | SEt |
| I-767 | | | Ph |
| I-771 | | | CN |
| I-772 | | | $CF_3$ |
| I-773 | | | $OCH_2CF_3$ |
| I-774 | | | $SCH_2CF_3$ |
| I-775 | | | Br |
| I-776 | | | Cl |
| I-777 | | | I |
| I-781 | H for | 4-I for | H |
| I-782 | Compound | Compound | $OCH_2CH=CH_2$ |
| I-783 | No. I-781 | No. I-781 | $OCH_2CH=CMe_2$ |
| I-784 | through | through | Me |
| I-785 | Compound | Compound | Et |
| I-786 | No. I-807 | No. I-807 | t-Bu |
| I-787 | | | OMe |
| I-791 | | | OEt |
| I-792 | | | OPr |
| I-793 | | | O-i-Pr |
| I-794 | | | OBu |
| I-795 | | | SMe |
| I-796 | | | SEt |
| I-797 | | | Ph |
| I-801 | | | CN |
| I-802 | | | $CF_3$ |
| I-803 | | | $OCH_2CF_3$ |
| I-804 | | | $SCH_2CF_3$ |
| I-805 | | | Br |
| I-806 | | | Cl |
| I-807 | | | I |
| I-811 | 2-Me | H | $OCH_2CH=CH_2$ |
| I-812 | 2-Me | H | Me |
| I-813 | 2-Me | H | OMe |
| I-814 | 2-Me | H | OEt |
| I-815 | 2-Me | H | $CF_3$ |
| I-816 | 2-Me | H | Cl |
| I-817 | 2-Me | 3-Me | $OCH_2CH=CH_2$ |
| I-821 | 2-Me | 3-Me | Me |
| I-822 | 2-Me | 3-Me | OMe |
| I-823 | 2-Me | 3-Me | OEt |
| I-824 | 2-Me | 3-Me | $CF_3$ |
| I-825 | 2-Me | 3-Me | Cl |
| I-826 | 2-Me | 3-OMe | $OCH_2CH=CH_2$ |
| I-827 | 2-Me | 3-OMe | Me |
| I-831 | 2-Me | 3-OMe | OMe |
| I-832 | 2-Me | 3-OMe | OEt |
| I-833 | 2-Me | 3-OMe | $CF_3$ |
| I-834 | 2-Me | 3-OMe | Cl |
| I-835 | 2-Me | 3-$CF_3$ | $OCH_2CH=CH_2$ |
| I-836 | 2-Me | 3-$CF_3$ | Me |
| I-837 | 2-Me | 3-$CF_3$ | OMe |
| I-841 | 2-Me | 3-$CF_3$ | OEt |
| I-842 | 2-Me | 3-$CF_3$ | $CF_3$ |
| I-843 | 2-Me | 3-$CF_3$ | Cl |
| I-844 | 2-Me | 3-Cl | $OCH_2CH=CH_2$ |
| I-845 | 2-Me | 3-Cl | Me |
| I-846 | 2-Me | 3-Cl | OMe |
| I-847 | 2-Me | 3-Cl | OEt |
| I-851 | 2-Me | 3-Cl | $CF_3$ |
| I-852 | 2-Me | 3-Cl | Cl |
| I-853 | 2-OMe | H | $OCH_2CH=CH_2$ |
| I-854 | 2-OMe | H | Me |
| I-855 | 2-OMe | H | OMe |
| I-856 | 2-OMe | H | OEt |
| I-857 | 2-OMe | H | $CF_3$ |
| I-861 | 2-OMe | H | Cl |
| I-862 | 2-OMe | 3-Me | $OCH_2CH=CH_2$ |
| I-863 | 2-OMe | 3-Me | Me |
| I-864 | 2-OMe | 3-Me | OMe |
| I-865 | 2-OMe | 3-Me | OEt |
| I-866 | 2-OMe | 3-Me | $CF_3$ |
| I-867 | 2-OMe | 3-Me | Cl |
| I-871 | 2-OMe | 3-OMe | $OCH_2CH=CH_2$ |
| I-872 | 2-OMe | 3-OMe | Me |
| I-873 | 2-OMe | 3-OMe | OMe |
| I-874 | 2-OMe | 3-OMe | OEt |
| I-875 | 2-OMe | 3-OMe | $CF_3$ |
| I-876 | 2-OMe | 3-OMe | Cl |
| I-877 | 2-OMe | 3-$CF_3$ | $OCH_2CH=CH_2$ |
| I-881 | 2-OMe | 3-$CF_3$ | Me |
| I-882 | 2-OMe | 3-$CF_3$ | OMe |
| I-883 | 2-OMe | 3-$CF_3$ | OEt |
| I-884 | 2-OMe | 3-$CF_3$ | $CF_3$ |
| I-885 | 2-OMe | 3-$CF_3$ | Cl |
| I-886 | 2-OMe | 3-Cl | $OCH_2CH=CH_2$ |
| I-887 | 2-OMe | 3-Cl | Me |
| I-891 | 2-OMe | 3-Cl | OMe |
| I-892 | 2-OMe | 3-Cl | OEt |

TABLE 1-continued

| No. | $X_n$ | $Y_m$ | $R^1$ |
|---|---|---|---|
| I-893 | 2-OMe | 3-Cl | CF₃ |
| I-894 | 2-OMe | 3-CL | Cl |
| I-895 | 2-Br | H | OCH₂CH=CH₂ |
| I-896 | 2-Br | H | Me |
| I-897 | 2-Br | H | OMe |
| I-901 | 2-Br | H | OEt |
| I-902 | 2-Br | H | CF₃ |
| I-903 | 2-Br | H | Cl |
| I-904 | 2-Br | 3-Me | OCH₂CH=CH₂ |
| J-905 | 2-Br | 3-Me | Me |
| I-906 | 2-Br | 3-Me | OMe |
| I-907 | 2-Br | 3-Me | OEt |
| I-911 | 2-Br | 3-Me | CF₃ |
| I-912 | 2-Br | 3-Me | Cl |
| I-913 | 2-Br | 3-OMe | OCH₂CH=CH₂ |
| I-914 | 2-Br | 3-OMe | Me |
| I-915 | 2-Br | 3-OMe | OMe |
| I-916 | 2-Br | 3-OMe | OEt |
| I-917 | 2-Br | 3-OMe | CF₃ |
| I-921 | 2-Br | 3-OMe | Cl |
| I-922 | 2-Br | 3-CF₃ | OCH₂CH=CH₂ |
| I-923 | 2-Br | 3-CF₃ | Me |
| I-924 | 2-Br | 3-CF₃ | OMe |
| I-925 | 2-Br | 3-CF₃ | OEt |
| I-926 | 2-Br | 3-CF₃ | CF₃ |
| I-927 | 2-Br | 3-CF₃ | Cl |
| I-931 | 2-Br | 3-Cl | OCH₂CH=CH₂ |
| I-932 | 2-Br | 3-Cl | Me |
| I-933 | 2-Br | 3-Cl | OMe |
| I-934 | 2-Br | 3-Cl | OEt |
| I-935 | 2-Br | 3-Cl | CF₃ |
| I-936 | 2-Br | 3-Cl | Cl |
| I-937 | 2-Cl | H | OCH₂CH=CH₂ |
| I-941 | 2-Cl | H | Me |
| I-942 | 2-Cl | H | OMe |
| I-943 | 2-Cl | H | OEt |
| I-944 | 2-Cl | H | CF₃ |
| I-945 | 2-Cl | H | Cl |
| I-946 | 2-Cl | 3-Me | OCH₂CH=CH₂ |
| I-947 | 2-Cl | 3-Me | Me |
| I-951 | 2-Cl | 3-Me | OMe |
| I-952 | 2-Cl | 3-Me | OEt |
| I-953 | 2-Cl | 3-Me | CF₃ |
| I-954 | 2-Cl | 3-Me | Cl |
| I-955 | 2-Cl | 3-OMe | OCH₂CH=CH₂ |
| I-956 | 2-Cl | 3-OMe | Me |
| I-957 | 2-Cl | 3-OMe | OMe |
| I-961 | 2-Cl | 3-OMe | OEt |
| I-962 | 2-Cl | 3-OMe | CF₃ |
| I-963 | 2-Cl | 3-OMe | Cl |
| I-964 | 2-Cl | 3-CF₃ | OCH₂CH=CH₂ |
| I-965 | 2-Cl | 3-CF₃ | Me |
| I-966 | 2-Cl | 3-CF₃ | OMe |
| I-967 | 2-Cl | 3-CF₃ | OEt |
| I-971 | 2-Cl | 3-CF₃ | CF₃ |
| I-972 | 2-Cl | 3-CF₃ | Cl |
| I-973 | 2-Cl | 3-Cl | OCH₂CH=CH₂ |
| I-974 | 2-Cl | 3-Cl | Me |
| I-975 | 2-Cl | 3-Cl | OMe |
| I-976 | 2-Cl | 3-Cl | OEt |
| I-977 | 2-Cl | 3-Cl | CF₃ |
| I-981 | 2-Cl | 3-Cl | Cl |
| I-982 | 2-F | H | OCH₂CH=CH₂ |
| I-983 | 2-F | H | Me |
| I-984 | 2-F | H | OMe |
| I-985 | 2-F | H | OEt |
| I-986 | 2-F | H | CF₃ |
| I-987 | 2-F | H | Cl |
| I-991 | 2-F | 3-Me | OCH₂CH=CH₂ |
| I-992 | 2-F | 3-Me | Me |
| I-993 | 2-F | 3-Me | OMe |
| I-994 | 2-F | 3-Me | OEt |
| I-995 | 2-F | 3-Me | CF₃ |
| I-996 | 2-F | 3-Me | Cl |
| I-997 | 2-F | 3-OMe | OCH₂CH=CH₂ |
| I-1001 | 2-F | 3-OMe | Me |
| I-1002 | 2-F | 3-OMe | OMe |
| I-1003 | 2-F | 3-OMe | OEt |
| I-1004 | 2-F | 3-OMe | CF₃ |
| I-1005 | 2-F | 3-OMe | Cl |
| I-1006 | 2-F | 3-CF₃ | OCH₂CH=CH₂ |
| I-1007 | 2-F | 3-CF₃ | Me |
| I-1011 | 2-F | 3-CF₃ | OMe |
| I-1012 | 2-F | 3-CF₃ | OEt |
| I-1013 | 2-F | 3-CF₃ | CF₃ |
| I-1014 | 2-F | 3-CF₃ | Cl |
| I-1015 | 2-F | 3-Cl | OCH₂CH=CH₂ |
| I-1016 | 2-F | 3-Cl | Me |
| I-1017 | 2-F | 3-Cl | OMe |
| I-1021 | 2-F | 3-Cl | OEt |
| I-1022 | 2-F | 3-Cl | CF₃ |
| I-1023 | 2-F | 3-Cl | Cl |
| I-1024 | 3-I | H | OCH₂CH=CH₂ |
| I-1025 | 3-I | H | Me |
| I-1026 | 3-I | H | OMe |
| I-1027 | 3-I | H | OEt |
| I-1031 | 3-I | H | CF₃ |
| I-1032 | 3-I | H | Cl |
| I-1033 | 3-I | 3-Me | OCH₂CH=CH₂ |
| I-1034 | 3-I | 3-Me | Me |
| I-1035 | 3-I | 3-Me | OMe |
| I-1036 | 3-I | 3-Me | OEt |
| I-1037 | 3-I | 3-Me | CF₃ |
| I-1041 | 3-I | 3-Me | Cl |
| I-1042 | 3-I | 3-OMe | OCH₂CH=CH₂ |
| I-1043 | 3-T | 3-OMe | Me |
| I-1044 | 3-I | 3-OMe | OMe |
| I-1045 | 3-I | 3-OMe | OEt |
| I-1046 | 3-I | 3-OMe | CF₃ |
| I-1047 | 3-I | 3-OMe | Cl |
| I-1051 | 3-I | 3-CF₃ | OCH₂CH=CH₂ |
| I-1052 | 3-I | 3-CF₃ | Me |
| I-1053 | 3-I | 3-CF₃ | OMe |
| I-1054 | 3-I | 3-CF₃ | OEt |
| I-1055 | 3-I | 37CF₃ | CF₃ |
| I-1056 | 3-I | 3-CF₃ | Cl |
| I-1057 | 3-I | 3-Cl | OCH₂CH=CH₂ |
| I-1061 | 3-I | 3-Cl | Me |
| I-1062 | 3-I | 3-Cl | OMe |
| I-1063 | 3-I | 3-Cl | OEt |
| I-1064 | 3-I | 3-Cl | CF₃ |
| I-1065 | 3-I | 3-Cl | Cl |
| I-1066 | 3-Me | H | Me |
| I-1067 | 3-Me | H | Et |
| I-1071 | 3-Me | H | OMe |
| I-1072 | 3-Me | H | OEt |
| I-1073 | 3-Me | H | SMe |
| I-1074 | 3-Me | H | SEt |
| I-1075 | 3-Me | H | CN |
| I-1076 | 3-Me | H | CF₃ |
| I-1077 | 3-Me | H | Cl |
| I-1081 | 3-Me | 3-Me | Me |
| I-1082 | 3-Me | 3-Me | Et |
| I-1083 | 3-Me | 3-Me | OMe |
| I-1084 | 3-Me | 3-Me | OEt |
| I-1085 | 3-Me | 3-Me | SMe |
| I-1086 | 3-Me | 3-Me | SEt |
| I-1087 | 3-Me | 3-Me | CN |
| I-1091 | 3-Me | 3-Me | CF₃ |
| I-1092 | 3-Me | 3-Me | Cl |
| I-1093 | 3-Me | 3-OMe | Me |
| I-1094 | 3-Me | 3-OMe | Et |
| I-1095 | 3-Me | 3-OMe | OMe |
| I-1096 | 3-Me | 3-OMe | OEt |
| I-1097 | 3-Me | 3-OMe | SMe |
| I-1101 | 3-Me | 3-OMe | SEt |
| I-1102 | 3-Me | 3-OMe | CN |
| I-1103 | 3-Me | 3-OMe | CF₃ |
| I-1104 | 3-Me | 3-OMe | Cl |
| I-1105 | 3-Me | 3-CF₃ | Me |
| I-1106 | 3-Me | 3-CF₃ | Et |
| I-1107 | 3-Me | 3-CF₃ | OMe |
| I-1111 | 3-Me | 3-CF₃ | OEt |
| I-1112 | 3-Me | 3-CF₃ | SMe |

TABLE 1-continued

| No. | $X_n$ | $Y_m$ | $R^1$ |
|---|---|---|---|
| I-1113 | 3-Me | 3-CF₃ | SEt |
| I-1114 | 3-Me | 3-CF₃ | CN |
| I-1115 | 3-Me | 3-CF₃ | CF₃ |
| I-1116 | 3-Me | 3-CF₃ | Cl |
| I-1117 | 3-Me | 3-Cl | Me |
| I-1121 | 3-Me | 3-Cl | Et |
| I-1122 | 3-Me | 3-Cl | OMe |
| I-1123 | 3-Me | 3-Cl | OEt |
| I-1124 | 3-Me | 3-Cl | SMe |
| I-1125 | 3-Me | 3-Cl | SEt |
| I-1126 | 3-Me | 3-Cl | CN |
| I-1127 | 3-Me | 3-Cl | CF₃ |
| I-1131 | 3-Me | 3-Cl | Cl |
| I-1132 | 3-OMe | H | Me |
| I-1133 | 3-OMe | H | Et |
| I-1134 | 3-OMe | H | OMe |
| I-1135 | 3-OMe | H | OEt |
| I-1136 | 3-OMe | H | SMe |
| I-1137 | 3-OMe | H | SEt |
| I-1141 | 3-OMe | H | CN |
| I-1142 | 3-OMe | H | CF₃ |
| I-1143 | 3-OMe | H | Cl |
| I-1144 | 3-OMe | 3-Me | Me |
| I-1145 | 3-OMe | 3-Me | Et |
| I-1146 | 3-OMe | 3-Me | OMe |
| I-1147 | 3-OMe | 3-Me | OEt |
| I-1151 | 3-OMe | 3-Me | SMe |
| I-1152 | 3-OMe | 3-Me | SEt |
| I-1153 | 3-OMe | 3-Me | CN |
| I-1154 | 3-OMe | 3-Me | CF₃ |
| I-1155 | 3-OMe | 3-Me | Cl |
| I-1156 | 3-OMe | 3-OMe | Me |
| I-1157 | 3-OMe | 3-OMe | Et |
| I-1161 | 3-OMe | 3-OMe | OMe |
| I-1162 | 3-OMe | 3-OMe | OEt |
| I-1163 | 3-OMe | 3-OMe | SMe |
| I-1164 | 3-OMe | 3-OMe | SEt |
| I-1165 | 3-OMe | 3-OMe | CN |
| I-1166 | 3-OMe | 3-OMe | CF₃ |
| I-1167 | 3-OMe | 3-OMe | Cl |
| I-1171 | 3-OMe | 3-CF₃ | Me |
| I-1172 | 3-OMe | 3-CF₃ | Et |
| I-1173 | 3-OMe | 3-CF₃ | OMe |
| I-1174 | 3-OMe | 3-CF₃ | OEt |
| I-1175 | 3-OMe | 3-CF₃ | SMe |
| I-1176 | 3-OMe | 3-CF₃ | SEt |
| I-1177 | 3-OMe | 3-CF₃ | CN |
| I-1181 | 3-OMe | 3-CF₃ | CF₃ |
| I-1182 | 3-OMe | 3-CF₃ | Cl |
| I-1183 | 3-OMe | 3-Cl | Me |
| I-1184 | 3-OMe | 3-Cl | Et |
| I-1185 | 3-OMe | 3-Cl | OMe |
| I-1186 | 3-OMe | 3-Cl | OEt |
| I-1187 | 3-OMe | 3-Cl | SMe |
| I-1191 | 3-OMe | 3-Cl | SEt |
| I-1192 | 3-OMe | 3-Cl | CN |
| I-1193 | 3-OMe | 3-Cl | CF₃ |
| I-1194 | 3-OMe | 3-Cl | Cl |
| I-1195 | 3-CF₃ | H | Me |
| I-1196 | 3-CF₃ | H | Et |
| I-1197 | 3-CF₃ | H | OMe |
| I-1201 | 3-CF₃ | H | OEt |
| I-1202 | 3-CF₃ | H | SMe |
| I-1203 | 3-CF₃ | H | SEt |
| I-1204 | 3-CF₃ | H | CN |
| I-1205 | 3-CF₃ | H | CF₃ |
| I-1206 | 3-CF₃ | H | Cl |
| I-1207 | 3-CF₃ | 3-Me | Me |
| I-1211 | 3-CF₃ | 3-Me | Et |
| I-1212 | 3-CF₃ | 3-Me | OMe |
| I-1213 | 3-CF₃ | 3-Me | OEt |
| I-1214 | 3-CF₃ | 3-Me | SMe |
| I-1215 | 3-CF₃ | 3-Me | SEt |
| I-1216 | 3-CF₃ | 3-Me | CN |
| I-1217 | 3-CF₃ | 3-Me | CF₃ |
| I-1221 | 3-CF₃ | 3-Me | Cl |
| I-1222 | 3-CF₃ | 3-OMe | Me |
| I-1223 | 3-CF₃ | 3-OMe | Et |
| I-1224 | 3-CF₃ | 3-OMe | OMe |
| I-1225 | 3-CF₃ | 3-OMe | OEt |
| I-1226 | 3-CF₃ | 3-OMe | SMe |
| I-1227 | 3-CF₃ | 3-OMe | SEt |
| I-1231 | 3-CF₃ | 3-OMe | CN |
| I-1232 | 3-CF₃ | 3-OMe | CF₃ |
| I-1233 | 3-CF₃ | 3-OMe | Cl |
| I-1234 | 3-CF₃ | 3-CF₃ | Me |
| I-1235 | 3-CF₃ | 3-CF₃ | Et |
| I-1236 | 3-CF₃ | 3-CF₃ | OMe |
| I-1237 | 3-CF₃ | 3-CF₃ | OEt |
| I-1241 | 3-CF₃ | 3-CF₃ | SMe |
| I-1242 | 3-CF₃ | 3-CF₃ | SEt |
| I-1243 | 3-CF₃ | 3-CF₃ | CN |
| I-1244 | 3-CF₃ | 3-CF₃ | CF₃ |
| I-1245 | 3-CF₃ | 3-CF₃ | Cl |
| I-1246 | 3-CF₃ | 3-Cl | Me |
| I-1247 | 3-CF₃ | 3-Cl | Et |
| I-1251 | 3-CF₃ | 3-Cl | OMe |
| I-1252 | 3-CF₃ | 3-Cl | OEt |
| I-1253 | 3-CF₃ | 3-Cl | SMe |
| I-1254 | 3-CF₃ | 3-Cl | SEt |
| I-1255 | 3-CF₃ | 3-Cl | CN |
| I-1256 | 3-CF₃ | 3-Cl | CF₃ |
| I-1257 | 3-CF₃ | 3-Cl | Cl |
| I-1261 | 3-Br | H | Me |
| I-1262 | 3-Br | H | Et |
| I-1263 | 3-Br | H | OMe |
| I-1264 | 3-Br | H | OEt |
| I-1265 | 3-Br | H | SMe |
| I-1266 | 3-Br | H | SEt |
| I-1267 | 3-Br | H | CN |
| I-1271 | 3-Br | H | CF₃ |
| I-1272 | 3-Br | H | Cl |
| I-1273 | 3-Br | 3-Me | Me |
| I-1274 | 3-Br | 3-Me | Et |
| I-1275 | 3-Br | 3-Me | OMe |
| I-1276 | 3-Br | 3-Me | OEt |
| I-1277 | 3-Br | 3-Me | SMe |
| I-1281 | 3-Br | 3-Me | SEt |
| I-1282 | 3-Br | 3-Me | CN |
| I-1283 | 3-Br | 3-Me | CF₃ |
| I-1284 | 3-Br | 3-Me | Cl |
| I-1285 | 3-Br | 3-OMe | Me |
| I-1286 | 3-Br | 3-OMe | Et |
| I-1287 | 3-Br | 3-OMe | OMe |
| I-1291 | 3-Br | 3-OMe | OEt |
| I-1292 | 3-Br | 3-OMe | SMe |
| I-1293 | 3-Br | 3-OMe | SEt |
| I-1294 | 3-Br | 3-OMe | CN |
| I-1295 | 3-Br | 3-OMe | CF₃ |
| I-1296 | 3-Br | 3-OMe | Cl |
| I-1297 | 3-Br | 3-CF₃ | Me |
| I-1301 | 3-Br | 3-CF₃ | Et |
| I-1302 | 3-Br | 3-CF₃ | OMe |
| I-1303 | 3-Br | 3-CF₃ | OEt |
| I-1304 | 3-Br | 3-CF₃ | SMe |
| I-1305 | 3-Br | 3-CF₃ | SEt |
| I-1306 | 3-Br | 3-CF₃ | CN |
| I-1307 | 3-Br | 3-CF₃ | CF₃ |
| I-1311 | 3-Br | 3-CF₃ | Cl |
| I-1312 | 3-Br | 3-Cl | Me |
| I-1313 | 3-Br | 3-Cl | Et |
| I-1314 | 3-Br | 3-Cl | OMe |
| I-1315 | 3-Br | 3-Cl | OEt |
| I-1316 | 3-Br | 3-Cl | SMe |
| I-1317 | 3-Br | 3-Cl | SEt |
| I-1321 | 3-Br | 3-Cl | CN |
| I-1322 | 3-Br | 3-Cl | CF₃ |
| I-1323 | 3-Br | 3-Cl | Cl |
| I-1324 | 3-Cl | H | Me |
| I-1325 | 3-Cl | H | Et |
| I-1326 | 3-Cl | H | OMe |
| I-1327 | 3-Cl | H | OEt |
| I-1331 | 3-Cl | H | SMe |
| I-1332 | 3-Cl | H | SEt |

TABLE 1-continued

| No. | $X_n$ | $Y_m$ | $R^1$ |
|---|---|---|---|
| I-1333 | 3-Cl | H | CN |
| I-1334 | 3-Cl | H | $CF_3$ |
| I-1335 | 3-Cl | H | Cl |
| I-1336 | 3-Cl | 3-Me | Me |
| I-1337 | 3-Cl | 3-Me | Et |
| I-1341 | 3-Cl | 3-Me | OMe |
| I-1342 | 3-Cl | 3-Me | OEt |
| I-1343 | 3-Cl | 3-Me | SMe |
| I-1344 | 3-Cl | 3-Me | SEt |
| I-1345 | 3-Cl | 3-Me | CN |
| I-1346 | 3-Cl | 3-Me | $CF_3$ |
| I-1347 | 3-Cl | 3-Me | Cl |
| I-1351 | 3-Cl | 3-OMe | Me |
| I-1352 | 3-Cl | 3-OMe | Et |
| I-1353 | 3-Cl | 3-OMe | OMe |
| I-1354 | 3-Cl | 3-OMe | OEt |
| I-1355 | 3-Cl | 3-OMe | SMe |
| I-1356 | 3-Cl | 3-OMe | SEt |
| I-1357 | 3-Cl | 3-OMe | CN |
| I-1361 | 3-Cl | 3-OMe | $CF_3$ |
| I-1362 | 3-Cl | 3-OMe | Cl |
| I-1363 | 3-Cl | 3-$CF_3$ | Me |
| I-1364 | 3-Cl | 3-$CF_3$ | Et |
| I-1365 | 3-Cl | 3-$CF_3$ | OMe |
| I-1366 | 3-Cl | 3-$CF_3$ | OEt |
| I-1367 | 3-Cl | 3-$CF_3$ | SMe |
| I-1371 | 3-Cl | 3-$CF_3$ | SEt |
| I-1372 | 3-Cl | 3-$CF_3$ | CN |
| I-1373 | 3-Cl | 3-$CF_3$ | $CF_3$ |
| I-1374 | 3-Cl | 3-$CF_3$ | Cl |
| I-1375 | 3-Cl | 3-Cl | Me |
| I-1376 | 3-Cl | 3-Cl | Et |
| I-1377 | 3-Cl | 3-Cl | OMe |
| I-1381 | 3-Cl | 3-Cl | OEt |
| I-1382 | 3-Cl | 3-Cl | SMe |
| I-1383 | 3-Cl | 3-Cl | SEt |
| I-1384 | 3-Cl | 3-Cl | CN |
| I-1385 | 3-Cl | 3-Cl | $CF_3$ |
| I-1386 | 3-Cl | 3-Cl | Cl |
| I-1387 | 3-F | H | Me |
| I-1391 | 3-F | H | Et |
| I-1392 | 3-F | H | OMe |
| I-1393 | 3-F | H | OEt |
| I-1394 | 3-F | H | SMe |
| I-1395 | 3-F | H | SEt |
| I-1396 | 3-F | H | CN |
| I-1397 | 3-F | H | $CF_3$ |
| I-1401 | 3-F | H | Cl |
| I-1402 | 3-F | 3-Me | Me |
| I-1403 | 3-F | 3-Me | Et |
| I-1404 | 3-F | 3-Me | OMe |
| I-1405 | 3-F | 3-Me | OEt |
| I-1406 | 3-F | 3-Me | SMe |
| I-1407 | 3-F | 3-Me | SEt |
| I-1411 | 3-F | 3-Me | CN |
| I-1412 | 3-F | 3-Me | $CF_3$ |
| I-1413 | 3-F | 3-Me | Cl |
| I-1414 | 3-F | 3-OMe | Me |
| I-1415 | 3-F | 3-OMe | Et |
| I-1416 | 3-F | 3-OMe | OMe |
| I-1417 | 3-F | 3-OMe | OEt |
| I-1421 | 3-F | 3-OMe | SMe |
| I-1422 | 3-F | 3-OMe | SEt |
| I-1423 | 3-F | 3-OMe | CN |
| I-1424 | 3-F | 3-OMe | $CF_3$ |
| I-1425 | 3-F | 3-OMe | Cl |
| I-1426 | 3-F | 3-$CF_3$ | Me |
| I-1427 | 3-F | 3-$CF_3$ | Et |
| I-1431 | 3-F | 3-$CF_3$ | OMe |
| I-1432 | 3-F | 3-$CF_3$ | OEt |
| I-1433 | 3-F | 3-$CF_3$ | SMe |
| I-1434 | 3-F | 3-$CF_3$ | SEt |
| I-1435 | 3-F | 3-$CF_3$ | CN |
| I-1436 | 3-F | 3-$CF_3$ | $CF_3$ |
| I-1437 | 3-F | 3-$CF_3$ | Cl |
| I-1441 | 3-F | 3-Cl | Me |
| I-1442 | 3-F | 3-Cl | Et |
| I-1443 | 3-F | 3-Cl | OMe |
| I-1444 | 3-F | 3-Cl | OEt |
| I-1445 | 3-F | 3-Cl | SMe |
| I-1446 | 3-F | 3-Cl | SEt |
| I-1447 | 3-F | 3-Cl | CN |
| I-1451 | 3-F | 3-Cl | $CF_3$ |
| I-1452 | 3-F | 3-Cl | Cl |
| I-1453 | 4-Me | H | Me |
| I-1454 | 4-Me | H | Et |
| I-1455 | 4-Me | H | OMe |
| I-1456 | 4-Me | H | OEt |
| I-1457 | 4-Me | H | SMe |
| I-1461 | 4-Me | H | SEt |
| I-1462 | 4-Me | H | CN |
| I-1463 | 4-Me | H | $CF_3$ |
| I-1464 | 4-Me | H | Cl |
| I-1465 | 4-Me | 3-Me | Me |
| I-1466 | 4-Me | 3-Me | Et |
| I-1467 | 4-Me | 3-Me | OMe |
| I-1471 | 4-Me | 3-Me | OEt |
| I-1472 | 4-Me | 3-Me | SMe |
| I-1473 | 4-Me | 3-Me | SEt |
| I-1474 | 4-Me | 3-Me | CN |
| I-1475 | 4-Me | 3-Me | $CF_3$ |
| I-1476 | 4-Me | 3-Me | Cl |
| I-1477 | 4-Me | 3-OMe | Me |
| I-1481 | 4-Me | 3-OMe | Et |
| I-1482 | 4-Me | 3-OMe | OMe |
| I-1483 | 4-Me | 3-OMe | OEt |
| I-1484 | 4-Me | 3-OMe | SMe |
| I-1485 | 4-Me | 3-OMe | SEt |
| I-1486 | 4-Me | 3-OMe | CN |
| I-1487 | 4-Me | 3-OMe | $CF_3$ |
| I-1491 | 4-Me | 3-OMe | Cl |
| I-1492 | 4-Me | 3-$CF_3$ | Me |
| I-1493 | 4-Me | 3-$CF_3$ | Et |
| I-1494 | 4-Me | 3-$CF_3$ | OMe |
| I-1495 | 4-Me | 3-$CF_3$ | OEt |
| I-1496 | 4-Me | 3-$CF_3$ | SMe |
| I-1497 | 4-Me | 3-$CF_3$ | SEt |
| I-1501 | 4-Me | 3-$CF_3$ | CN |
| I-1502 | 4-Me | 3-$CF_3$ | $CF_3$ |
| I-1503 | 4-Me | 3-$CF_3$ | Cl |
| I-1504 | 4-Me | 3-Cl | Me |
| I-1505 | 4-Me | 3-Cl | Et |
| I-1506 | 4-Me | 3-Cl | OMe |
| I-1507 | 4-Me | 3-Cl | OEt |
| I-1511 | 4-Me | 3-Cl | SMe |
| I-1512 | 4-Me | 3-Cl | SEt |
| I-1513 | 4-Me | 3-Cl | CN |
| I-1514 | 4-Me | 3-Cl | $CF_3$ |
| I-1515 | 4-Me | 3-Cl | Cl |
| I-1516 | 4-OMe | H | Me |
| I-1517 | 4-OMe | H | Et |
| I-1521 | 4-OMe | H | OMe |
| I-1522 | 4-OMe | H | OEt |
| I-1523 | 4-OMe | H | SMe |
| I-1524 | 4-OMe | H | SEt |
| I-1525 | 4-OMe | H | CN |
| I-1526 | 4-OMe | H | $CF_3$ |
| I-1527 | 4-OMe | H | Cl |
| I-1531 | 4-OMe | 3-Me | Me |
| I-1532 | 4-OMe | 3-Me | Et |
| I-1533 | 4-OMe | 3-Me | OMe |
| I-1534 | 4-OMe | 3-Me | OEt |
| I-1535 | 4-OMe | 3-Me | SMe |
| I-1536 | 4-OMe | 3-Me | SEt |
| I-1537 | 4-OMe | 3-Me | CN |
| I-1541 | 4-OMe | 3-Me | $CF_3$ |
| I-1542 | 4-OMe | 3-Me | Cl |
| I-1543 | 4-OMe | 3-OMe | Me |
| I-1544 | 4-OMe | 3-OMe | Et |
| I-1545 | 4-OMe | 3-OMe | OMe |
| I-1546 | 4-OMe | 3-OMe | OEt |
| I-1547 | 4-OMe | 3-OMe | SMe |
| I-1551 | 4-OMe | 3-OMe | SEt |
| I-1552 | 4-OMe | 3-OMe | CN |

TABLE 1-continued

| No. | $X_n$ | $Y_m$ | $R^1$ |
|---|---|---|---|
| I-1553 | 4-OMe | 3-OMe | $CF_3$ |
| I-1554 | 4-OMe | 3-OMe | Cl |
| I-1555 | 4-OMe | 3-$CF_3$ | Me |
| I-1556 | 4-OMe | 3-$CF_3$ | Et |
| I-1557 | 4-OMe | 3-$CF_3$ | OMe |
| I-1561 | 4-OMe | 3-$CF_3$ | OEt |
| I-1562 | 4-OMe | 3-$CF_3$ | SMe |
| I-1563 | 4-OMe | 3-$CF_3$ | SEt |
| I-1564 | 4-OMe | 3-$CF_3$ | CN |
| I-1565 | 4-OMe | 3-$CF_3$ | $CF_3$ |
| I-1566 | 4-OMe | 3-$CF_3$ | Cl |
| I-1567 | 4-OMe | 3-Cl | Me |
| I-1571 | 4-OMe | 3-Cl | Et |
| I-1572 | 4-OMe | 3-Cl | OMe |
| I-1573 | 4-OMe | 3-Cl | OEt |
| I-1574 | 4-OMe | 3-Cl | SMe |
| I-1575 | 4-OMe | 3-Cl | SEt |
| I-1576 | 4-OMe | 3-Cl | CN |
| I-1577 | 4-OMe | 3-Cl | $CF_3$ |
| I-1581 | 4-OMe | 3-Cl | Cl |
| I-1582 | 4-$CF_3$ | H | Me |
| I-1583 | 4-$CF_3$ | H | Et |
| I-1584 | 4-$CF_3$ | H | OMe |
| I-1585 | 4-$CF_3$ | H | OEt |
| I-1586 | 4-$CF_3$ | H | SMe |
| I-1587 | 4-$CF_3$ | H | SEt |
| I-1591 | 4-$CF_3$ | H | CN |
| I-1592 | 4-$CF_3$ | H | $CF_3$ |
| I-1593 | 4-$CF_3$ | H | Cl |
| I-1594 | 4-$CF_3$ | 3-Me | Me |
| I-1595 | 4-$CF_3$ | 3-Me | Et |
| I-1596 | 4-$CF_3$ | 3-Me | OMe |
| I-1597 | 4-$CF_3$ | 3-Me | OEt |
| I-1601 | 4-$CF_3$ | 3-Me | SMe |
| I-1602 | 4-$CF_3$ | 3-Me | SEt |
| I-1603 | 4-$CF_3$ | 3-Me | CN |
| I-1604 | 4-$CF_3$ | 3-Me | $CF_3$ |
| I-1605 | 4-$CF_3$ | 3-Me | Cl |
| I-1606 | 4-$CF_3$ | 3-OMe | Me |
| I-1607 | 4-$CF_3$ | 3-OMe | Et |
| I-1611 | 4-$CF_3$ | 3-OMe | OMe |
| I-1612 | 4-$CF_3$ | 3-OMe | OEt |
| I-1613 | 4-$CF_3$ | 3-OMe | SMe |
| I-1614 | 4-$CF_3$ | 3-OMe | SEt |
| I-1615 | 4-$CF_3$ | 3-OMe | CN |
| I-1616 | 4-$CF_3$ | 3-OMe | $CF_3$ |
| I-1617 | 4-$CF_3$ | 3-OMe | Cl |
| I-1621 | 4-$CF_3$ | 3-$CF_3$ | Me |
| I-1622 | 4-$CF_3$ | 3-$CF_3$ | Et |
| I-1623 | 4-$CF_3$ | 3-$CF_3$ | OMe |
| I-1624 | 4-$CF_3$ | 3-$CF_3$ | OEt |
| I-1625 | 4-$CF_3$ | 3-$CF_3$ | SMe |
| I-1626 | 4-$CF_3$ | 3-$CF_3$ | SEt |
| I-1627 | 4-$CF_3$ | 3-$CF_3$ | CN |
| I-1631 | 4-$CF_3$ | 3-$CF_3$ | $CF_3$ |
| I-1632 | 4-$CF_3$ | 3-$CF_3$ | Cl |
| I-1633 | 4-$CF_3$ | 3-Cl | Me |
| I-1634 | 4-$CF_3$ | 3-Cl | Et |
| I-1635 | 4-$CF_3$ | 3-Cl | OMe |
| I-1636 | 4-$CF_3$ | 3-Cl | OEt |
| I-1637 | 4-$CF_3$ | 3-Cl | SMe |
| I-1641 | 4-$CF_3$ | 3-Cl | SEt |
| I-1642 | 4-$CF_3$ | 3-Cl | CN |
| I-1643 | 4-$CF_3$ | 3-Cl | $CF_3$ |
| I-1644 | 4-$CF_3$ | 3-Cl | Cl |
| I-1645 | 4-Br | H | Me |
| I-1646 | 4-Br | H | Et |
| I-1647 | 4-Br | H | OMe |
| I-1651 | 4-Br | H | OEt |
| I-1652 | 4-Br | H | SMe |
| I-1653 | 4-Br | H | SEt |
| I-1654 | 4-Br | H | CN |
| I-1655 | 4-Br | H | $CF_3$ |
| I-1656 | 4-Br | H | Cl |
| I-1657 | 4-Br | 3-Me | Me |
| I-1661 | 4-Br | 3-Me | Et |
| I-1662 | 4-Br | 3-Me | OMe |
| I-1663 | 4-Br | 3-Me | OEt |
| I-1664 | 4-Br | 3-Me | SMe |
| I-1665 | 4-Br | 3-Me | SEt |
| I-1666 | 4-Br | 3-Me | CN |
| I-1667 | 4-Br | 3-Me | $CF_3$ |
| I-1671 | 4-Br | 3-Me | Cl |
| I-1672 | 4-Br | 3-OMe | Me |
| I-1673 | 4-Br | 3-OMe | Et |
| I-1674 | 4-Br | 3-OMe | OMe |
| I-1675 | 4-Br | 3-OMe | OEt |
| I-1676 | 4-Br | 3-OMe | SMe |
| I-1677 | 4-Br | 3-OMe | SEt |
| I-1681 | 4-Br | 3-OMe | CN |
| I-1682 | 4-Br | 3-OMe | $CF_3$ |
| I-1683 | 4-Br | 3-OMe | Cl |
| I-1684 | 4-Br | 3-$CF_3$ | Me |
| I-1685 | 4-Br | 3-$CF_3$ | Et |
| I-1686 | 4-Br | 3-$CF_3$ | OMe |
| I-1687 | 4-Br | 3-$CF_3$ | OEt |
| I-1692 | 4-Br | 3-$CF_3$ | SMe |
| I-1692 | 4-Br | 3-$CF_3$ | SEt |
| I-1693 | 4-Br | 3-$CF_3$ | CN |
| I-1694 | 4-Br | 3-$CF_3$ | $CF_3$ |
| I-1695 | 4-Br | 3-$CF_3$ | Cl |
| I-1696 | 4-Br | 3-Cl | Me |
| I-1697 | 4-Br | 3-Cl | Et |
| I-1701 | 4-Br | 3-Cl | OMe |
| I-1702 | 4-Br | 3-Cl | OEt |
| I-1703 | 4-Br | 3-Cl | SMe |
| I-1704 | 4-Br | 3-Cl | SEt |
| I-1705 | 4-Br | 3-Cl | CN |
| I-1706 | 4-Br | 3-Cl | $CF_3$ |
| I-1707 | 4-Br | 3-Cl | Cl |
| I-1711 | 4-Cl | H | Me |
| I-1712 | 4-Cl | H | Et |
| I-1713 | 4-Cl | H | OMe |
| I-1714 | 4-Cl | H | OEt |
| I-1715 | 4-Cl | H | SMe |
| I-1716 | 4-Cl | H | SEt |
| I-1717 | 4-Cl | H | CN |
| I-1721 | 4-Cl | H | $CF_3$ |
| I-1722 | 4-Cl | H | Cl |
| I-1723 | 4-Cl | 3-Me | Me |
| I-1724 | 4-Cl | 3-Me | Et |
| I-1725 | 4-Cl | 3-Me | OMe |
| I-1726 | 4-Cl | 3-Me | OEt |
| I-1727 | 4-Cl | 3-Me | SMe |
| I-1731 | 4-Cl | 3-Me | SEt |
| I-1732 | 4-Cl | 3-Me | CN |
| I-1733 | 4-Cl | 3-Me | $CF_3$ |
| I-1734 | 4-Cl | 3-Me | Cl |
| I-1735 | 4-Cl | 3-OMe | Me |
| I-1736 | 4-Cl | 3-OMe | Et |
| I-1737 | 4-Cl | 3-OMe | OMe |
| I-1741 | 4-Cl | 3-OMe | OEt |
| I-1742 | 4-Cl | 3-OMe | SMe |
| I-1743 | 4-Cl | 3-OMe | SEt |
| I-1744 | 4-Cl | 3-OMe | CN |
| I-1745 | 4-Cl | 3-OMe | $CF_3$ |
| I-1746 | 4-Cl | 3-OMe | Cl |
| I-1747 | 4-Cl | 3-$CF_3$ | Me |
| I-1751 | 4-Cl | 3-$CF_3$ | Et |
| I-1752 | 4-Cl | 3-$CF_3$ | OMe |
| I-1753 | 4-Cl | 3-$CF_3$ | OEt |
| I-1754 | 4-Cl | 3-$CF_3$ | SMe |
| I-1755 | 4-Cl | 3-$CF_3$ | SEt |
| I-1756 | 4-Cl | 3-$CF_3$ | CN |
| I-1757 | 4-Cl | 3-$CF_3$ | $CF_3$ |
| I-1761 | 4-Cl | 3-$CF_3$ | Cl |
| I-1762 | 4-Cl | 3-Cl | Me |
| I-1763 | 4-Cl | 3-Cl | Et |
| I-1764 | 4-Cl | 3-Cl | OMe |
| I-1765 | 4-Cl | 3-Cl | OEt |
| I-1766 | 4-Cl | 3-Cl | SMe |
| I-1767 | 4-Cl | 3-Cl | SEt |
| I-1771 | 4-Cl | 3-Cl | CN |
| I-1772 | 4-Cl | 3-Cl | $CF_3$ |

TABLE 1-continued

| No. | $X_n$ | $Y_m$ | $R^1$ |
|---|---|---|---|
| I-1773 | 4-Cl | 3-Cl | Cl |
| I-1774 | 4-F | H | Me |
| I-1775 | 4-F | H | Et |
| I-1776 | 4-F | H | OMe |
| I-1777 | 4-F | H | OEt |
| I-1781 | 4-F | H | SMe |
| I-1782 | 4-F | H | SEt |
| I-1783 | 4-F | H | CN |
| I-1784 | 4-F | H | $CF_3$ |
| I-1785 | 4-F | H | Cl |
| I-1786 | 4-F | 3-Me | Me |
| I-1787 | 4-F | 3-Me | Et |
| I-1791 | 4-F | 3-Me | OMe |
| I-1792 | 4-F | 3-Me | OEt |
| I-1793 | 4-F | 3-Me | SMe |
| I-1794 | 4-F | 3-Me | SEt |
| I-1795 | 4-F | 3-Me | CN |
| I-1796 | 4-F | 3-Me | $CF_3$ |
| I-1797 | 4-F | 3-Me | Cl |
| I-1801 | 4-F | 3-OMe | Me |
| I-1802 | 4-F | 3-OMe | Et |
| I-1803 | 4-F | 3-OMe | OMe |
| I-1804 | 4-F | 3-OMe | OEt |
| I-1805 | 4-F | 3-OMe | SMe |
| I-1806 | 4-F | 3-OMe | SEt |
| I-1807 | 4-F | 3-OMe | CN |
| I-1811 | 4-F | 3-OMe | $CF_3$ |
| I-1812 | 4-F | 3-OMe | Cl |
| I-1813 | 4-F | 3-$CF_3$ | Me |
| I-1814 | 4-F | 3-$CF_3$ | Et |
| I-1815 | 4-F | 3-$CF_3$ | OMe |
| I-1816 | 4-F | 3-$CF_3$ | OEt |
| I-1817 | 4-F | 3-$CF_3$ | SMe |
| I-1821 | 4-F | 3-$CF_3$ | SEt |
| I-1822 | 4-F | 3-$CF_3$ | CN |
| I-1823 | 4-F | 3-$CF_3$ | $CF_3$ |
| I-1824 | 4-F | 3-$CF_3$ | Cl |
| I-1825 | 4-F | 3-Cl | Me |
| I-1826 | 4-F | 3-Cl | Et |
| I-1827 | 4-F | 3-Cl | OMe |
| I-1831 | 4-F | 3-Cl | OEt |
| I-1832 | 4-F | 3-Cl | SMe |
| I-1833 | 4-F | 3-Cl | SEt |
| I-1834 | 4-F | 3-Cl | CN |
| I-1835 | 4-F | 3-Cl | $CF_3$ |
| I-1836 | 4-F | 3-Cl | Cl |
| I-1837 | 2,4-$(OMe)_2$ | H | Me |
| I-1841 | 2,4-$(OMe)_2$ | H | OMe |
| I-1842 | 2,4-$(OMe)_2$ | H | Cl |
| I-1843 | 2,4-$(OMe)_2$ | 3-Me | Me |
| I-1844 | 2,4-$(OMe)_2$ | 3-Me | OMe |
| I-1845 | 2,4-$(OMe)_2$ | 3-Me | Cl |
| I-1846 | 2,4-$(OMe)_2$ | 3-OMe | Me |
| I-1847 | 2,4-$(OMe)_2$ | 3-OMe | OMe |
| I-1851 | 2,4-$(OMe)_2$ | 3-OMe | Cl |
| I-1852 | 2,4-$(OMe)_2$ | 3-$CF_3$ | Me |
| I-1853 | 2,4-$(OMe)_2$ | 3-$CF_3$ | OMe |
| I-1854 | 2,4-$(OMe)_2$ | 3-$CF_3$ | Cl |
| I-1855 | 2,4-$(OMe)_2$ | 3-Cl | Me |
| I-1856 | 2,4-$(OMe)_2$ | 3-Cl | OMe |
| I-1857 | 2,4-$(OMe)_2$ | 3-Cl | Cl |
| I-1861 | 2,4-$Cl_2$ | H | Me |
| I-1862 | 2,4-$Cl_2$ | H | OMe |
| I-1863 | 2,4-$Cl_2$ | H | Cl |
| I-1864 | 2,4-$Cl_2$ | 3-Me | Me |
| I-1865 | 2,4-$Cl_2$ | 3-Me | OMe |
| I-1866 | 2,4-$Cl_2$ | 3-Me | Cl |
| I-1867 | 2,4-$Cl_2$ | 3-OMe | Me |
| I-1871 | 2,4-$Cl_2$ | 3-OMe | OMe |
| I-1872 | 2,4-$Cl_2$ | 3-OMe | Cl |
| I-1873 | 2,4-$Cl_2$ | 3-$CF_3$ | Me |
| I-1874 | 2,4-$Cl_2$ | 3-$CF_3$ | OMe |
| I-1875 | 2,4-$Cl_2$ | 3-$CF_3$ | Cl |
| I-1876 | 2,4-$Cl_2$ | 3-Cl | Me |
| I-1877 | 2,4-$Cl_2$ | 3-Cl | OMe |
| I-1881 | 2,4-$Cl_2$ | 3-Cl | Cl |
| I-1882 | 2,4-$F_2$ | H | Me |
| I-1883 | 2,4-$F_2$ | H | OMe |
| I-1884 | 2,4-$F_2$ | H | Cl |
| I-1885 | 2,4-$F_2$ | 3-Me | Me |
| I-1886 | 2,4-$F_2$ | 3-Me | OMe |
| I-1887 | 2,4-$F_2$ | 3-Me | Cl |
| I-1891 | 2,4-$F_2$ | 3-OMe | Me |
| I-1892 | 2,4-$F_2$ | 3-OMe | OMe |
| I-1893 | 2,4-$F_2$ | 3-OMe | Cl |
| I-1894 | 2,4-$F_2$ | 3-$CF_3$ | Me |
| I-1895 | 2,4-$F_2$ | 3-$CF_3$ | OMe |
| I-1896 | 2,4-$F_2$ | 3-$CF_3$ | Cl |
| I-1897 | 2,4-$F_2$ | 3-Cl | Me |
| I-1901 | 2,4-$F_2$ | 3-Cl | OMe |
| I-1902 | 3,4-$F_2$ | 3-Cl | Cl |
| I-1903 | 3,4-$Me_2$ | H | Me |
| I-1904 | 3,4-$Me_2$ | H | OMe |
| I-1905 | 3,4-$Me_2$ | H | Cl |
| I-1906 | 3,4-$Me_2$ | 3-Me | Me |
| I-1907 | 3,4-$Me_2$ | 3-Me | OMe |
| I-1911 | 3,4-$Me_2$ | 3-Me | Cl |
| I-1912 | 3,4-$Me_2$ | 3-OMe | Me |
| I-1913 | 3,4-$Me_2$ | 3-OMe | OMe |
| I-1914 | 3,4-$Me_2$ | 3-OMe | Cl |
| I-1915 | 3,4-$Me_2$ | 3-$CF_3$ | Me |
| I-1916 | 3,4-$Me_2$ | 3-$CF_3$ | OMe |
| I-1917 | 3,4-$Me_2$ | 3-$CF_3$ | Cl |
| I-1921 | 3,4-$Me_2$ | 3-Cl | Me |
| I-1922 | 3,4-$Me_2$ | 3-Cl | OMe |
| I-1923 | 3,4-$Me_2$ | 3-Cl | Cl |
| I-1924 | 3,4-$Cl_2$ | H | Me |
| I-1925 | 3,4-$Cl_2$ | H | OMe |
| I-1926 | 3,4-$Cl_2$ | H | Cl |
| I-1927 | 3,4-$Cl_2$ | 3-Me | Me |
| I-1931 | 3,4-$Cl_2$ | 3-Me | OMe |
| I-1932 | 3,4-$Cl_2$ | 3-Me | Cl |
| I-1933 | 3,4-$Cl_2$ | 3-OMe | Me |
| I-1934 | 3,4-$Cl_2$ | 3-OMe | OMe |
| I-1935 | 3,4-$Cl_2$ | 3-OMe | Cl |
| I-1936 | 3,4-$Cl_2$ | 3-$CF_3$ | Me |
| I-1937 | 3,4-$Cl_2$ | 3-$CF_3$ | OMe |
| I-1941 | 3,4-$Cl_2$ | 3-$CF_3$ | Cl |
| I-1942 | 3,4-$Cl_2$ | 3-Cl | Me |
| I-1943 | 3,4-$Cl_2$ | 3-Cl | OMe |
| I-1944 | 3,4-$Cl_2$ | 3-Cl | Cl |
| I-1945 | 3,4-$F_2$ | H | Me |
| I-1946 | 3,4-$F_2$ | H | OMe |
| I-1947 | 3,4-$F_2$ | H | Cl |
| I-1951 | 3,4-$F_2$ | 3-Me | Me |
| I-1952 | 3,4-$F_2$ | 3-Me | OMe |
| I-1953 | 3,4-$F_2$ | 3-Me | Cl |
| I-1954 | 3,4-$F_2$ | 3-OMe | Me |
| I-1955 | 3,4-$F_2$ | 3-OMe | OMe |
| I-1956 | 3,4-$F_2$ | 3-OMe | Cl |
| I-1957 | 3,4-$F_2$ | 3-$CF_3$ | Me |
| I-1961 | 3,4-$F_2$ | 3-$CF_3$ | OMe |
| I-1962 | 3,4-$F_2$ | 3-$CF_3$ | Cl |
| I-1963 | 3,4-$F_2$ | 3-Cl | Me |
| I-1964 | 3,4-$F_2$ | 3-Cl | OMe |
| I-1965 | 3,4-$F_2$ | 3-Cl | Cl |

The 2-benzyloxy-4-phenoxypyrimidine derivative represented by the formula (I) (Compound (I) as shown in Table 1 (1/34 to 34/34) can be synthesized in accordance with the following Reaction schemes I or II.

Reaction scheme I

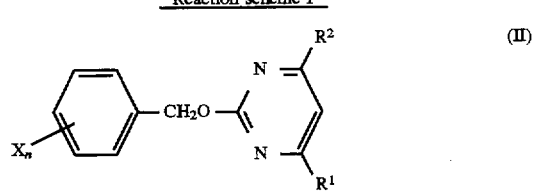

(II)

-continued
Reaction scheme I

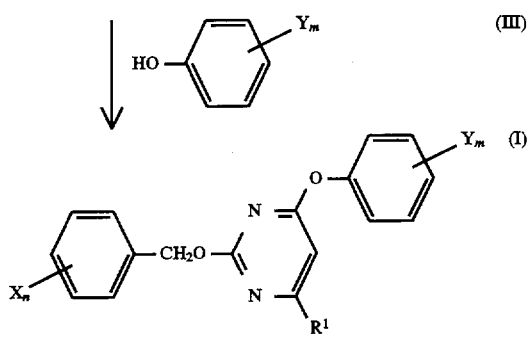

wherein $R^1$, $R^2$, X, Y n and m are as defined above.

Reaction scheme II

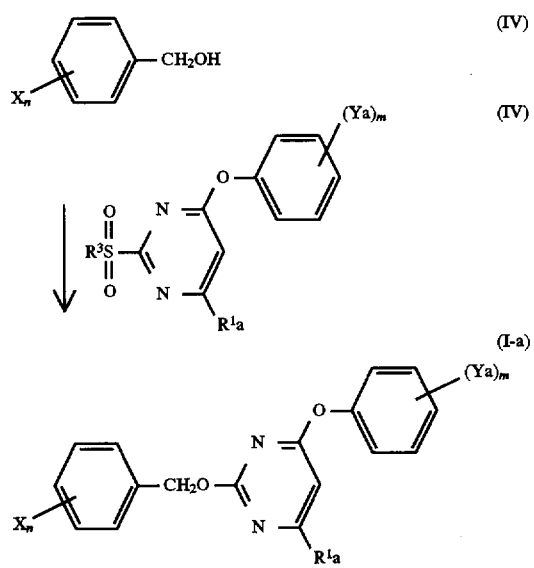

wherein $R^1a$, $R^3$, X, Ya, n and m are as defined above.

Either reaction shown by the above schemes is nucleophilic displacement on the pyrimidine ring, thus may be conducted in accordance with the following reaction sequence, for example.

Compounds (I) may be synthesized in a two-phase system containing a phase transfer catalyst such as amides (e.g. dimethylformamide, dimethylacetamide, and N-methyl-2-pyrrolidinone); ethers (e.g. diethylether, dimethoxyethane, diisopropylether, tetrahydrofuran, diglyme, and dioxane); and quaternary ammonium salts (e.g. benzalkonium chloride and tetrabutyl ammonium chloride), in the presence of a basic compound. The basic compound may be present during the nucleophilic displacement on the pyrimidine ring. The basic compound may be used to form a salt by substituting as proton, hydrogen bonded to oxygen of the phenol compound of the formula (III) or of the benzyl alcohol compound of the formula (IV). The reaction may be conducted preferably at a temperature range of −20° C. to 150° C., for a period of about 0.5 hour to one day (about 24 hours).

An iodide such as sodium iodide and potassium iodide or a crown ether such as 18-crown-6 and dibenzo-18-crown-6 may be added to the reaction system as a reaction accelerator.

Examples of the 2-benzyloxy-4(and/or 6)-halogenopyrimidine derivative of the formula (II) (Compound (II)) which can be used as a starting material in the Reaction scheme I are shown in Table 2.

TABLE 2

| No. | $X_n$ | $R^1$ | $R^2$ |
|---|---|---|---|
| II-1 | H | H | Cl |
| II-2 | H | $OCH_2CH=CH_2$ | Cl |
| II-3 | H | $OCH_2CH=CMe_2$ | Cl |
| II-4 | H | Me | Cl |
| II-5 | H | Et | Cl |
| II-6 | H | t-Bu | Cl |
| II-7 | H | OMe | Cl |
| II-11 | H | OEt | Cl |
| II-12 | H | OPr | Cl |
| II-13 | H | O-i-Pr | Cl |
| II-14 | H | OBu | Cl |
| II-15 | H | SMe | Cl |
| II-16 | H | SEt | Cl |
| II-17 | H | Ph | Cl |
| II-21 | H | CN | Cl |
| II-22 | H | $CF_3$ | Cl |
| II-23 | H | $OCH_2CF_3$ | Cl |
| II-24 | H | $SCH_2CF_3$ | Cl |
| II-25 | H | Br | Br |
| II-26 | H | Cl | Cl |
| II-27 | H | I | I |
| II-31 | 2-Me | $OCH_2CH=CH_2$ | Cl |
| II-32 | 2-Me | Me | Cl |
| II-33 | 2-Me | OMe | Cl |
| II-34 | 2-Me | OEt | Cl |
| II-35 | 2-Me | $CF_3$ | Cl |
| II-36 | 2-Me | Cl | Cl |
| II-37 | 2-OMe | $OCH_2CH=CH_2$ | Cl |
| II-41 | 2-OMe | Me | Cl |
| II-42 | 2-OMe | OMe | Cl |
| II-43 | 2-OMe | OEt | Cl |
| II-44 | 2-OMe | $CF_3$ | Cl |
| II-45 | 2-OMe | Cl | Cl |
| II-46 | 2-Br | $OCH_2CH=CH_2$ | Cl |
| II-47 | 2-Br | Me | Cl |
| II-51 | 2-Br | OMe | Cl |
| II-52 | 2-Br | OEt | Cl |
| II-53 | 2-Br | $CF_3$ | Cl |
| II-54 | 2-Br | Cl | Cl |
| II-55 | 2-Cl | $OCH_2CH=CH_2$ | Cl |
| II-56 | 2-Cl | Me | Cl |
| II-57 | 2-Cl | OMe | Cl |
| II-61 | 2-Cl | OEt | Cl |
| II-62 | 2-Cl | $CF_3$ | Cl |
| II-63 | 2-Cl | Cl | Cl |
| II-64 | 2-F | $OCH_2CH=CH_2$ | Cl |
| II-65 | 2-F | Me | Cl |
| II-66 | 2-F | OMe | Cl |
| II-67 | 2-F | OEt | Cl |
| II-71 | 2-F | $CF_3$ | Cl |
| II-72 | 2-F | Cl | Cl |
| II-73 | 3-I | $OCH_2CH=CH_2$ | Cl |
| II-74 | 3-I | Me | Cl |
| II-75 | 3-I | OMe | Cl |
| II-76 | 3-I | OEt | Cl |
| II-77 | 3-I | $CF_3$ | Cl |
| II-81 | 3-I | Cl | Cl |
| II-82 | 3-Me | Me | Cl |
| II-83 | 3-Me | Et | Cl |
| II-84 | 3-Me | OMe | Cl |
| II-85 | 3-Me | OEt | Cl |
| II-86 | 3-Me | SMe | Cl |
| II-87 | 3-Me | SEt | Cl |
| II-91 | 3-Me | CN | Cl |
| II-92 | 3-Me | $CF_3$ | Cl |
| II-93 | 3-Me | Cl | Cl |
| II-94 | 3-OMe | Me | Cl |
| II-95 | 3-OMe | Et | Cl |
| II-96 | 3-OMe | OMe | Cl |
| II-97 | 3-OMe | OEt | Cl |
| II-101 | 3-OMe | SMe | Cl |
| II-102 | 3-OMe | SEt | Cl |
| II-103 | 3-OMe | CN | Cl |
| II-104 | 3-OMe | $CF_3$ | Cl |

TABLE 2-continued

| No. | $X_n$ | $R^1$ | $R^2$ |
|---|---|---|---|
| II-105 | 3-OMe | Cl | Cl |
| II-106 | 3-CF$_3$ | Me | Cl |
| II-107 | 3-CF$_3$ | Et | Cl |
| II-111 | 3-CF$_3$ | OMe | Cl |
| II-112 | 3-CF$_3$ | OEt | Cl |
| II-113 | 3-CF$_3$ | SMe | Cl |
| II-114 | 3-CF$_3$ | SEt | Cl |
| II-115 | 3-CF$_3$ | CN | Cl |
| II-116 | 3-CF$_3$ | CF$_3$ | Cl |
| II-117 | 3-CF$_3$ | Cl | Cl |
| II-121 | 3-Br | Me | Cl |
| II-122 | 3-Br | Et | Cl |
| II-123 | 3-Br | OMe | Cl |
| II-124 | 3-Br | OEt | Cl |
| II-125 | 3-Br | SMe | Cl |
| II-126 | 3-Br | SEt | Cl |
| II-127 | 3-Br | CN | Cl |
| II-131 | 3-Br | CF$_3$ | Cl |
| II-132 | 3-Br | Cl | Cl |
| II-133 | 3-Cl | Me | Cl |
| II-134 | 3-Cl | Et | Cl |
| II-135 | 3-Cl | OMe | Cl |
| II-136 | 3-Cl | OEt | Cl |
| II-137 | 3-Cl | SMe | Cl |
| II-141 | 3-Cl | SEt | Cl |
| II-142 | 3-Cl | CN | Cl |
| II-143 | 3-Cl | CF$_3$ | Cl |
| II-144 | 3-Cl | Cl | Cl |
| II-145 | 3-F | Me | Cl |
| II-146 | 3-F | Et | Cl |
| II-147 | 3-F | OMe | Cl |
| II-151 | 3-F | OEt | Cl |
| II-152 | 3-F | SMe | Cl |
| II-153 | 3-F | SEt | Cl |
| II-154 | 3-F | CN | Cl |
| II-155 | 3-F | CF$_3$ | Cl |
| II-156 | 3-F | Cl | Cl |
| II-157 | 4-Me | Me | Cl |
| II-161 | 4-Me | Et | Cl |
| II-162 | 4-Me | OMe | Cl |
| II-163 | 4-Me | OEt | Cl |
| II-164 | 4-Me | SMe | Cl |
| II-165 | 4-Me | SEt | Cl |
| II-166 | 4-Me | CN | Cl |
| II-167 | 4-Me | CF$_3$ | Cl |
| II-171 | 4-Me | Cl | Cl |
| II-172 | 4-OMe | Me | Cl |
| II-173 | 4-OMe | Et | Cl |
| II-174 | 4-OMe | OMe | Cl |
| II-175 | 4-OMe | OEt | Cl |
| II-176 | 4-OMe | SMe | Cl |
| II-177 | 4-OMe | SEt | Cl |
| II-181 | 4-OMe | CN | Cl |
| II-182 | 4-OMe | CF$_3$ | Cl |
| II-183 | 4-OMe | Cl | Cl |
| II-184 | 4-CF$_3$ | Me | Cl |
| II-185 | 4-CF$_3$ | Et | Cl |
| II-186 | 4-CF$_3$ | OMe | Cl |
| II-187 | 4-CF$_3$ | OEt | Cl |
| II-191 | 4-CF$_3$ | SMe | Cl |
| II-192 | 4-CF$_3$ | SEt | Cl |
| II-193 | 4-CF$_3$ | CN | Cl |
| II-194 | 4-CF$_3$ | CF$_3$ | Cl |
| II-195 | 4-CF$_3$ | Cl | Cl |
| II-196 | 4-Br | Me | Cl |
| II-197 | 4-Br | Et | Cl |
| II-201 | 4-Br | OMe | Cl |
| II-202 | 4-Br | OEt | Cl |
| II-203 | 4-Br | SMe | Cl |
| II-204 | 4-Br | SEt | Cl |
| II-205 | 4-Br | CN | Cl |
| II-206 | 4-Br | CF$_3$ | Cl |
| II-207 | 4-Br | Cl | Cl |
| II-211 | 4-Cl | Me | Cl |
| II-212 | 4-Cl | Et | Cl |
| II-213 | 4-Cl | OMe | Cl |
| II-214 | 4-Cl | OEt | Cl |
| II-215 | 4-Cl | SMe | Cl |
| II-216 | 4-Cl | SEt | Cl |
| II-217 | 4-Cl | CN | Cl |
| II-221 | 4-Cl | CF$_3$ | Cl |
| II-222 | 4-Cl | Cl | Cl |
| II-223 | 4-F | Me | Cl |
| II-224 | 4-F | Et | Cl |
| II-225 | 4-F | OMe | Cl |
| II-226 | 4-F | OEt | Cl |
| II-227 | 4-F | SMe | Cl |
| II-231 | 4-F | SEt | Cl |
| II-232 | 4-F | CN | Cl |
| II-233 | 4-F | CF$_3$ | Cl |
| II-234 | 4-F | Cl | Cl |
| II-235 | 2,4-(OMe)$_2$ | Me | Cl |
| II-236 | 2,4-(OMe)$_2$ | OMe | Cl |
| II-237 | 2,4-(OMe)$_2$ | Cl | Cl |
| II-241 | 2,4-Cl$_2$ | Me | Cl |
| II-242 | 2,4-Cl$_2$ | OMe | Cl |
| II-243 | 2,4-Cl$_2$ | Cl | Cl |
| II-244 | 2,4-F$_2$ | Me | Cl |
| II-245 | 2,4-F$_2$ | OMe | Cl |
| II-246 | 2,4-F$_2$ | Cl | Cl |
| II-247 | 3,4-Me$_2$ | Me | Cl |
| II-251 | 3,4-Me$_2$ | OMe | Cl |
| II-252 | 3,4-Me$_2$ | Cl | Cl |
| II-253 | 3,4-Cl$_2$ | Me | Cl |
| II-254 | 3,4-Cl$_2$ | OMe | Cl |
| II-255 | 3,4-Cl$_2$ | Cl | Cl |
| II-256 | 3,4-F$_2$ | Me | Cl |
| II-257 | 3,4-F$_2$ | OMe | Cl |
| II-261 | 3,4-F$_2$ | Cl | Cl |

Among the compounds as shown in Table 2 (1/5 to 5/5), the 2-benzyloxy-4(or 6)-halogeno (or 4,6-dihalogeno) pyrimidine derivative of the formula (II-a) may be synthesized by substituting the moiety Z of the 2-(leaving-group-substituted)-4(or 6)-halogeno(or 4,6-dihalogeno)pyrimidine derivative of the formula (VIII) (Compound (VIII)) with the benzyl alcohol compound of the formula (IV) through nucleophilic displacement as shown in the Reaction scheme III.

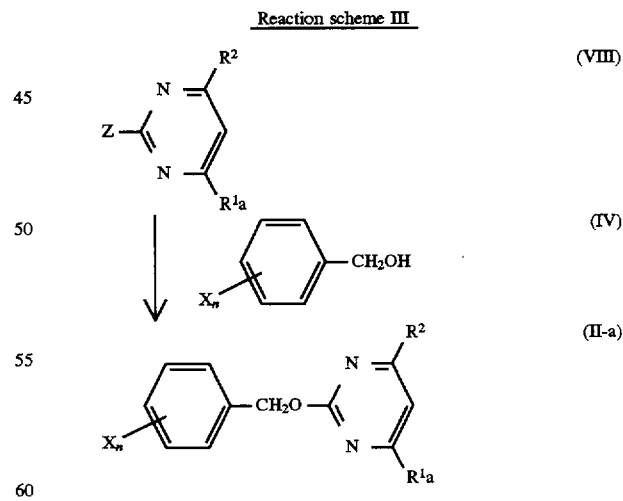

Reaction scheme III wherein $R^1$a, $R^2$, X and n are as defined above; and Z represents a halogen, $C_1$–$C_4$ alkylsulfonyl, $C_7$–$C_9$ aralkylsulfonyl, or arylsulfonyl (usually containing $C_6$–$C_7$, such as phenylsulfonyl and p-tolylsulfonyl).

The 2-benzyloxy-4(or 6)-halogeno-6(or 4)-(substituted thio)pyrimidine derivative of the formula (II-b1) is preferably synthesized by substituting a halogen of the 2-benzyloxy-4,6-dihalogenopyrimidine derivative of the formula (II-b2) with the thiol of the formula (X) through nucleophilic displacement in accordance with the Reaction scheme IV below.

Reaction scheme IV

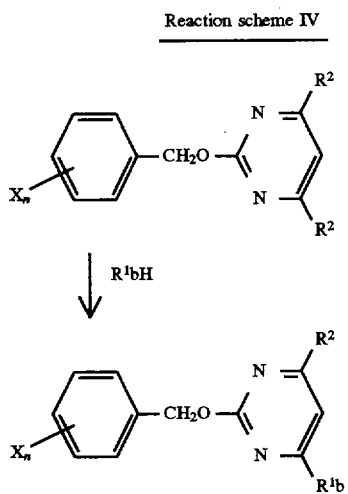

wherein $R^1b$ represents $C_1$–$C_4$ alkylthio or $C_1$–$C_4$ haloalkylthio; and $R^2$, X and n are as defined above.

Examples of Compound (VIII) which may be used as a starting material for Compound (II) are summarized in Table 3.

TABLE 3

| No. | $R^1a$ | $R^2$ | Z |
|---|---|---|---|
| VIII-1 | H | Cl | $MeSO_2$ |
| VIII-2 | $OCH_2CH=CH_2$ | Cl | $MeSO_2$ |
| VIII-3 | $OCH_2CH=CMe_2$ | Cl | $MeSO_2$ |
| VIII-4 | Me | Cl | $MeSO_2$ |
| VIII-5 | Et | Cl | $MeSO_2$ |
| VIII-6 | t-Bu | Cl | $MeSO_2$ |
| VIII-7 | OMe | Cl | $MeSO_2$ |
| VIII-8 | H | Cl | Cl |
| VIII-9 | Me | Cl | Cl |
| VIII-11 | OEt | Cl | $MeSO_2$ |
| VIII-12 | OPr | Cl | $MeSO_2$ |
| VIII-13 | O-i-Pr | Cl | $MeSO_2$ |
| VIII-14 | OBu | Cl | $MeSO_2$ |
| VIII-15 | Ph | Cl | $MeSO_2$ |
| VIII-16 | CN | Cl | $MeSO_2$ |
| VIII-17 | $CF_3$ | Cl | $MeSO_2$ |
| VIII-21 | $OCH_2CF_3$ | Cl | $MeSO_2$ |
| VIII-22 | Br | Br | $MeSO_2$ |
| VIII-23 | Cl | Cl | $MeSO_2$ |
| VIII-24 | I | I | $MeSO_2$ |
| VIII-25 | Cl | Cl | Cl |

Among the 2-(leaving-group-substituted)pyrimidine derivative of the formula (VIII) as shown in Table 3, the 2-(substituted sulfonyl)pyrimidine derivative of the formula (IX) wherein Z is bonded to the pyrimidine ring by sulfonyl group may be synthesized by oxidizing sulfur of the 2-(substituted thio)pyrimidine derivative of the formula (VII) in accordance with the Reaction scheme V.

Reaction scheme V

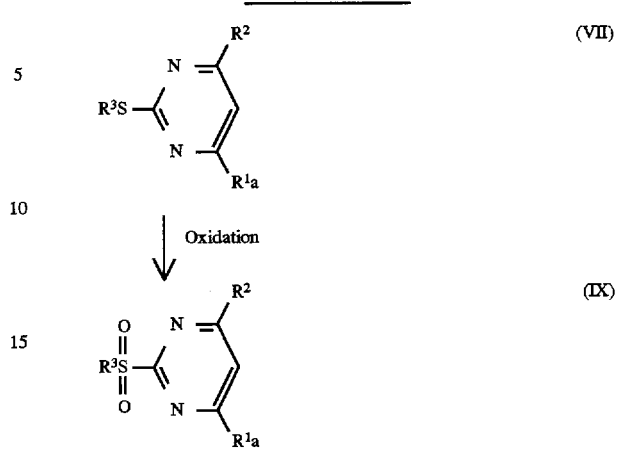

wherein $R^1a$, $R^2$, and $R^3$ are as defined above.

Examples of an oxidizing agent which may be suitably used for the oxidation as shown above are peracids, sodium hypochlorite, chlorine, potassium permanganate, and sodium tungstate.

The peracid is preferably selected from peracetic acid, perbenzoic acid, m-chloroperbenzoic acid and perphthalic acid.

The peracetic acid may optionally be in situ produced in a reaction vessel by adding hydrogen peroxide to acetic acid solution of Compound (VII).

The oxidation is generally conducted in the presence of a solvent and the solvent which may be used includes halogenated alkyls (e.g., dichloromethane and chloroform), esters, aromatic hydrocarbons, lower fatty acids and water. Depending on the oxidizing agents (e.g., chlorine), water should be used.

This oxidation may be carried out at from a temperature of 5° C. to the reflux point of the solvent (when a solvent is used).

More specifically, the oxidation may be conducted as described in the following:

Compounds (IX) (which are those corresponding to the Compounds Nos. VIII-1 to VIII-24 wherein Z represents $MeSO_2$) each may be synthesized as follows:

0.1 mol of each of compounds of the corresponding number (Nos. VII-1 to VII-24 in Table 4) and 300 ml of chloroform are stirred while cooling with iced water, then 0.2 mol of m-chloroperbenzoic acid is added thereto. The resulting solution is stirred for 2 hours at a temperature of 15° C. to 25° C.

The reaction mixture is partitioned by using aqueous saturated sodium hydrogen carbonate, and the organic layer is washed with aqueous saturated sodium chloride, then dried over anhydrous sodium sulfate.

Thereafter, the solvent is distilled off to afford a crude product, which is then purified on column chromatography to obtain the corresponding Compound (IX).

Alternatively, each of Compound Nos. VII-1 to VII-24 in an acetic acid solution may be oxidized by adding hydrogen peroxide thereto so as to produce peracetic acid in a reaction vessel, whereby corresponding Compound (IX) can be obtained. In such cases, reaction may be conducted preferably for a period of 2 to 4 hours at a temperature of 60° C. to 100° C.

TABLE 4

| No. | R¹a | R² | R³ |
|---|---|---|---|
| VII-1 | H | Cl | Me |
| VII-2 | OCH$_2$CH=CH$_2$ | Cl | Me |
| VII-3 | OCH$_2$CH=CMe$_2$ | Cl | Me |
| VII-4 | Me | Cl | Me |
| VII-5 | Et | Cl | Me |
| VII-6 | t-Bu | Cl | Me |
| VII-7 | OMe | Cl | Me |
| VII-11 | OEt | Cl | Me |
| VII-12 | OPr | Cl | Me |
| VII-13 | O-i-Pr | Cl | Me |
| VII-14 | OBu | Cl | Me |
| VII-15 | Ph | Cl | Me |
| VII-16 | CN | Cl | Me |
| VII-17 | CF$_3$ | Cl | Me |
| VII-21 | OCH$_2$CF$_3$ | Cl | Me |
| VII-22 | Br | Br | Me |
| VII-23 | Cl | Cl | Me |
| VII-24 | I | I | Me |

Among the 2-(substituted thio)pyrimidine derivative as shown in Table 4, 2-(substituted thio)-4,6-dihalogenopyrimidine derivatives can be synthesized by using the following process.

Process (a1): A malonic ester is cyclo-condensed with (S-substituted) isothiourea to obtain a 2-(substituted thio)-4,6-dihydroxypyrimidine derivative.

The same derivatives may be synthesized by the following process (a2) in place of the above process (a1).

Process (a2): A malonic ester is cyclo-condensed with thiourea to obtain 2-mercapto-4,6-dihydroxypyrimidine.

Then, the 2-mercapto group is converted to 2-(substituted thio) group in the presence of a basic compound. This process is suitable for the compound in which the substituent in the 2-(substituted thio) group is C$_1$–C$_4$ alkyl or C$_7$–C$_9$ aralkyl.

Each hydroxyl bonded to the positions 4 and 6 on the pyrimidine ring of the compound obtained by the process (a1) or (a2) is then converted to a halogen:

Process (b1): Hydroxyl is converted to a halogen by using phosphorus oxychloride (identical with phosphoryl chloride), phosphorus pentachloride, or phosphorus oxybromide (identical with phosphoryl bromide).

Further, chlorine at the position 4 and/or 6 may be converted to iodine through nucleophilic displacement by using potassium iodide or aqueous concentrated hydroiodic acid.

Compounds in which a substituent is ether-bonded to the position 4 and/or 6 on the pyrimidine ring can be synthesized as follows:

Process (c1): A halogen at the position 4 or 6 on the pyrimidine ring of the compound which is obtained from the process (b1) is etherified through nucleophilic displacement in the presence of a basic compound.

Process (d1): Either one of halogens at the positions 4 and 6 on the pyrimidine ring of the compound which is obtained from the process (b1) is converted to hydroxyl. Process (e1): Hydroxyl of the compound which is obtained from the process (d1) is etherified.

Among the 2-(substituted thio)pyrimidine derivatives of the formula (VII), those in which R¹ represents a substituent linked by carbon-carbon bond or hydrogen, and R² represents a halogen can be synthesized as follows:

Process (a3): A compound containing a 1,3-dicarbonyl group {one of the carbonyl groups is derived from carboxylic ester and the other is derived from formyl group (or acetal thereof) or acyl group (or ketal thereof)} may be cyclo-condensed with a (S-substituted) thiourea to obtain a 2-(substituted thio)-4(or 6)-hydroxypyrimidine derivative.

The same derivatives may be synthesized by the following process (a4) in place of the above process (a3).

Process (a4): A compound containing a 1,3-dicarbonyl group {one of the carbonyl groups is derived from carboxylic ester and the other is derived from formyl group (or acetal thereof) or acyl group (or ketal thereof)} may be cyclo-condensed with thiourea to obtain a 2-mercapto-4-(or 6)-hydroxypyrimidine derivative.

Then, 2-mercapto group is converted to 2-(substituted thio) group in the presence of a basic compound.

This process is suitable for the compounds in which the substituent in the 2-(substituted thio) group is C$_1$–C$_4$ alkyl or C$_7$–C$_9$ aralkyl.

Then, hydroxyl bonded to the position 4 or 6 on the pyrimidine ring of the compound obtained by the process (a3) or (a4) may be converted to a halogen:

Process (b2): Hydroxyl may be converted to a halogen by using phosphorus oxychloride (identical with phosphoryl chloride), phosphorus pentachloride, or phosphorus oxybromide (identical with phosphoryl bromide).

Synthesis processes may be more specifically described in the following.

Compounds which contain on the pyrimidine ring thereof, hydroxyl to be afterwards converted to chlorine or bromine and which are usable as starting materials for the production of Compound NOs. VII-1, VII-4, VII-5, VII-6, VII-15, VII-17, VII-22 and VII-23 can be synthesized by using the synthesis processes (a1) or (a3) in a manner described in the section (1) or section (2) below.

(1) 0.1 mol of methyl acetoacetate or methyl trifluoroacetoacetate, 0.1 mol of methylisothiourea sulfate (2-methyl-2-thiopseudourea sulfate) and 0.1 mol of sodium methoxide are reacted with one another in 500 ml of methyl alcohol at room temperature for overnight.

Then, the reaction mixture is cooled with iced water and 0.1 mol of hydrochloric acid is added thereto.

After insoluble matter is filtered off, the solvent is distilled off from the filtrate to afford a crude product, which may be then recrystallized to obtain a purified product.

(2) 0.1 mol of ethyl 3,3-diethoxypropionate, ethyl acetoacetate, ethyl propionylacetate, ethyl 2,2-dimethylpropionylacetate, ethyl benzoylacetate, ethyl trifluoroacetoacetate or diethyl malonate, 0.1 mol of methylisothiourea sulfate (2-methyl-2-thiopseudourea sulfate) and 0.1 mol of sodium ethoxide are reacted with one another in 500 ml of ethyl alcohol at reflux point for 4 hours.

The reaction mixture is allowed to cool to room temperature, and then, while further cooling with iced water, 0.1 mol of hydrochloric acid is added thereto.

After insoluble matter is filtered off, the solvent is distilled off from the filtrate to afford a crude product, which may be then recrystallized to obtain a purified product.

Each of the Compound Nos. VII-22 and VII-23 can be synthesized by using the process (b1).

50 ml of phosphorus oxychloride (identical with phosphoryl chloride) or phosphorus oxybromide (identical with phosphoryl bromide) is reacted with 0.1 mol of 4,6-dihydroxy-2-methylthiopyrimidine while stirring at a temperature of 70° C. to 80° C. for 7 hours.

Excess phosphorus oxychloride or phosphorus oxybromide is distilled off under reduced pressure from the reaction mixture.

The residue is redissolved in chloroform and washed successively with aqueous sodium hydrogen carbonate and water. After dried over sodium sulfate, the solvent is distilled off to afford a crude product, which may be then purified on column chromatography to obtain a purified product.

Compound No. VII-24 can be synthesized by heating the Compound No. VII-23 at about 70° C. for about 13 hours in the presence of an excessive amount of aqueous 57% hydroiodic acid.

Each of the Compounds Nos. VII-1, VII-4 to VII-6, VII-15 and VII-17 can be synthesized by using the process (b2).

0.1 mol of a compound containing on the pyrimidine ring hydroxyl to be afterwards converted to chlorine is reacted with 50 ml of phosphorus oxychloride while stirring at a temperature of 70° C. to 80° C. for 7 hours.

Excess phosphorus oxychloride is distilled off under reduced pressure from the reaction mixture.

The residue is redissolved in chloroform and washed successively with aqueous sodium hydrogen carbonate and water. After dried over sodium sulfate, the solvent is distilled off to afford a crude product, which may be then purified on column chromatography to obtain a purified product.

Each of the Compound Nos. VII-2, VII-3, VII-7, VII-11 to VII-14 and VII-21 can be synthesized by using the process (c1).

Compound Nos. VII-2 and VII-3 are prepared by nucleophilic substitution of one chlorine of Compound No. VII-23 with equimolar amounts of sodium 2-propenoxide and sodium 3-methyl-2-buten-1-oxide, respectively, in dimethylformamide at room temperature for overnight.

Compound Nos. VII-7 and VII-11 are prepared by nucleophilic substitution of one chlorine of Compound No. VII-23 with equimolar amounts of sodiumu methoxide and sodium ethoxide, respectively, in tetrahydrofuran at room temperature for 30 minites.

Compound Nos. VII-12 to VII-14 and VII-21 are prepared by nucleophilic substitution of one chlorine of Compound No. VII-23 with equimolar amounts of sodium propoxide, sodium butoxide, sodium 1-methylethoxide and sodium 2,2,2-trifluoroethoxide, respectively, in the corresponding alcohol at a temperature of 35° C. to 45° C. for 4 hours.

After the solvent and alcohol are distilled off from the reaction mixture under reduced pressure, ether is poured into the residue, and the mixture is washed with water and then dried over sodium sulfate.

Ether is distilled off to afford a crude product, which may then be purified on column chromatography to obtain a purified product.

Reaction temperature, reaction time and amounts of starting materials can be changed within the extent as described in the section (1) of the Reference synthesis example 1 set forth below.

Examples of the 2-(substituted sulfonyl)-4-phenoxypyrimidine derivative of the formula (V) useful as a starting material for the above reaction scheme II are shown in Table 5 (1/12 to 12/12).

TABLE 5

| NO. | $(Ya)_m$ | $R^1a$ | $R^3$ |
| --- | --- | --- | --- |
| V-1 | H | H | Me |
| V-2 | H | $OCH_2CH=CH_2$ | Me |
| V-3 | H | $OCH_2CH=CMe_2$ | Me |
| V-4 | H | Me | Me |
| V-5 | H | Et | Me |
| V-6 | H | t-Bu | Me |
| V-7 | H | OMe | Me |
| V-11 | H | OEt | Me |
| V-12 | H | OPr | Me |

TABLE 5-continued

| NO. | $(Ya)_m$ | $R^1a$ | $R^3$ |
| --- | --- | --- | --- |
| V-13 | H | O-i-Pr | Me |
| V-14 | H | OBu | Me |
| V-15 | H | Ph | Me |
| V-16 | H | CN | Me |
| V-17 | H | $CF_3$ | Me |
| V-21 | H | $OCH_2CF_3$ | Me |
| V-22 | H | Br | Me |
| V-23 | H | Cl | Me |
| V-24 | H | I | Me |
| V-25 | 2-Me | H | Me |
| V-26 | 2-Me | $OCH_2CH=CH_2$ | Me |
| V-27 | 2-Me | $OCH_2CH=CMe_2$ | Me |
| V-31 | 2-Me | Me | Me |
| V-32 | 2-Me | Et | Me |
| V-33 | 2-Me | t-Bu | Me |
| V-34 | 2-Me | OMe | Me |
| V-35 | 2-Me | OEt | Me |
| V-36 | 2-Me | OPr | Me |
| V-37 | 2-Me | O-i-Pr | Me |
| V-41 | 2-Me | OBu | Me |
| V-42 | 2-Me | Ph | Me |
| V-43 | 2-Me | CN | Me |
| V-44 | 2-Me | $CF_3$ | Me |
| V-45 | 2-Me | $OCH_2CF_3$ | Me |
| V-46 | 2-Me | Br | Me |
| V-47 | 2-Me | Cl | Me |
| V-51 | 2-Me | I | Me |
| V-52 | 2-OMe | H | Me |
| V-53 | 2-OMe | $OCH_2CH=CH_2$ | Me |
| V-54 | 2-OMe | $OCH_2CH=CMe_2$ | Me |
| V-55 | 2-OMe | Me | Me |
| V-56 | 2-OMe | Et | Me |
| V-57 | 2-OMe | t-Bu | Me |
| V-61 | 2-OMe | OMe | Me |
| V-62 | 2-OMe | OEt | Me |
| V-63 | 2-OMe | OPr | Me |
| V-64 | 2-OMe | O-i-Pr | Me |
| V-65 | 2-OMe | OBu | Me |
| V-66 | 2-OMe | Ph | Me |
| V-67 | 2-OMe | CN | Me |
| V-71 | 2-OMe | $CF_3$ | Me |
| V-72 | 2-OMe | $OCH_2CF_3$ | Me |
| V-73 | 2-OMe | Br | Me |
| V-74 | 2-OMe | Cl | Me |
| V-75 | 2-OMe | I | Me |
| V-76 | $2-CF_3$ | H | Me |
| V-77 | $2-CF_3$ | $OCH_2CH=CH_2$ | Me |
| V-81 | $2-CF_3$ | $OCH_2CH=CMe_2$ | Me |
| V-82 | $2-CF_3$ | Me | Me |
| V-83 | $2-CF_3$ | Et | Me |
| V-84 | $2-CF_3$ | t-Bu | Me |
| V-85 | 2-CF[00be] | OMe | Me |
| V-86 | $2-CF_3$ | OEt | Me |
| V-87 | $2-CF_3$ | OPr | Me |
| V-91 | $2-CF_3$ | O-i-Pr | Me |
| V-92 | $2-CF_3$ | OBu | Me |
| V-93 | $2-CF_3$ | Ph | Me |
| V-94 | $2-CF_3$ | CN | Me |
| V-95 | $2-CF_3$ | $CF_3$ | Me |
| V-96 | $2-CF_3$ | $OCH_2CF_3$ | Me |
| V-97 | $2-CF_3$ | Br | Me |
| V-101 | $2-CF_3$ | Cl | Me |
| V-102 | $2-CF_3$ | I | Me |
| V-103 | 2-Br | H | Me |
| V-104 | 2-Br | $OCH_2CH=CH_2$ | Me |
| V-105 | 2-Br | $OCH_2CH=CMe_2$ | Me |
| V-106 | 2-Br | Me | Me |
| V-107 | 2-Br | Et | Me |
| V-111 | 2-Br | t-Bu | Me |
| V-112 | 2-Br | OMe | Me |
| V-113 | 2-Br | OEt | Me |
| V-114 | 2-Br | OPr | Me |
| V-115 | 2-Br | O-i-Pr | Me |
| V-116 | 2-Br | OBu | Me |
| V-117 | 2-Br | Ph | Me |
| V-121 | 2-Br | CN | Me |
| V-122 | 2-Br | $CF_3$ | Me |

TABLE 5-continued

| NO. | (Ya)_m | R¹a | R³ |
|---|---|---|---|
| V-123 | 2-Br | OCH$_2$CF$_3$ | Me |
| V-124 | 2-Br | Br | Me |
| V-125 | 2-Br | Cl | Me |
| V-126 | 2-Br | I | Me |
| V-127 | 2-Cl | H | Me |
| V-131 | 2-Cl | OCH$_2$CH=CH$_2$ | Me |
| V-132 | 2-Cl | OCH$_2$CH=CMe$_2$ | Me |
| V-133 | 2-Cl | Me | Me |
| V-134 | 2-Cl | Et | Me |
| V-135 | 2-Cl | t-Bu | Me |
| V-136 | 2-Cl | OMe | Me |
| V-137 | 2-Cl | OEt | Me |
| V-141 | 2-Cl | OPr | Me |
| V-142 | 2-Cl | O-i-Pr | Me |
| V-143 | 2-Cl | OBu | Me |
| V-144 | 2-Cl | Ph | Me |
| V-145 | 2-Cl | CN | Me |
| V-146 | 2-Cl | CF$_3$ | Me |
| V-147 | 2-Cl | OCH$_2$CF$_3$ | Me |
| V-151 | 2-Cl | Br | Me |
| V-152 | 2-Cl | Cl | Me |
| V-153 | 2-Cl | I | Me |
| V-154 | 2-F | H | Me |
| V-155 | 2-F | OCH$_2$CH=CH$_2$ | Me |
| V-156 | 2-F | OCH$_2$CH=CMe$_2$ | Me |
| V-157 | 2-F | Me | Me |
| V-161 | 2-F | Et | Me |
| V-162 | 2-F | t-Bu | Me |
| V-163 | 2-F | OMe | Me |
| V-164 | 2-F | OEt | Me |
| V-165 | 2-F | OPr | Me |
| V-166 | 2-F | O-i-Pr | Me |
| V-167 | 2-F | OBu | Me |
| V-171 | 2-F | Ph | Me |
| V-172 | 2-F | CN | Me |
| V-173 | 2-F | CF$_3$ | Me |
| V-174 | 2-F | OCH$_2$CF$_3$ | Me |
| V-175 | 2-F | Br | Me |
| V-176 | 2-F | Cl | Me |
| V-177 | 2-F | I | Me |
| V-181 | 3-Me | H | Me |
| V-182 | 3-Me | OCH$_2$CH=CH$_2$ | Me |
| V-183 | 3-Me | OCH$_2$CH=CMe$_2$ | Me |
| V-184 | 3-Me | Me | Me |
| V-185 | 3-Me | Et | Me |
| V-186 | 3-Me | t-Bu | Me |
| V-187 | 3-Me | OMe | Me |
| V-191 | 3-Me | OEt | Me |
| V-192 | 3-Me | OPr | Me |
| V-193 | 3-Me | O-i-Pr | Me |
| V-194 | 3-Me | OBu | Me |
| V-195 | 3-Me | Ph | Me |
| V-196 | 3-Me | CN | Me |
| V-197 | 3-Me | CF$_3$ | Me |
| V-201 | 3-Me | OCH$_2$CF$_3$ | Me |
| V-202 | 3-Me | Br | Me |
| V-203 | 3-Me | Cl | Me |
| V-204 | 3-Me | I | Me |
| V-205 | 3-OMe | H | Me |
| V-206 | 3-OMe | OCH$_2$CH=CH$_2$ | Me |
| V-207 | 3-OMe | OCH$_2$CH=CMe$_2$ | Me |
| V-211 | 3-OMe | Me | Me |
| Y-212 | 3-OMe | Et | Me |
| V-213 | 3-OMe | t-Bu | Me |
| V-214 | 3-OMe | OMe | Me |
| V-215 | 3-OMe | OEt | Me |
| V-216 | 3-OMe | OPr | Me |
| V-217 | 3-OMe | O-i-Pr | Me |
| V-221 | 3-OMe | OBu | Me |
| V-222 | 3-OMe | Ph | Me |
| V-223 | 3-OMe | CN | Me |
| V-224 | 3-OMe | CF$_3$ | Me |
| V-225 | 3-OMe | OCH$_2$CF$_3$ | Me |
| V-226 | 3-OMe | Br | Me |
| V-227 | 3-OMe | Cl | Me |
| V-231 | 3-OMe | I | Me |
| V-232 | 3-CF$_3$ | H | Me |
| V-233 | 3-CF$_3$ | OCH$_2$CF$_3$ | Me |
| V-234 | 3-CF$_3$ | OCH$_2$CH=CH$_2$ | Me |
| V-235 | 3-CF$_3$ | OCH$_2$CH=CMe$_2$ | Me |
| V-236 | 3-CF$_3$ | Me | Me |
| V-237 | 3-CF$_3$ | Et | Me |
| V-241 | 3-CF$_3$ | t-Bu | Me |
| V-242 | 3-CF$_3$ | OMe | Me |
| V-243 | 3-CF$_3$ | OEt | Me |
| V-244 | 3-CF$_3$ | OPr | Me |
| V-245 | 3-CF$_3$ | O-i-Pr | Me |
| V-246 | 3-CF$_3$ | OBu | Me |
| V-247 | 3-CF$_3$ | Ph | Me |
| V-251 | 3-CF$_3$ | CN | Me |
| V-252 | 3-CF$_3$ | CF$_3$ | Me |
| V-253 | 3-CF$_3$ | OCH$_2$CF$_3$ | Me |
| V-254 | 3-CF$_3$ | Br | Me |
| V-255 | 3-CF$_3$ | Cl | Me |
| V-256 | 3-CF$_3$ | I | Me |
| V-257 | 3-OCF$_3$ | H | Me |
| V-261 | 3-OCF$_3$ | OCH$_2$CH=CH$_2$ | Me |
| V-262 | 3-OCF$_3$ | OCH$_2$CH=CMe$_2$ | Me |
| V-263 | 3-OCF$_3$ | Me | Me |
| V-264 | 3-OCF$_3$ | Et | Me |
| V-265 | 3-OCF$_3$ | t-Bu | Me |
| V-266 | 3-OCF$_3$ | OMe | Me |
| V-267 | 3-OCF$_3$ | OEt | Me |
| V-271 | 3-OCF$_3$ | OPr | Me |
| V-272 | 3-OCF$_3$ | O-i-Pr | Me |
| V-273 | 3-OCF$_3$ | OBu | Me |
| V-274 | 3-OCF$_3$ | Fh | Me |
| V-275 | 3-OCF$_3$ | CN | Me |
| V-276 | 3-OCF$_3$ | CF$_3$ | Me |
| V-277 | 3-OCF$_3$ | OCH$_2$CF$_3$ | Me |
| V-281 | 3-OCF$_3$ | Br | Me |
| V-282 | 3-OCF$_3$ | Cl | Me |
| V-283 | 3-Br | I | Me |
| V-284 | 3-Br | H | Me |
| V-285 | 3-Br | OCH$_2$CH=CH$_2$ | Me |
| V-286 | 3-Br | OCH$_2$CH=CMe$_2$ | Me |
| V-287 | 3-Br | Me | Me |
| V-291 | 3-Br | Et | Me |
| V-292 | 3-Br | t-Bu | Me |
| V-293 | 3-Br | OMe | Me |
| V-294 | 3-Br | OEt | Me |
| V-295 | 3-Br | OPr | Me |
| V-296 | 3-Br | O-i-Pr | Me |
| V-297 | 3-Br | OBu | Me |
| V-301 | 3-Br | Ph | Me |
| V-302 | 3-Br | CN | Me |
| V-303 | 3-Br | CF$_3$ | Me |
| V-304 | 3-Br | OCH$_2$CF$_3$ | Me |
| V-305 | 3-Br | Br | Me |
| V-306 | 3-Br | Cl | Me |
| V-307 | 3-Cl | I | Me |
| V-311 | 3-Cl | H | Me |
| V-312 | 3-Cl | OCH$_2$CH=CH$_2$ | Me |
| V-313 | 3-Cl | OCH$_2$CH=CMe$_2$ | Me |
| V-314 | 3-Cl | Me | Me |
| V-315 | 3-Cl | Et | Me |
| V-316 | 3-Cl | t-Bu | Me |
| V-317 | 3-Cl | OMe | Me |
| V-321 | 3-Cl | OEt | Me |
| V-322 | 3-Cl | OPr | Me |
| V-323 | 3-Cl | O-i-Pr | Me |
| V-324 | 3-Cl | OBu | Me |
| V-325 | 3-Cl | Ph | Me |
| V-326 | 3-Cl | CN | Me |
| V-327 | 3-Cl | CF$_3$ | Me |
| V-331 | 3-Cl | OCH$_2$CF$_3$ | Me |
| V-332 | 3-Cl | Br | Me |
| V-333 | 3-Cl | Cl | Me |
| V-334 | 3-F | I | Me |
| V-335 | 3-F | H | Me |
| V-336 | 3-F | OCH$_2$CH=CH$_2$ | Me |
| V-337 | 3-F | OCH$_2$CH=CMe$_2$ | Me |
| V-341 | 3-F | Me | Me |
| V-342 | 3-F | Et | Me |

TABLE 5-continued

| NO. | (Ya)$_m$ | R$^1$a | R$^3$ |
|---|---|---|---|
| V-343 | 3-F | OMe | Me |
| V-344 | 3-F | OEt | Me |
| V-345 | 3-F | OPr | Me |
| V-346 | 3-F | O-i-Pr | Me |
| V-347 | 3-F | OBu | Me |
| V-351 | 3-F | Ph | Me |
| V-352 | 3-F | CN | Me |
| V-353 | 3-F | CF$_3$ | Me |
| V-354 | 3-F | OCH$_2$CF$_3$ | Me |
| V-355 | 3-F | Br | Me |
| V-356 | 3-F | Cl | Me |
| V-357 | 3-F | I | Me |
| V-361 | 3-I | H | Me |
| V-362 | 3-I | OCH$_2$CH=CH$_2$ | Me |
| V-363 | 3-I | OCH$_2$CH=OMe$_2$ | Me |
| V-364 | 3-I | Me | Me |
| V-365 | 3-I | Et | Me |
| V-366 | 3-I | t-Bu | Me |
| V-367 | 3-I | OMe | Me |
| V-371 | 3-I | OEt | Me |
| V-372 | 3-I | OPr | Me |
| V-373 | 3-I | O-i-Pr | Me |
| V-374 | 3-I | OBu | Me |
| V-375 | 3-I | Ph | Me |
| V-376 | 3-I | CN | Me |
| V-377 | 3-I | CF$_3$ | Me |
| V-381 | 3-I | OCH$_2$CF$_3$ | Me |
| V-382 | 3-I | Br | Me |
| V-383 | 3-I | Cl | Me |
| V-384 | 3-I | I | Me |
| V-385 | 4-Me | H | Me |
| V-386 | 4-Me | OCH$_2$CH=CH$_2$ | Me |
| V-387 | 4-Me | OCH$_2$CH=CMe$_2$ | Me |
| V-391 | 4-Me | Me | Me |
| V-392 | 4-Me | Et | Me |
| V-393 | 4-Me | t-Bu | Me |
| V-394 | 4-Me | OMe | Me |
| V-395 | 4-Me | OEt | Me |
| V-396 | 4-Me | OPr | Me |
| V-397 | 4-Me | O-i-Pr | Me |
| V-401 | 4-Me | OBu | Me |
| V-402 | 4-Me | Ph | Me |
| V-403 | 4-Me | CN | Me |
| V-404 | 4-Me | CF$_3$ | Me |
| V-405 | 4-Me | OCH$_2$CF$_3$ | Me |
| V-406 | 4-Me | Br | Me |
| V-407 | 4-Me | Cl | Me |
| V-411 | 4-Me | I | Me |
| V-412 | 4-OMe | H | Me |
| V-413 | 4-OMe | OCH$_2$CH=CH$_2$ | Me |
| V-414 | 4-OMe | OCH$_2$CH=CMe$_2$ | Me |
| V-415 | 4-OMe | Me | Me |
| V-416 | 4-OMe | Et | Me |
| V-417 | 4-OMe | t-Bu | Me |
| V-421 | 4-OMe | OMe | Me |
| V-422 | 4-OMe | OEt | Me |
| V-423 | 4-OMe | OPr | Me |
| V-424 | 4-OMe | O-i-Pr | Me |
| V-425 | 4-OMe | OBu | Me |
| V-426 | 4-OMe | Ph | Me |
| V-427 | 4-OMe | CN | Me |
| V-431 | 4-OMe | CF$_3$ | Me |
| V-432 | 4-OMe | OCH$_2$CF$_3$ | Me |
| V-433 | 4-OMe | Br | Me |
| V-434 | 4-OMe | Cl | Me |
| V-435 | 4-OMe | I | Me |
| V-436 | 4-CF$_3$ | H | Me |
| V-437 | 4-CF$_3$ | OCH$_2$CH=CH$_2$ | Me |
| V-441 | 4-CF$_3$ | OCH$_2$CH=CMe$_2$ | Me |
| V-442 | 4-CF$_3$ | Me | Me |
| V-443 | 4-CF$_3$ | Et | Me |
| V-444 | 4-CF$_3$ | t-Bu | Me |
| V-445 | 4-CF$_3$ | OMe | Me |
| V-446 | 4-CF$_3$ | OEt | Me |
| V-447 | 4-CF$_3$ | OPr | Me |
| V-451 | 4-CF$_3$ | O-i-Pr | Me |
| V-452 | 4-CF$_3$ | OBu | Me |
| V-453 | 4-CF$_3$ | Ph | Me |
| V-454 | 4-CF$_3$ | CN | Me |
| V-455 | 4-CF$_3$ | CF$_3$ | Me |
| V-456 | 4-CF$_3$ | OCH$_2$CF$_3$ | Me |
| V-457 | 4-CF$_3$ | Br | Me |
| V-461 | 4-CF$_3$ | Cl | Me |
| V-462 | 4-CF$_3$ | I | Me |
| V-463 | 4-OCF$_3$ | H | Me |
| V-464 | 4-OCF$_3$ | OCH$_2$CH=CH$_2$ | Me |
| V-465 | 4-OCF$_3$ | OCH$_2$CH=CMe$_2$ | Me |
| V-466 | 4-OCF$_3$ | Me | Me |
| V-467 | 4-OCF$_3$ | Et | Me |
| V-471 | 4-OCF$_3$ | t-Bu | Me |
| V-472 | 4-OCF$_3$ | OMe | Me |
| V-473 | 4-OCF$_3$ | OEt | Me |
| V-474 | 4-OCF$_3$ | OPr | Me |
| V-475 | 4-OCF$_3$ | O-i-Pr | Me |
| V-476 | 4-OCF$_3$ | OBu | Me |
| V-477 | 4-OCF$_3$ | Ph | Me |
| V-481 | 4-OCF$_3$ | CN | Me |
| V-482 | 4-OCF$_3$ | CF$_3$ | Me |
| V-483 | 4-OCF$_3$ | OCH$_2$CF$_3$ | Me |
| V-484 | 4-OCF$_3$ | Br | Me |
| V-485 | 4-OCF$_3$ | Cl | Me |
| V-486 | 4-OCF$_3$ | I | Me |
| V-487 | 4-Br | H | Me |
| V-491 | 4-Br | OCH$_2$CH=CH$_2$ | Me |
| V-492 | 4-Br | OCH$_2$CH=CMe$_2$ | Me |
| V-493 | 4-Br | Me | Me |
| V-494 | 4-Br | Et | Me |
| V-495 | 4-Br | t-Bu | Me |
| V-496 | 4-Br | OMe | Me |
| V-497 | 4-Br | OEt | Me |
| V-501 | 4-Br | OPr | Me |
| V-502 | 4-Br | O-i-Pr | Me |
| V-503 | 4-Br | OBu | Me |
| V-504 | 4-Br | Ph | Me |
| V-505 | 4-Br | CN | Me |
| V-506 | 4-Br | CF$_3$ | Me |
| V-507 | 4-Br | OCH$_2$CF$_3$ | Me |
| V-511 | 4-Br | Br | Me |
| V-512 | 4-Br | Cl | Me |
| V-513 | 4-Br | I | Me |
| V-514 | 4-Cl | H | Me |
| V-515 | 4-Cl | OCH$_2$CH=CH$_2$ | Me |
| V-516 | 4-Cl | OCH$_2$CH=CMe$_2$ | Me |
| V-517 | 4-Cl | Me | Me |
| V-521 | 4-Cl | Et | Me |
| V-522 | 4-Cl | t-Bu | Me |
| V-523 | 4-Cl | OMe | Me |
| V-524 | 4-Cl | bEt | Me |
| V-525 | 4-Cl | OPr | Me |
| V-526 | 4-Cl | O-i-Pr | Me |
| V-527 | 4-Cl | OBu | Me |
| V-531 | 4-Cl | Ph | Me |
| V-532 | 4-Cl | CN | Me |
| V-533 | 4-Cl | CF$_3$ | Me |
| V-534 | 4-Cl | OCH$_2$CE3 | Me |
| V-535 | 4-Cl | Br | Me |
| V-536 | 4-Cl | Cl | Me |
| V-537 | 4-Cl | I | Me |
| V-541 | 4-F | H | Me |
| V-542 | 4-F | OCH$_2$CH=CH$_2$ | Me |
| V-543 | 4-F | OCH$_2$CH=CMe$_2$ | Me |
| V-544 | 4-F | Me | Me |
| V-545 | 4-F | Et | Me |
| V-546 | 4-F | t-Bu | Me |
| V-547 | 4-F | OMe | Me |
| V-551 | 4-F | OEt | Me |
| V-552 | 4-F | OPr | Me |
| V-553 | 4-F | O-i-Pr | Me |
| V-554 | 4-F | OBu | Me |
| V-555 | 4-F | Fh | Me |
| V-556 | 4-F | CN | Me |
| V-557 | 4-F | CF$_3$ | Me |
| V-561 | 4-F | OCH$_2$CF$_3$ | Me |
| V-562 | 4-F | Br | Me |

TABLE 5-continued

| NO. | (Ya)$_m$ | R$^1$a | R$^3$ |
|---|---|---|---|
| V-563 | 4-F | Cl | Me |
| V-564 | 4-F | I | Me |
| V-565 | 4-I | H | Me |
| V-566 | 4-I | OCH$_2$CH=CH$_2$ | Me |
| V-567 | 4-I | OCH$_2$CH=CMe$_2$ | Me |
| V-571 | 4-I | Me | Me |
| V-572 | 4-I | Et | Me |
| V-573 | 4-I | t-Bu | Me |
| V-574 | 4-I | OMe | Me |
| V-575 | 4-I | OEt | Me |
| V-576 | 4-I | OPr | Me |
| V-577 | 4-I | O-i-Pr | Me |
| V-581 | 4-I | OBu | Me |
| V-582 | 4-I | Ph | Me |
| V-583 | 4-I | CN | Me |
| V-584 | 4-I | CF$_3$ | Me |
| V-585 | 4-I | OCH$_2$CF$_3$ | Me |
| V-586 | 4-I | Br | Me |
| V-587 | 4-I | Cl | Me |
| V-591 | 4-I | I | Me |

As shown by the following Reaction scheme VI, the 2-(substituted sulfonyl)-4-phenoxypyrimidine derivative of the formula (V) can be synthesized by oxidizing sulfur of the 2-(substituted thio)-4-phenoxypyrimidine derivative of the formula (VI).

Reaction scheme VI

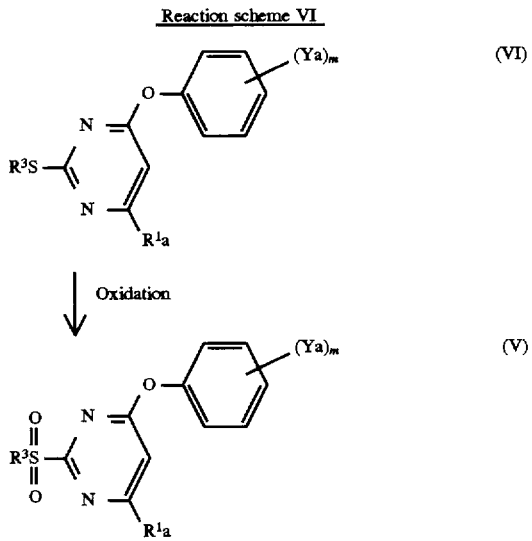

wherein R$^1$a, R$^3$, Ya and m are as defined above.

This oxidation may be conducted under the same reaction conditions (solvent, oxidizing reagent, temperature and reaction time) as those described about the Reaction scheme V by which sulfur of the 2-(substituted thio)pyrimidine derivative of the formula (VII) is oxidized to obtain the 2-(substituted sulfonyl)pyrimidine derivative of the formula (IX).

The 2-(substituted thio)-4-phenoxypyrimidine derivative of the formula (VI) useful as a starting material for the above oxidation can be synthesized by substituting a halogen at the position 4 or 6 of the 2-(substituted)pyrimidine derivative of the formula (VII) with a phenol compound of the formula (III-a) through nucleophilic displacement, as shown in the following Reaction scheme VII.

Reaction scheme VII

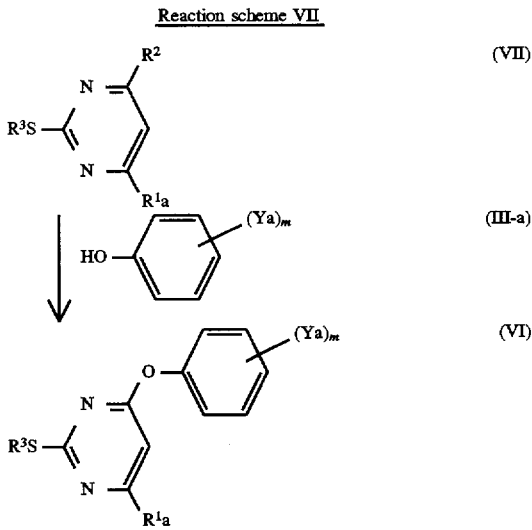

wherein R$^1$a, R$^2$, R$^3$, Ya and m are as defined above.

The above-mentioned nucleophilic displacement on the pyrimidine ring (Reaction schemes III, IV and VII) can be conducted under the same reaction conditions (used base, solvent, temperature and reaction time) as those described about the Reaction scheme I and II.

The 2-benzyloxy-4-phenoxypyrimidine derivative represented by the above formula (I) of the present invention (hereinafter referred to as "compound of the present invention") exhibits reliable herbicidal activity at a low application dose and shows good selectivity between crops and weeds. Thus, a herbicidal composition containing the compound as an active ingredient may suitably be used in pre- or post-emergence weed control treatment for protecting important crops such as wheat, rice, corn, soybean, cotton, beet, potato, tomato or the like from weeds irrespective of dicotyledons and monocotyledons.

Examples of dicotyledonous weeds which could be controlled by the application of the herbicidal composition of the present invention are genera Amaranthus, Bidens, Stellaria, Abutilon, Convolvulus, Matricaria, Galium, Lindernia, and the like.

Examples of monocotyledonous weeds include genera Echinochloa, Setaria, Digitaria, Avena, Cyperus, Alisma, Monochoria, and the like.

Application sites of the herbicidal composition of the present invention may be not only agricultural lands such as upland fields, paddy fields and orchards but also nonagricultural lands such as athletic fields and factory sites.

The compound of the present invention may also be applied for producing ornamental products resembling to dried flowers, since spraying the compounds of the present invention to the foliage may result whitening thereof.

Although the compound of the present invention may be applied as it is, they are generally applied after formulated with an adjuvant into various forms of compositions such as powders, wettable powders, granules, or emulsifiable concentrates.

The composition is usually formulated in such a way that it contains one or more of the compounds of the present invention at an amount of 0.1 to 95% by weight, preferably 0.5 to 90% by weight, more preferably 2 to 70% by weight.

Among adjuvants including carriers, diluents and surface active agents, suitable solid carriers are talc, kaolin, bentonite, diatomaceous earth, white carbon, clay, and the like. Suitable liquid diluents are water, xylene, toluene, chlorobenzene, cyclohexane, cyclohexanone, dimethylsulfoxide, dimethylformamide, alcohol, and the like.

Surface active agents may be properly selected depending upon their effects, and suitable emulsifying agents include polyoxyethylene alkylaryl ether, polyoxyethylene sorbitan monolaurate, and the like. Suitable dispersing agents include lignin sulfonate, dibutylnaphthalene sulfonate, and the like. Suitable wetting agents are alkyl sulfonates, alkylphenyl sulfonates, and the like.

The above mentioned compositions include those which are to be applied as such and those which are to be applied after diluted to a proper concentration by using diluents such as water. When applied in a diluted form, the compound of the present invention is contained preferably at a concentration of 0.001 to 1.0% by weight. Application dose of the compounds of the present invention is 0.01 to 10 kg/ha, preferably 0.05 to 5 kg/ha.

The concentrations and application doses defined above are varied depending on dosage forms, time of application, way of application, application sites, plants to be treated, and the like. Thus, modifications thereof are possible without limited to the above defined range. Further, the compounds of the present invention may be used in combination with other active ingredients such as fungicides, insecticides, acaricides and herbicides.

EXAMPLES

The 2-benzyloxy-4-phenoxypyrimidine derivative of the present invention, production processes and use thereof will be more specifically described by way of the following synthesis examples, formulation examples and test examples.

It should be also understood that the present invention are not limited to these examples without departing from the scopes thereof.

The abbreviations employed in the synthesis examples and reference synthesis examples are as follows:

DMF: dimethylformamide

NaH: sodium hydride

THF: tetrahydrofuran

KI: potassium iodide m-CPBA: m-chloroperbenzoic acid

Synthesis Example 1

Synthesis of 4-methyl-6-phenoxy-2-(phenylmethoxy)pyrimidine (Compound No. I-4)

Benzyl alcohol (0.29 g, 0.0013×2.0 mol) was dissolved in THF (20 ml), then NaH (0.07 g (60%), 0.0013×1.2 mol) was added thereto. When the evolution of hydrogen stopped, 4-methyl-2-methylsulfonyl-6-phenoxypyrimidine (Compound No. V-4) (0.35 g, 0.0013 mol) which had been synthesized as described in Reference synthesis example 8 below was added thereto and the mixture was allowed to react for about 2 hours at room temperature. The reaction solution was poured into water, extracted with ethyl acetate. Thereafter, the organic layer was washed with aqueous saturated sodium chloride, dried over anhydrous sodium sulfate and concentrated, then purified on silica gel column to obtain the end product. Yield: 0.29 g (79%).

Synthesis Example 2

Synthesis of 4-methyl-6-(3-methylphenoxy)-2-(phenylmethoxy)pyrimidine (Compound No. I-214)

The end product was obtained in a similar manner to Synthesis example 1, by starting from m-cresol (0.35 g, 0.0017×2.0 mol) and 4-chloro-6-methyl-2-(phenylmethoxy)-pyrimidine (Compound No. II-4) (0.40 g, 0.0017 mol) which had been synthesized as described in Reference synthesis example 3 below.

Yield: 0.55 g (100%).

Synthesis Example 3

Synthesis of 2-phenylmethoxy-4-(2-propenyloxy)-6-[3-(trifluoromethyl)phenoxy]pyrimidine (Compound No. I-302)

The end product was obtained in a similar manner to Synthesis example 1, by starting from benzyl alcohol (0.16 g, 0.00134×1.1 mol) and 2-methylsulfonyl-4-(2-propenyloxy)-6-[3-(trifluoromethyl)phenoxy]pyrimidine (Compound No. V-233) (0.50 g, 0.00134 mol).

Yield: 0.18 g (31%).

Synthesis Example 4

Synthesis of 4-methyl-2-phenylmethoxy-6-[3-(trifluoromethyl)phenoxy]pyrimidine (Compound No. I-304)

The end product was obtained in a similar manner to Synthesis example 1, by starting from benzyl alcohol (0.23 g, 0.00105×2.0 mol) and 4-methyl-2-methylsulfonyl-6-[3-(trifluoromethyl)phenoxy]pyrimidine (Compound No. V-235) (0.35 g, 0.00105 mol).

Yield: 0.21 g (54%).

Synthesis Example 5

Synthesis of 4-methoxy-2-phenylmethoxy-6-[3-(trifluoromethyl)phenoxy]pyrimidine (Compound No. I-307)

The end product was obtained in a similar manner to Synthesis example 1, by starting from benzyl alcohol (0.155 g, 0.00144×1.0 mol) and 4-methoxy-2-methylsulfonyl-6-[3-(trifluoromethyl)phenoxy]pyrimidine (Compound No. V-241)(0.50 g, 0.00144 mol).

Yield: 0.21 g (39%).

Synthesis Example 6

Synthesis of 4-methylthio-2-phenylmethoxy-6-[3-(trifluoromethyl)phenoxy]pyrimidine (Compound No. I-315)

Aqueous sodium thiomethoxide (15%, 2.75 g, 0.0059×1.0 mol) was added dropwise in 4,6-dichloro-2-(phenylmethoxy)pyrimidine (Compound No. II-26) (1.5 g, 0.0059 mol) dissolved in THF at room temperature. After allowed to react for 2 hours, the reaction solution was partitioned between ethyl acetate and aqueous saturated sodium hydrogen carbonate. The organic layer was washed with aqueous saturated sodium chloride, dried over anhydrous sodium sulfate and concentrated, then purified on a silica gel column to obtain 4-chloro-6-methylthio-2-(phenylmethoxy)pyrimidine (Compound No. II-15) as an intermediate.

Thus obtained intermediate was dissolved in DMF, thereafter a THF/DMF solution containing 3-(trifluoromethyl)phenol (0.95 g, 0.0059×1.0 mol), NaH (0.24 g (ca. 60% in mineral oil), 0.0059×1.0 mol), and KI (0.45 g, 0.0059×0.5 mol) was added thereto, and the resulting solution was refluxed for about 7 hours. The reaction solution was partitioned between ethyl acetate and aqueous saturated sodium hydrogen carbonate. The organic layer was washed with aqueous saturated sodium chloride, dried over anhydrous sodium sulfate and concentrated, then purified on a silica gel column to obtain the end product.

Yield: 2.0 g (88.0%).

Synthesis Example 7

Synthesis of 4-ethylthio-2-phenylmethoxy-6-[3-(trifluoromethyl)phenoxy]pyrimidine (Compound No. I-316)

The end product was obtained in a similar manner to Synthesis example 1, by starting from 3-(trifluoromethyl)-phenol (0.35 g, 0.00142×1.5 mol) and 4-chloro-6-ethylthio-2-(phenylmethoxy)pyrimidine (Compound No. II-16) (0.40 g, 0.00142 mol) which had been synthesized as described in Reference synthesis example 5.

Yield: 0.49 g (85%).

Synthesis Example 8

Synthesis of 4-bromo-2-phenylmethoxy-6-[3-(trifluoromethyl)phenoxy]pyrimidine (Compound No. I-325)

An alkoxide was prepared from benzyl alcohol (0.40 g, 0.0025×1.5 mol) and NaH (0.106 g (ca. 60% in mineral oil), 0.00252×1.05 mol) in THF.

4-Bromo-2-methylsulfonyl-6-[3-(trifluoromethyl)-phenyl]pyrimidine (Compound No. V-253) (1.0 g, 0.00252 mol) was added thereto and the resulting solution was stirred for about 2 hours at room temperature. Thereafter, the reaction solution was partitioned between ethyl acetate and aqueous saturated sodium hydrogen carbonate. The organic layer was washed with aqueous saturated sodium chloride, dried over anhydrous sodium sulfate and concentrated, then purified on a silica gel column to obtain an oily product.

Yield: 0.30 g (37%).

Synthesis Example 9

Synthesis of 4-chloro-2-phenylmethoxy-6-[3-(trifluoromethyl)phenoxy]pyrimidine (Compound No. I-326)

The end product was obtained in a similar manner to Synthesis example 1, by starting from 3-(trifluoromethyl)-phenol (0.35 g, 0.0020×2.0 mol) and 4,6-dichloro-2-(phenylmethoxy)pyrimidine (Compound No. II-26)(0.50 g, 0.0020 mol).

Yield: 0.60 g (80%).

Synthesis Example 10

Synthesis of 4-iodo-2-phenylmethoxy-6-[3-(trifluoromethyl)-phenoxy]pyrimidine (Compound No. I-327)

The end product was obtained in a similar manner to Synthesis example 1, by starting from benzyl alcohol (0.22 g, 0.0018×1.1 mol) and 4-iodo-2-methylsulfonyl-6-[3-(trifluoromethyl) phenoxy]pyrimidine (Compound No. V-255) (0.8 g, 0. 0018 mol).

Yield: 0.63 g (74%).

Physicochemical properties of the compounds of the Synthesis examples 1 to 10 and other compounds synthesized in a similar manner to Synthesis example 1 are shown in Table 6 below.

TABLE 6

| No. | Property or m.p. (°C.) | $^1$H-NMR (60 MHz, CDCl$_3$, δ) |
|---|---|---|
| I-4 | 87–88 | 2.34(3H, s), 5.18(2H, s), 6.21(1H, s), 6.8–7.6(10H, m) |
| I-214 | oily | 2.34(6H, s), 5.20(2H, s), 6.17(1H, s), 6.6–7.5(4H, m), 7.21(5H, s) |
| I-301 | 52–54 | 5.17(2H, s), 6.46(1H, d, J = 5.5Hz), 7.20(5H,s), 7.2–7.7(4H, complex), 8.27(1H, d, J = 5.5Hz) |
| I-302 | 93–94 | 4.6–4.9(2H, m), 5.0–5.5(2H, m), 5.16(2H, s) 5.5–6.2(1H, m), 5.77(1H, s), 7.20(5H, s), 7.2–7.6(4H, m) |
| I-304 | oily | 2.37(3H, s), 5.11(2H, s), 6.27(1H, s), 7.0–7.7(4H, m), 7.16(5H, s) |
| I-307 | oily | 3.85(3H, s), 5.13(2H, s), 5.73(1H, s), 7.1–7.6(4H, m), 7.17(5H, s) |
| I-311 | oily | 1.30(3H, t, J = 6.9Hz), 4.28(2H, q, J = 6.9Hz), 5.11(2H, s), 5.67(1H, s), 7.0–7.5(4H, m), 7.14(5H, s) |
| I-315 | 57–60 | 2.49(3H, s), 5.19(2H, s), 6.32(1H, s), 7.0–7.6(4H, m), 7.22(5H, s) |
| I-316 | oily | 1.30(3H, t, J = 6.9Hz), 3.07(2H, q, J = 6.9Hz), 5.17(2H, s), 6.26(1H, s), 7.0–7.6(4H, m), 7.20(5H, s) |
| I-325 | oily | 5.16(2H, s), 6.68(1H, s), 7.1–7.6(4H, m), 7.20(5H, s) |
| I-326 | 91–93 | 5.12(2H, s), 6.46(1H, s), 7.1–8.0(9H, m) |
| I-327 | oily | 5.11(2H, s), 6.93(1H, s), 7.1–7.7(4H, complex) 7.17 (5H, s) |
| I-574 | 47–50 | 2.37(3H, s), 5.08(2H, s), 6.24(1H, s), 7.07(2H, d, J = 8.9Hz), 7.15(5H, s), 7.44(2H, d, J = 8.9Hz) |
| I-964 | oily | 4.6–4.9(2H, m), 5.0–5.5(2H, m), 5.16(2H, s) 5.5–6.2(1H, m), 5.77(1H, s), 7.20(5H, s), 7.2–7.6(4H, m) |
| I-967 | 76–77 | 1.32(3H, t, J = 6.9Hz), 4.32(2H, q, J = 6.9Hz), 5.11(2H, s), 5.73(1H, s), 6.9–7.6(8H, m) |
| I-1107 | oily | 2.27(3H, s), 3.89(3H, s), 5.14(2H, s), 5.76(1H, s), 6.8–7.6(8H, m) |
| I-1195 | oily | 2.18(3H, s), 5.20(2H, s), 6.23(1H, s), 6.7–7.6(9H, m) |
| I-1234 | 50–53 | 2.26(3H, s), 5.07(2H, s), 6.21(1H, s), 6.8–7.6(8H, m) |
| I-1366 | oily | 1.28(3H, t, J = 6.9Hz), 4.30(2H, q, J = 6.9Hz), 5.24(2H, s), 5.70(1H, s), 6.9–7.5(8H, m) |
| I-1494 | oily | 2.26(3H, s), 3.87(3H, s), 5.12(2H, s), 5.75(1H, s), 6.8–7.6(4H, m), 7.06(4H, s) |
| I-1557 | oily | 3.68(3H, s), 3.86(3H, s), 5.07(2H, s), 5.73(1H, s), 6.68(2H, d, J = 8.5Hz), 7.10(2H, d, J = 8.5Hz), 7.0–7.6(4H, m) |
| I-1561 | 55–57 | 1.31(3H, t, J = 6.9Hz), 4.30(2H, q, J = 6.9Hz), 5.08(2H, s), 5.71(1H, s), 7.0–7.6(8H, m) |
| I-1623 | oily | 3.86(3H, s), 5.17(2H, s), 5.76(1H, s), 7.1–7.7(8H, m) |
| I-1752 | oily | 3.87(3H, s), 5.09(2H, s), 5.76(1H, s), 7.0–7.6(8H, m) |

Reference Synthesis Example 1

Synthesis of 6-chloro-2-phenylmethoxy-4-(2-propenyloxy)-pyrimidine (Compound No. II-2)

Into a 50 ml eggplant type flask, 4,6-dichloro-2-(phenylmethoxy)pyrimidine (Compound No. II-26) (1.5 g, 5.9 mmol) and allyl alcohol (0.342 g, 5.9×1.0 mmol) were introduced, and dimethylformamide (20 ml) was added thereto to prepare a solution. While cooling with ice, 60% sodium hydride (0.247 g, 5.9×1.05 mmol) which had been washed with hexane was added. After stirred for overnight at room temperature, the reaction solution was poured into iced water and extracted with toluene (40 ml). The organic phase was washed with aqueous saturated sodium chloride, dried over anhydrous sodium sulfate, and thereafter, the solvent was distilled off to obtain an oily product. The product was then purified on silica gel column chromatography (Wakogel C300, 300 ml, hexane/ethyl acetate=25/1000(v/v)) to obtain the end compound.

Yield: 0.7 g (42.9%).

Reference Synthesis Example 2

Synthesis of 4-chloro-6-(3-methyl-2-butenyloxy)-2-(phenylmethoxy)pyrimidine (Compound No. II-3)

(1) Synthesis of an intermediate, 4-chloro-6-(3-methyl-2-butenyloxy) -2-(methylsulfonyl) pyrimidine (Compound No. VIII-3)

Into a 100 ml eggplant type flask, 4-chloro-6-(3-methyl-2-butenyloxy) -2-(methylthio) pyrimidine (Compound No. VII-3) (2.45 g, 10.0 retool) was introduced, and dichloromethane (40 ml) was added thereto to prepare a solution. While cooling with ice, m-CPBA (3.45 g, 10.0×2.0 mmol) was added by small portions. An hour later, ice bath was removed, and the solution was then stirred for overnight at room temperature. Aqueous saturated sodium hydrogen carbonate was added to the reaction solution, and after shaking, an organic phase was separated. The organic phase was washed with aqueous saturated sodium chloride, dried over anhydrous sodium sulfate, and thereafter, the solvent was distilled off to obtain an oily product (2.5 g). The product was then purified on silica gel column chromatography (Wakogel C300, 300 ml, hexane/ethyl acetate=(300 ml/150 ml) to obtain the Compound No. VIII-3 from the fraction of 300 ml to 380 ml.

Yield: 0.7 g (25.3%). Oily product. $^1$H-NMR (60 MHz, CDCl$_3$,δ): 1.77(6H,s), 3.30(3H,s), 4.9–5.1(2H,d,7 Hz), 5.3–5.6(1H,m), 6.90(1H,s). (2) Synthesis of the Compound No. II-3 from the intermediate Into a 50 ml eggplant type flask, the intermediate obtained from the preceding section (1), Compound No. VIII-3 (0.50 g, 1.8 mmol) and benzyl alcohol (0.195 g, 1.8×1.0 mmol) were introduced, and DMF (10 ml) was added thereto to prepare a solution. While cooling with ice, 60% sodium hydride (79.5 mg, 1.8×1.1 mmol) which had been washed with hexane was added. After stirred for overnight at room temperature, the reaction solution was poured into iced water and extracted with toluene (20 ml). The organic phase was washed with aqueous saturated sodium chloride, dried over anhydrous sodium sulfate, and thereafter, the solvent was distilled off to obtain an oily product (0.6 g). The product was then purified on silica gel column chromatography (Wakogel C300, 100 ml, hexane/ethyl acetate=300 ml/30 ml) to obtain the Compound No. II-3.

Yield: 0.3 g (54.7%). Purity: 91.9%. (Rt=10.7 min.: ODSF411A, acetonitrile/water=70/30(v/v), 1 ml/min., 250 nm). $^1$H-NMR (60 MHz, CDCl$_3$, δ): 1.70(6H,s), 4.75(2H, d,7 Hz), 5.2–5.5(1H,m), 5.33(2H,s), 6.27(1H,s), 7.1–7.5 (5H,m).

Reference Synthesis Example 3

Synthesis of 4-chloro-6-methyl-2-(phenylmethoxy)pyrimidine (Compound No. II-4)

(1) Synthesis of an intermediate, 4-chloro-6-methyl-2-(methylsulfonyl)pyrimidine (Compound No. VIII-4)

4-Chloro-6-methyl-2-(methylthio)pyrimidine (2.0 g, 0.0114 mol) (Compound No. VII-4) was dissolved in chloroform, and m-CPBA (5.64 g (purity ca.70%), 0.0114× 2.0 mol) was added thereto, and then the resulting solution was allowed to react for about 2 hours at room temperature. The reaction solution was partitioned between chloroform and aqueous saturated sodium hydrogen carbonate to separate an organic phase. The organic phase was washed with aqueous saturated sodium chloride, dried over anhydrous sodium sulfate and concentrated, thereafter the residue was purified on a silica gel column to obtain the Compound No. VIII-4.

Yield: 2.25 g (95%). Melting point: 67°–70° C. $^1$H-NMR (60 MHz, CDCl$_3$, δ): 2.63(3H,s), 3.30(3H,s), 7.38 (1H,s).

(2) Synthesis of the Compound No. II-4 from the intermediate

In THF, an alkoxide was prepared from benzyl alcohol (1.65 g, 0.010×1.5 mol) and NaH (0.43 g, (ca. 60% in mineral oil), 0.010×1.05 mol). The Compound No. VIII-4 (2.10 g, 0.010 mol) obtained from the preceding section (1) was added thereto and allowed to react for 2 hours at room temperature. The reaction solution was partitioned between ethyl acetate and aqueous saturated sodium hydrogen carbonate to separate an organic phase. The organic phase was washed with aqueous saturated sodium chloride, dried over anhydrous sodium sulfate and concentrated, and thereafter the residue was purified on a silica gel column to obtain the title compound as an oily product.

Yield: 1.31 g (56%). $^1$H-NMR (60 MHz, CDCl$_3$, δ): 2.37(3H,s), 5.33(2H,s), 6.73(1H,s), 7.1–7.6(5H,m).

Reference Synthesis Example 4

Synthesis of 4-chloro-6-methoxy-2-(phenylmethoxy)pyrimidine (Compound No. II-7)

(1) Synthesis of an intermediate, 4-chloro-6-methoxy-2-(methylthio)pyrimidine (Compound No. VII-7)

4,6-Dichloro-2-(methylthio)pyrimidine (compound VII-23) (19.5 g, 0.100 mol) was dissolved in tetrahydrofuran (200 ml) which had just been distilled, and then methyl alcohol (3.2 g, 0.100×1.0 mol) was added thereto. Under cooling with ice, 60% sodium hydride (4.4 g, 0.100×1.1 mol) was added while stirring. After stirred for 3 hours, the reaction solution was poured into water, and extracted with toluene. The organic phase was washed with aqueous saturated sodium chloride, dried over anhydrous sodium sulfate and filtered, and thereafter the solvent was distilled off to obtain the Compound No. VII-7.

Yield: 19.0 g. $^1$H-NMR (60 MHz, CDCl$_{13}$, δ) 2.47(3H,s), 3.85(3H,s), 6.27 (1H,s).

(2) Synthesis of an immediately preceding intermediate, 4-chloro-6-methoxy-2-(methylsulfonyl)pyrimidine (Compound No. VIII-7)

The intermediate obtained from the preceding section (1), the Compound No. VII-7 (19.0 g, 0.100 mol) was dissolved in acetic acid (200 ml), and aqueous 31% hydrogen peroxide (25.2 g, 0.100×2.3 mol) was added thereto, and the mixture was heated to 100° C. while stirring. After stirred for 2 hours, the reaction solution was poured into water and extracted with ethyl acetate. The organic phase was washed with aqueous saturated sodium chloride, dried over anhydrous sodium sulfate and concentrated, and thereafter the solvent was distilled off to obtain a crude product 20.0 g. The product was then purified on silica gel column chromatography (Wakogel C300, 300 ml, ethyl acetate/hexane=400 ml/400 ml) to obtain the Compound No. VIII-7 as a white crystal from the fraction of 300 ml to 600 ml.

Yield: 11.5 g. Melting point: 68°–74° C. $^1$H-NMR (60 MHz, CDCl$_3$, δ): 3.30(3H,s), 4.07(3H,s), 6.87(1H,s)

(3) Synthesis of the Compound No. II-7 from the immediately preceding intermediate 4-Chloro-6-methoxy-2-(methylsulfonyl)pyrimidine (Compound No. VIII-7) (0.80 g, 0.0036 mol) and benzyl alcohol (0.39 g, 0.0036 mol) were dissolved in toluene (10 ml), and then 60% sodium hydride (0.16 g, 0.0036×1.1 mol) was added thereto while cooling with ice. After stirred for overnight at room temperature, the reaction solution was poured into water and extracted of ethyl acetate. The organic phase was washed with aqueous saturated sodium chloride, dried over anhydrous sodium sulfate and filtered, thereafter the solvent was distilled off to obtain 0.92 g of a crude product. The product was then purified on silica gel column chromatography to obtain the Compound No. II-7 as an oily product.

Yield: 0.5 g. $^1$H-NMR (60 MHz, CDCl$_3$, δ): 3.80(3H,s), 5.30(2H,s), 6.20(1H,s), 7.1–7.5(5H,m)

Reference Synthesis Example 5

Synthesis of 4-chloro-6-ethylthio-2-(phenylmethoxy)-pyrimidine (Compound No. II-16)

Ethane thiol (0.366 g, 0.0059×1.0 mol) was dissolved in THF, and then NaH (0.24 g, (ca.60% in mineral oil), 0.0059×1.0 mol) was added thereto. The resulting solution was added dropwise to 4,6-dichloro-2-(phenylmethoxy) pyrimidine (Compound No. II-26) (1.5 g, 0.0059 mol) dissolved in THF and then stirred for about 3 hours at room temperature.

In order to completely remove the unreacted starting material (Compound No. II-26), 40% aqueous methylamine (0.23 g, 0.0059×0.5 mol) was added and stirred for about 1 hour at room temperature. The reaction solution was poured into water and extracted with ethyl acetate to separate an organic phase. The organic phase was washed with aqueous saturated sodium chloride, dried and concentrated, thereafter purified on a silica gel column to obtain the Compound No. II-16.

Yield: 1.55 g (94%). Melting point: 55°–57° C. $^1$H-NMR (60 MHz, CDCl$_3$, δ) 1.30(3H, t,J=6.9 Hz), 3.08(2H, q,J=6.9 Hz), 5.34(2H,s), 6.70(1H,s), 7.0–7.6(5H,m).

Reference Synthesis Example 6

Synthesis of 4,6-dibromo-2-(phenylmethoxy)pyrimidine (Compound No. II-25)

(1) Synthesis of an intermediate, 4,6-dibromo-2-(methylthio)pyrimidine (Compound No. VII-22)

Into a 300 ml eggplant type flask, 4,6-dihydroxy-2-(methylthio)pyrimidine (12.5 g, 0.079 mol) and phosphoryl tribromide (49.8 g, 0.079×2.1 mol) were introduced and the flask was immersed in an 80° C. oil bath, and the mixture was then stirred for 30 minutes. The reaction mixture was allowed to cool to room temperature and dissolved in ethyl acetate, and then poured onto ice to separate an organic phase. The organic phase was washed with aqueous saturated sodium chloride, dried over anhydrous sodium sulfate and filtered, and thereafter the solvent was distilled off. The residue was purified on silica gel column chromatography (Wakogel C300, 300 ml, ethyl acetate/hexane=35 ml/700 ml) to obtain a white crystal from the fraction of 120 ml to 480 ml.

Yield: 14.6 g. Melting point: 90°–92° C.

(2) Synthesis of an immediately preceding intermediate, 4,6-dibromo-2-(methylsulfonyl)pyrimidine (Compound No. VIII-22)

Into a 100 ml eggplant type flask, the intermediate obtained from the preceding section (1), the Compound No. VII-22 (5.7 g, 20.1 mmol) was introduced, then dissolved in acetic acid (50 ml), and aqueous 31% hydrogen peroxide (4.5 g, 20.1×2.1 mmol) was added thereto and the mixture was allowed to react at 100° C. for 3 hours.

Since HPLC monitoring showed that 13.2% of the starting material was remained (Rt=5.1 min., acetonitrite/water= 70/30 (v/v), 1 ml/min., 250 nm), aqueous 31% hydrogen peroxide (1.0 g, 20.1×0.47 mmol) was further added thereto and the mixture was allowed to react for another 1 hour. After allowed to cool to room temperature, the reaction solution was poured into iced water and extracted with toluene. The organic phase was washed with aqueous saturated sodium chloride, dried over anhydrous sodium sulfate, and thereafter the solvent was distilled off to obtain the Compound No. VIII-22 as a white crystal.

Yield: 4.5 g (72.5%). Purity: 97.5%. (Rt=2.3 min.: ODS411A, acetonitrile/water =70/30, 1 ml/min., 250 nm) Melting point: 12120°–124° C.

(3) Synthesis of the Compound No. II-25 from the immediately preceding intermediate 4,6-Dibromo-2-(methylsulfonyl)pyrimidine (Compound No. VIII-22) (1.5 g, 0.00476 mol) was dissolved in toluene, and then benzyl alcohol (0.515 g, 0.00476×1.0 mol) was added thereto. Under cooling with ice, 60% sodium hydride (0.21 g, 0.00476×1.1 mol) was added while stirring. After stirred for 6 hours, the reaction solution was poured into water and extracted with toluene. The organic phase was washed with aqueous saturated sodium chloride, dried over anhydrous sodium sulfate and filtered, and thereafter the solvent was distilled off. The residue was purified on silica gel column chromatography (Wakogel C300, 100 ml, ethyl acetate/hexane=20 ml/400 ml) to obtain the Compound No. II-25 as an oily product from the fraction of 100 ml to 120 ml.

Yield: 0.5 g. $^1$H-NMR (60 MHz, CDCl$_3$, δ): 5.20(2H,s), 7.10(1H,s), 7.1–7.8(5H,m)

Reference Synthesis Example 7

Synthesis of 4,6-dichloro-2-(phenylmethoxy)pyrimidine (Compound No. II-26)

Into a 500 ml eggplant type flask, 4,6-dichloro-2-(methylsulfonyl)pyrimidine (Compound No. VIII-23) (21.3 g, 93.8 mmol) and benzyl alcohol (10.1 g, 93.8×1.0 mmol) were introduced, and dimethylformamide (150 ml) was added thereto to prepare a solution. While stirring in ice bath, 60% sodium hydride (3.94 g, 93.8×1.05 mmol) which had been washed with hexane was added. After bubbling ceased, ice bath was removed and the reaction solution was stirred for 2 hours at room temperature. The reaction mixture was poured onto ice and the separated organic matter was extracted with ethyl acetate. The organic phase was washed successively with diluted hydrochloric acid and aqueous saturated sodium chloride, dried over anhydrous sodium sulfate, and thereafter the solvent was distilled off. The residue was purified on silica gel column chromatography (Wakogel C300, ethyl acetate/hexane=1/50) to obtain the Compound No. II-26.

Yield: 6.5 g (27%). Oily product.

Reference Synthesis Example 8

Synthesis of 4-methyl-2-methylsulfonyl-6-phenoxypyrimidine (Compound No. V-4)

(1) Synthesis of an intermediate, 4-methyl-2-methylthio-6-phenoxypyrimidine

Phenol (1.72 g, 11.5×1.50 mmol) was dissolved in THF, and 60% sodium hydride (0.69 g, 11.5×1.50 mmol) was added thereto to prepare a phenoxide. 4-Chloro-6-methyl-2-(methylthio)pyrimidine (Compound No. VII-4) (2.0 g, 11.5 mmol) was added thereto and the mixture was refluxed for about 8 hours.

The reaction solution was poured into water and extracted with ethyl acetate. The organic phase was washed successively with diluted hydrochloric acid and aqueous saturated sodium chloride, then dried over anhydrous sodium sulfate and concentrated, thereafter purified on a silica gel column to obtain the intermediate.

Yield 1.49 g (56%). Oily product. $^1$H-NMR (60 MHz, CDCl$_3$, δ): 2.34(6H,s), 6.21(1H,s), 6,8–7.6 (5H,m). IR (liq., cm$^{-1}$): 2936, 1576, 1496, 1442, 1386, 1358, 1280, 1200, 1168, 1070, 1024, 994, 964, 922, 834, 768, 696.

(2) Synthesis of the Compound No. V-4 from the intermediate

4-Methyl-2-methylthio-6-phenoxypyrimidine (1.40 g, 0.0060 mol) was dissolved in chloroform, and then m-CPBA (3.12 g, 6.0×2.1 mmol) was added thereto. The resulting solution was allowed to react for 2 hours at room temperature. The reaction solution was concentrated and thereafter purified on a silica gel column.

Yield: 1.20 g (75%). $^1$H-NMR (60 MHz, CDCl$_3$, δ) 2.56(3H,s), 3.12(3H,s), 6.76(1H,s), 6.8–7.7(5H,m). IR (liq., cm$^{-1}$): 3032, 2940, 2368, 1738, 1584, 1542, 1494, 1446, 1392, 1368, 1322, 1206, 1144, 1072, 1026, 966, 912, 864, 816, 754, 698.

Reference Synthesis Example 9

Synthesis of 2-methylsulfonyl-4-[3-(trifluoromethyl)-phenoxy]pyrimidine (Compound No. V-232)

(1) Synthesis of an intermediate, 2-methylthio-4-[3-(trifluoromethyl)phenoxy]pyrimidine In THF, a phenoxide was prepared from 3-(trifluoromethyl)phenol (4.54 g, 0.0187×1.5 mol) was mixed with NaH (1.12 g (ca. 60% in mineral oil), 0.0187× 1.5 mol), and 4-chloro-2-(methylthio)pyrimidine (Compound No. VII-1) (3.0 g, 0.0187 mol) was added thereto and the mixture was refluxed for about 10 hours. The reaction solution was partitioned between ethyl acetate and aqueous saturated sodium hydrogen carbonate to separate an organic phase. The organic phase was washed with aqueous saturated sodium chloride, dried over anhydrous sodium sulfate and concentrated, then recrystallized from a methanol/water system to obtain the intermediate compound.

Yield: 2.85 g (53%). $^1$H-NMR (60 MHz, CDCl$_3$, δ): 2.28(3H,s), 6.47(1H,d,J=5.5 Hz), 7.0–7.6(4H,m), 8.27(1H, d,J=5.5 Hz)

(2) Synthesis of the Compound No. V-232 from the intermediate 2-Methylthio-4-[3-(trifluoromethyl)phenoxy] pyrimidine (2.65 g, 0.00926 mol) was dissolved in chloroform, and then m-CPBA (4.79 g (purity ca.70%), 0.00926×2.1 mol) was added thereto. The resulting solution was allowed to react for about 2 hours at room temperature. The reaction solution was partitioned between chloroform and aqueous saturated sodium hydrogen carbonate to separate an organic phase. The organic phase was washed with aqueous saturated sodium chloride, dried over anhydrous sodium sulfate and concentrated, and thereafter purified on a silica gel column to obtain the Compound No. V-232.

Yield: 2.17 g (74%). Melting point: 117°–121° C. $^1$H-NMR (60 MHz, CDCl$_3$, δ): 3.08(3H,s), 7.08(1H,d, J=5.5 Hz), 7.2–7.8(4H,m), 8.71(1H,d, J=5.5 Hz)

Reference Synthesis Example 10

Synthesis of 4-ethoxy-2-methylsulfonyl-6-[3-(trifluoromethyl)phenoxy]pyrimidine (Compound No. V-242)

(1) Synthesis of an intermediate, 4-ethoxy-2-methylthio-6-[3-(trifluoromethyl)phenoxy]pyrimidine Ethanol (1.18 g, 0.0256×1.0 mol) and NaH (1.02 g, (ca.60% in mineral oil), 0.0256×1.0 mol) were dissolved in THF and 4,6-dichloro-2-methylthiopyrimidine (Compound No. VII-23)(5.0 g, 0.0256 mol) was added thereto. The resulting solution was stirred for about 30 minutes at room temperature. To this reaction solution, m-trifluoromethylphenol (6.23 g, 0.0256×1.5 mol), NaH (1.54 g, (ca.60% in mineral oil), 0.0256×1.5 mol), and KI (2.12 g, 0.0256×0.5 mol) dissolved in DMF were added. The resulting solution was refluxed for about 7 hours. The reaction solution was partitioned between ethyl acetate and aqueous saturated sodium hydrogen carbonate to separate an organic phase. The organic phase was washed with aqueous saturated sodium chloride, dried over anhydrous sodium sulfate and concentrated, and thereafter purified on a silica gel column.

Yield: 6.66 g (79%). Oily product. $^1$H-NMR (60 MHz, CDCl$_3$, δ): 1.32(3H, t,J=6.9 Hz), 2.28(3H, S), 4.30(2H, q,J=6.9 Hz), 5.68(1H,s), 7.4–7.6(4H,m).

(2) Synthesis of the Compound No. V-242 from the intermediate

4-Ethoxy-2-methylthio-6-[3-(trifluoromethyl)phenoxy]-pyrimidine (6.56 g, 0.020 mol) was dissolved in chloroform, and m-CPBA (3.16 g (purity ca.70%), 0.020×2.0 mol) was added thereto. The resulting solution was allowed to react for about 2 hours and 30 minutes at room temperature. The reaction solution was partitioned between chloroform and aqueous saturated sodium hydrogen carbonate to separate an organic phase. The organic phase was washed with aqueous saturated sodium chloride, dried over anhydrous sodium sulfate and concentrated, and thereafter purified on a silica gel column to obtain the Compound No. V-242.

Yield: 6.60 g (92%). Melting point: 114°–116° C. $^1$H-NMR (60 MHz, CDCl$_3$, δ): 1.37(3H, t,J=6.9 Hz), 3.07 (3H,s), 4.46(2H, q,J=6.9 Hz), 6.20(1H,s), 7.0–7.6(4H,m).

Reference Synthesis Example 11

Synthesis of 2-methylsulfonyl-4-trifluoromethyl-6-[3-(trifluoromethyl)phenoxy]pyrimidine (Compound No. V-251)

(1) Synthesis of an intermediate, 2-methylthio-4-trifluoromethyl-6-[3-(trifluoromethyl)phenoxy]pyrimidine m-(Trifluoromethyl)phenol (1.06 g, 0.0044×1.5 mol) and NaH (0.26 g (ca.60% in mineral oil), 0.0044×1.5 mol) were dissolved in THF, and then 4-chloro-6-methylthio-6-(trifluoromethyl)pyrimidine (Compound No. VII-17) (1.0 g, 0.0044 mol) was added thereto. The resulting solution was refluxed for about 7 hours. The reaction solution was partitioned between ethyl acetate and aqueous saturated sodium hydrogen carbonate to separate an organic phase. The organic phase was washed with aqueous saturated sodium chloride, dried over anhydrous sodium sulfate and concentrated. Thereafter, remaining phenol and others were distilled off in a tubular oven (under water flow, 150° C.) to obtain the intermediate compound.

Yield: 1.40 g (90%). Melting point: 39°–41° C. $^1$H-NMR (60 MHz, CDCl$_3$, δ): 2.31(3H,s), 6.66(1H,s), 7.1–7.6 (4H, m).

(2) Synthesis of the Compound No. V-251 from the intermediate

The Compound No. V-251 was obtained in a similar manner to that described in the section (2) of Reference synthesis example 9, by starting from 2-methylthio-4-trifluoromethyl-6-[3-trifluoromethyl)phenoxy]pyrimidine (1.3 g, 0. 0037 mol).

Yield: 1.31 g (92%). Melting point: 119°–123° C. $^1$H-NMR (60 MHz, CDCl$_3$, δ): 3.17(3H,s), 7.1–7.7(5H,m).

Reference Synthesis Example 12

Synthesis of 4-bromo-2-methylsulfonyl-6-[3-(trifluoromethyl)phenoxy]pyrimidine (Compound No. V-253)

(1) Synthesis of an intermediate, 4-bromo-2-methylthio-6-[3-(trifluoromethyl)phenoxy]pyrimidine In THF, a phenoxide was prepared from m-(trifluoromethyl)phenol (1.30 g, 0.00794×1.0 mol) and NaH (0.32 g (ca. 60% in mineral oil), 0.00794×1.0 mol), and 4,6-dibromo-2-(methylthio)pyrimidine (Compound No. VII-22) (2.0 g, 0.00794 mol) was added thereto, and the mixture was then allowed to react for 5 hours at room temperature.

The reaction solution was partitioned between ethyl acetate and aqueous saturated sodium hydrogen carbonate to separate an organic phase. The organic phase was then washed with aqueous saturated sodium chloride, dried over anhydrous sodium sulfate and concentrated, thereafter purified on a silica gel column to obtain the end product.

Yield: 2.35 g (81%). Melting point: 70°–71° C. $^1$H-NMR (60 MHz, CDCl$_3$, δ): 2.26(3H,s), 6.67(1H,s), 7.0–7.6 (4H, m).

(2) Synthesis of the Compound No. V-253 from the intermediate

4-Bromo-2-methylthio-6-[3-(trifluoromethyl)phenoxy]-pyrimidine (2.25 g, 0.00616 mol) was dissolved in chloroform, and m-CPBA (3.19 g (purity ca.70%), 0.00616× 2.1 mol) was added thereto. The resulting solution was allowed to react for about 2 hours at room temperature. The reaction solution was partitioned between chloroform and aqueous saturated sodium hydrogen carbonate to separate an organic phase. The organic phase was then washed with aqueous saturated sodium chloride, dried over anhydrous sodium sulfate and concentrated, and thereafter purified on a silica gel column.

Yield: 2.13 g (87%). Melting point: 95°–97° C. $^1$H-NMR (60 MHz, CDCl$_3$, δ): 3.12(3H,s), 7.23(1H,s), 7.0–7.7 (4H, m).

Reference Synthesis Example 13

Synthesis of 4-chloro-2-methylsulfonyl-6-[3-(trifluoromethyl)phenoxy]pyrimidine (Compound No. V-254)

(1) Synthesis of an intermediate, 4-chloro-2-methylthio-6-[3-(trifluoromethyl) phenoxy]pyrimidine In THF, a phenoxy was prepared from m-(trifluoromethyl)phenol (2.5 g, 0.00154×1.0 mol) and NaH (ca.0.61 g (60% in mineral oil), 0.00154×1.0 mol).

4, 6-Dichloro-2-(methylthio)pyrimidine (Compound No. VII-23) (3.0 g, 0.0154 mol) was added thereto, and the mixture was then allowed to react for 5 hours at room temperature, and thereafter refluxed for about another 30 minutes. The reaction solution was partitioned between ethyl acetate and aqueous saturated sodium hydrogen carbonate to separate an organic phase. The organic phase was washed with aqueous saturated sodium chloride, dried over anhydrous sodium sulfate and concentrated, then recrystallized from a methanol/water system.

Yield: 3.56 g (72%). Melting point: 70°–72° C. $^1$H-NMR (60 MHz, CDCl$_3$, δ): 2.29(3H,s), 6.51(1H,s), 7.1–7.6 (4H, m).

(2) Synthesis of the Compound No. V-254 from the intermediate

The Compound No. V-254 was synthesized in a similar manner to that described in the section (2) of Reference synthesis example 9, by starting from 4-chloro-2-methylthio-6-[3-(trifluoromethyl) phenoxy]pyrimidine (3.4 g, 0.0106 mol).

Yield: 3.48 g (93%). Melting point: 88°–90° C. $^1$H-NMR (60 MHz, CDCl$_3$, δ): 3.12(3H,s), 7.06(1H,s), 7.1–7.7 (4H, m).

Reference Synthesis Example 14

Synthesis of 4-iodo-2-methylsulfonyl-6-[3-(trifluoromethyl) phenoxy]pyrimidine (Compound No. V-235)

(1) Synthesis of an intermediate, 4-iodo-2-methylthio-6-[3-(trifluoromethylphenoxy)]pyrimidine To a THF solution containing m-(trifluoromethyl)phenol (1.0 g, 0.00661×1.0 mol) and NaH (0.24 g (ca. 60% in mineral oil), 0.00661×1.0 mol), 4,6-diiodo-2-(methylthio) pyrimidine (Compound No. VII-24) (2.5 g, 0.00661 mol) was added, and the mixture was then allowed to react for about 3 hours. The reaction solution was partitioned between ethyl acetate and aqueous saturated sodium hydrogen carbonate to separate an organic phase. The organic phase was washed with aqueous saturated sodium chloride, then dried over anhydrous sodium sulfate and concentrated, and thereafter purified on a silica gel column to obtain the end product.

Yield: 1.59 g (58%). Melting point: 73°–75° C. $^1$H-NMR (60 MHz, CDCl$_3$, δ): 2.24(3H,s), 6.93(1H,s), 7.0–7.6 (4H, complex).

(2) Synthesis of the Compound No. V-255 from the intermediate

4-Iodo-2-methylthio-6-[3-(trifluoromethyl)phenoxy]-pyrimidine (1.49 g, 0.00362 mol) was dissolved in chloroform, and m-CPBA (1.87 g (purity ca.70%), 0.00362× 2.1 mol) was added thereto. The resulting solution was allowed to react for about 3 hours at room temperature. The reaction solution was partitioned between chloroform and aqueous saturated sodium hydrogen carbonate. The organic phase was washed with aqueous saturated sodium chloride, dried over anhydrous sodium sulfate and concentrated, thereafter purified on a silica gel column to obtain the Compound No. V-252.

Yield: 0.90 g (56%). Melting point: 102°–106° C. $^1$H-NMR (60 MHz, CDCl$_3$, δ): 3.11(3H,s), 7.0–7.8(5H, complex).

Formulation examples and test examples are hereinafter described. Kinds of carriers (diluents) and additives to be used, as well as mixing ratios thereof and active ingredient contents therein may be modified in a broad range.

In each of the formulation examples, the term "parts" is "parts by weight" if otherwise noted.

Formulation Example 1 (wettable powder)

| | |
|---|---|
| Compound No. I-301 | 50 parts |
| Lignin sulfonate | 5 parts |
| Alkyl sulfonate | 3 parts |
| Diatomaceous earth | 42 parts |

The above ingredients were mixed together and ground finely to form a wettable powder. It may be applied after diluted with water.

Formulation Example 2 (emulsifiable concentrate)

| Compound No. I-327 | 25 parts |
|---|---|
| Xylene | 65 parts |
| Polyoxyethylene alkylaryl ether | 10 parts |

The above ingredients were homogeneously mixed to form an emulsifiable concentrate. It may be applied after diluted with water.

Formulation Example 3 (granules)

| Compound No. I-1234 | 8 parts |
|---|---|
| Bentonite | 40 parts |
| Clay | 45 parts |
| Lignin sulfonate | 7 parts |

The above ingredients were homogeneously mixed, blended with water and processed into a granular form by means of an extrusion granulator to give granules.

Test Example 1 (Weed control test by foliage treatment)

Wettable powders were prepared as described in the Formulation example 1 and diluted to a predetermined concentration. Each of the formulated test compounds was applied at an active ingredient rate of 1000 g/ha onto the foliage of each plant grown to the 1 to 2 leaf stage. The tested plants were pot-cultivated redroot pigweed (Amaranthus retroflexus), wild mustard (Sinapis arvensis), sicklepod (Cassia obtusifolia), black nightshade (Solanum nigrum), velvet-leaf (Abutlion theophrasti), cleavers (Galium aparine), and ivyleaf speedwell (Veronica hederaefolia).

On the 14th day after the application, weed control effects were evaluated by the following criterion. Evaluation rating:

1: less than 30%;
2: 30% to less than 70%;
3: 70% or more.

The results are shown in Table 7.

TABLE 7

| No. | g/ha | AR | SA | CO | SN | AT | GA | VH |
|---|---|---|---|---|---|---|---|---|
| I-4 | 1000 | 3 | 3 | 2 | 3 | 1 | 1 | 2 |
| I-214 | 1000 | 2 | 3 | 3 | 2 | 2 | 1 | 2 |
| I-301 | 1000 | 3 | 3 | 3 | 3 | 2 | 3 | 3 |
| I-302 | 1000 | 2 | 1 | 1 | 1 | 1 | 1 | 1 |
| I-304 | 1000 | 3 | 3 | 3 | 3 | 3 | 3 | 3 |
| I-307 | 1000 | 3 | 3 | 3 | 3 | 3 | 3 | 3 |
| I-311 | 1000 | 2 | 3 | 3 | 2 | 1 | 2 | 2 |
| I-315 | 1000 | 3 | 2 | 3 | 3 | 2 | 3 | 3 |
| I-316 | 1000 | 2 | 3 | 3 | 2 | 2 | 2 | 3 |
| I-322 | 1000 | 2 | 3 | 3 | 1 | 2 | 3 | 3 |
| I-325 | 1000 | 3 | 2 | 3 | 3 | 2 | 3 | 3 |
| I-326 | 1000 | 3 | 3 | 3 | 3 | 3 | 3 | 3 |
| I-327 | 1000 | 3 | 2 | 3 | 3 | 3 | 3 | 3 |
| I-574 | 1000 | 2 | 1 | 2 | 3 | 2 | 2 | 3 |
| I-964 | 1000 | 1 | 1 | 1 | 1 | 1 | 1 | 1 |
| I-967 | 1000 | 1 | 2 | 1 | 2 | 2 | 3 | 2 |
| I-1107 | 1000 | 2 | 2 | 3 | 2 | 2 | 3 | 3 |
| I-1195 | 1000 | 3 | 3 | 3 | 3 | 3 | 3 | 3 |
| I-1234 | 1000 | 3 | 3 | 3 | 3 | 3 | 3 | 3 |
| I-1366 | 1000 | 2 | 1 | 1 | 2 | 2 | 3 | 2 |
| I-1494 | 1000 | 2 | 2 | 1 | 2 | 2 | 1 | 2 |
| I-1557 | 1000 | 3 | 2 | 3 | 2 | 2 | 1 | 2 |

TABLE 7-continued

| No. | g/ha | AR | SA | CO | SN | AT | GA | VH |
|---|---|---|---|---|---|---|---|---|
| I-1561 | 1000 | 2 | 3 | 3 | 2 | 2 | 1 | 2 |
| I-1623 | 1000 | 3 | 2 | 3 | 2 | 2 | 3 | 2 |
| I-1752 | 1000 | 3 | 3 | 3 | 3 | 2 | 3 | 3 |

AR: *Amaranthus retroflexus*
SA: *Sinapis arvensis*
CO: *Cassia obtusifolia*
SN: *Solanum nigrum*
AT: *Abutilon theophrasti*
GA: *Galium aparine*
VH: *Veronica hederaefolia*

Test Example 2 (Germination test)

In a 9 cm diameter Petri dish having the bottom covered with double sheets of filter paper, 6 ml of aqueous suspension of a test compound (containing 50 ppm of active ingredient) was poured and ten seeds of each weed were placed. The tested weeds were redroot pigweed (Amaranthus retroflexus), black nightshade (Solanum nigrum), wild chamomile (Matricaria chamomilla), Green foxtail (Setaria viridis), and rice flatsedge (Cyperus iria).

The seeds was allowed to germinate in a constant-temperature chamber at 28° C., and on the 14th day after the sowing, the inhibition of germination and the retarding of growth were visually observed and evaluated by the following 3-grade criterion. Evaluation rating:

1: less than 30%;
2: 30% to less than 70%;
3: 70% or more.

The results are shown in Table 8.

TABLE 8

| No. | ppm | AR | SN | MC | SV | CI |
|---|---|---|---|---|---|---|
| I-4 | 50 | 3 | 2 | 1 | 1 | 1 |
| I-214 | 50 | 2 | 3 | 1 | 2 | 1 |
| I-301 | 50 | 3 | 3 | 2 | 3 | 3 |
| I-302 | 50 | 1 | 1 | 1 | 1 | 1 |
| I-304 | 50 | 3 | 2 | 3 | 3 | 3 |
| I-307 | 50 | 3 | 1 | 1 | 3 | 3 |
| I-311 | 50 | 2 | 3 | 2 | 1 | 2 |
| I-315 | 50 | 3 | 3 | 2 | 2 | 3 |
| I-316 | 50 | 2 | 3 | 2 | 3 | 2 |
| I-322 | 50 | 2 | 3 | 2 | 3 | 2 |
| I-325 | 50 | 3 | 2 | 3 | 3 | 2 |
| I-326 | 50 | 3 | 1 | 1 | 3 | 3 |
| I-327 | 50 | 2 | 3 | 3 | 2 | 2 |
| I-574 | 50 | 2 | 2 | 1 | 2 | 1 |
| I-964 | 50 | 1 | 1 | 1 | 1 | 1 |
| I-967 | 50 | 3 | 2 | 3 | 1 | 2 |
| I-1107 | 50 | 2 | 3 | 2 | 2 | 1 |
| I-1195 | 50 | 2 | 1 | 1 | 3 | 2 |
| I-1234 | 50 | 2 | 1 | 1 | 1 | 2 |
| I-1366 | 50 | 2 | 1 | 1 | 2 | 2 |
| I-1494 | 50 | 2 | 1 | 2 | 2 | 1 |
| I-1557 | 50 | 3 | 1 | 2 | 1 | 2 |
| I-1561 | 50 | 2 | 3 | 1 | 2 | 2 |
| I-1623 | 50 | 1 | 2 | 2 | 1 | 2 |
| I-1752 | 50 | 3 | 1 | 1 | 3 | 3 |

AR: *Amaranthus retroflexus*
SN: *Solanum nigrum*
MC: *Matricaria chamomilla*
SV: *Setaria viridis*
CI: *Cyperus iria*

What is claimed is:

1. A 2-benzyloxy-4-phenoxypyrimidine derivative represented by the formula (I):

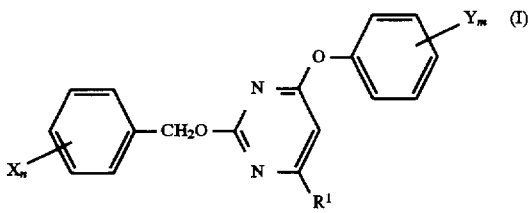

wherein $R^1$ represents hydrogen, a halogen, $C_1$–$C_4$ alkyl, $C_1$–$C_4$ haloalkyl, $C_1$–$C_4$ alkoxy, $C_1$–$C_4$ haloalkoxy, $C_3$–$C_5$ alkenyloxy, $C_1$–$C_4$ alkylthio, $C_1$–$C_4$ haloalkylthio, cyano, or phenyl;

- each X, which may be identical or different if n is greater than 1, represents a halogen, $C_1$–$C_4$ alkyl, $C_1$–$C_4$ haloalkyl, or $C_1$–$C_4$ alkoxy;
- each Y, which may be identical or different if m is greater than 1, represents a halogen, $C_1$–$C_4$ alkyl, $C_1$–$C_4$ haloalkyl, $C_1$–$C_4$ alkoxy, $C_1$–$C_4$ haloalkoxy, $C_1$–$C_4$ alkylthio, or $C_1$–$C_4$ haloalkylthio; and
- n and m each independently represent an integer of 0 to 5.

2. A compound according to claim 1, wherein m represents 0, 1, or 2 and n represents 0, 1, or 2.

3. A compound according to claim 1, wherein $R^1$ represents hydrogen, a halogen, methyl, methoxy, cyano, or methylthio; each X, which may be identical or different if n is greater than 1, represents a halogen, methyl, methoxy, or trifluoromethyl; and each Y, which may be identical or different if m is greater than 1, represents a halogen, methyl, trifluoromethyl, trifluoromethoxy, or trifluoromethylthio.

4. A compound according to claim 1, wherein $R^1$ represents hydrogen, a halogen, methyl, methoxy, cyano, or methylthio; each X, which may be identical or different if n is greater than 1, represents fluorine, chlorine, or methyl; and each Y, which may be identical or different if m is greater than 1, represents fluorine, chlorine, methyl, or trifluoromethyl.

5. A compound according to claim 1, wherein $R^1$ represents hydrogen, a halogen, methyl, methoxy, cyano, or methylthio; n represents 0, 1, or 2; each X, which may be identical or different if n is 2, represents a halogen or methyl bonded to the position 3 or 4; m represents 0, 1, or 2; and each Y, which may be identical or different if m is 2, represents a halogen, methyl, trifluoromethyl, trifluoromethoxy, or trifluoromethylthio bonded to the position 3.

6. A herbicidal composition comprising a 2-benzyloxy-4-phenoxypyrimidine derivative represented by the formula

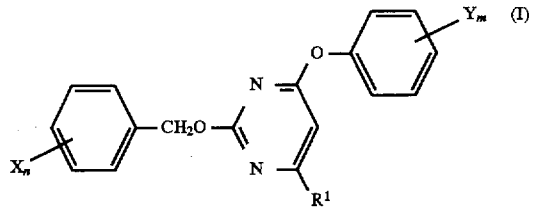

wherein $R^1$, X, Y, m, and n are as defined in claim 1, and an adjuvant.

7. A herbicidal composition according to claim 6, wherein m represents 0, 1, or 2 and n represents 0, 1, or 2.

8. A herbicidal composition according to claim 6, wherein $R^1$ represents hydrogen, a halogen, methyl, methoxy, cyano, or methylthio; each X, which may be identical or different if n is greater than 1, represents a halogen, methyl, methoxy, or trifluoromethyl; and each Y, which may be identical or different if m is greater than 1, represents a halogen, methyl, trifluoromethyl, trifluoromethoxy, or trifluoromethylthio.

9. A herbicidal composition according to claim 6, wherein $R^1$ represents hydrogen, a halogen, methyl, methoxy, cyano, or methylthio; each X, which may be identical or different if n is greater than 1, represents fluorine, chlorine, or methyl; and each Y, which may be identical or different if m is greater than 1, represents fluorine, chlorine, methyl, or trifluoromethyl.

10. A herbicidal composition according to claim 6, wherein $R^1$ represents hydrogen, a halogen, methyl, methoxy, cyano, or methylthio; n represents 0, 1, or 2; each X, which may be identical or different if n is 2, represents a halogen or methyl bonded to the position 3 or 4; m represents 0, 1, or 2; and each Y, which may be identical or different if m is 2, represents a halogen, methyl, trifluoromethyl, trifluoromethoxy, or trifluoromethylthio bonded to the position 3.

* * * * *